(12) United States Patent
Mountziaris et al.

(10) Patent No.: US 10,184,935 B2
(45) Date of Patent: Jan. 22, 2019

(54) QUANTUM DOT-BASED OPTICAL SENSORS FOR RAPID DETECTION AND QUANTITATIVE ANALYSIS OF BIOMOLECULES AND BIOLOGICAL MATERIALS

(75) Inventors: Triantafillos John Mountziaris, Amherst, MA (US); Jun Wang, Amherst, MA (US)

(73) Assignee: University of Massachusetts, Boston, MA (US)

(*) Notice: Subject to any disclaimer, the term of this patent is extended or adjusted under 35 U.S.C. 154(b) by 453 days.

(21) Appl. No.: 13/639,279

(22) PCT Filed: Apr. 5, 2011

(86) PCT No.: PCT/US2011/031149
§ 371 (c)(1),
(2), (4) Date: Jan. 15, 2013

(87) PCT Pub. No.: WO2011/127001
PCT Pub. Date: Oct. 13, 2011

(65) Prior Publication Data
US 2013/0115713 A1 May 9, 2013

Related U.S. Application Data

(60) Provisional application No. 61/320,838, filed on Apr. 5, 2010.

(51) Int. Cl.
*G01N 33/53* (2006.01)
*B82Y 15/00* (2011.01)
*C12Q 1/6816* (2018.01)
*G01N 21/64* (2006.01)
*G01N 33/50* (2006.01)
(Continued)

(52) U.S. Cl.
CPC .......... *G01N 33/5302* (2013.01); *B82Y 15/00* (2013.01); *C12Q 1/6816* (2013.01); *G01N 21/6428* (2013.01); *G01N 33/5005* (2013.01); *G01N 33/533* (2013.01); *G01N 33/588* (2013.01); *G01N 33/6845* (2013.01); *G01N 2333/42* (2013.01); *G01N 2333/4724* (2013.01); *G01N 2333/705* (2013.01)

(58) Field of Classification Search
CPC ........................... B82Y 15/00; C12Q 1/6816; C12Q 2565/607; C12Q 2563/155; G01N 21/6428; G01N 33/5005; G01N 33/533; G01N 33/588; G01N 33/6845; G01N 1/6816; G01N 33/5302; G01N 2333/42; G01N 2333/4724; G01N 2333/705
See application file for complete search history.

(56) References Cited

PUBLICATIONS

Wu et al. COnjugation of glucose oxidase onto Mn-dopped ZnS quantum dots for phosphorescent sensing of glucose in biological fluids. Anal. Chem. 2010, vol. 82, pp. 1427-1433.*
(Continued)

*Primary Examiner* — Shafiqul Haq
(74) *Attorney, Agent, or Firm* — Milstein Zhang & Wu LLC

(57) ABSTRACT

The invention generally relates to detection and analysis of biological materials. In particular; the invention relates to quantum dot-based optical, sensors and methods for rapid detection and quantitative analysis of various biomolecules and biological materials, such as nucleic acids, proteins, cells, etc.

7 Claims, 35 Drawing Sheets

Schematic example of the components of the hybrid nanosensor and an assembled probe. A single biomolecule (probe) is bonded to each QD. The rest of the QD's surface is saturated with the bi-functional organic molecules that are bonded covalently to the QD via a Zn-S bond.

(51) Int. Cl.
*G01N 33/533* (2006.01)
*G01N 33/58* (2006.01)
*G01N 33/68* (2006.01)

(56) References Cited

PUBLICATIONS

Pradhan et al. Efficient, stable, small, and water-soluble doped ZnSe nonocrystal emitters as non-cadmium biomedical labels. Nanoletters 2007, vol. 7, No. 2, pp. 312-317.*

Bussian et al. Tunable magnetic exchange interactions in manganese-doped inverted core-shell ZnSe-CdSe nanocrystals. Nature Materials 2009, vol. 8, pp. 35-40.*

Quantum dot bioconjugates for imaging, labelling and sensing. Nature 2005, vol. 4, pp. 435-446.*

Dyadyusha et al. Quenching of CdSe quantum dot emission, a new approach for biosensing. Chem. Commun., 2005, pp. 3201-3203.*

Algar et al. Adsorption and hybridization of oligonucleotides on mercaptoacetic acid-capped CdSe/ZnS quantum dots and quantum dot-oligonucleotide conjugates. Langmuir 2006, vol. 22, pp. 11346-11352.*

Goldman et al. Luminescent quantum dot-adaptor protein-antibody conjugates for use in fluoroimmunoassays. Phys. stat. sol. (b), vol. 229, No. 1, pp. 407-414.*

Goldman et al. A hybrid quantum dot-antibody fragment fluorescence resonance energy transfer-based TNT sensor. J. Am. Chem. SOc. 2005, vol. 127, pp. 6744-6751.*

Mazumder et al. Review: biofunctionalized quantum dots in biology and medicine. Journal of Nanomaterials. 2009, vol. 2009, pp. 1-17. (Year: 2009).*

* cited by examiner

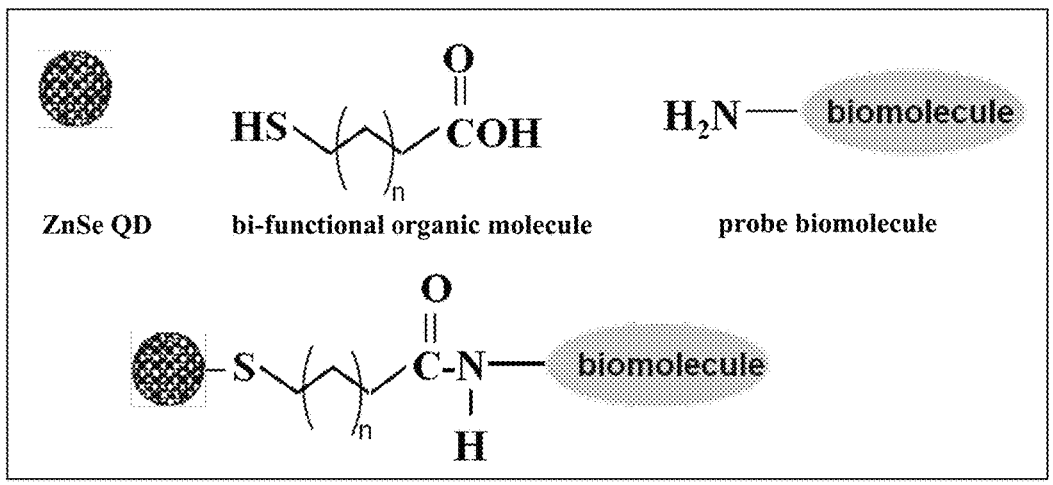

FIG. 1. Schematic example of the components of the hybrid nanosensor and an assembled probe. A single biomolecule (probe) is bonded to each QD. The rest of the QD's surface is saturated with the bi-functional organic molecules that are bonded covalently to the QD via a Zn-S bond.

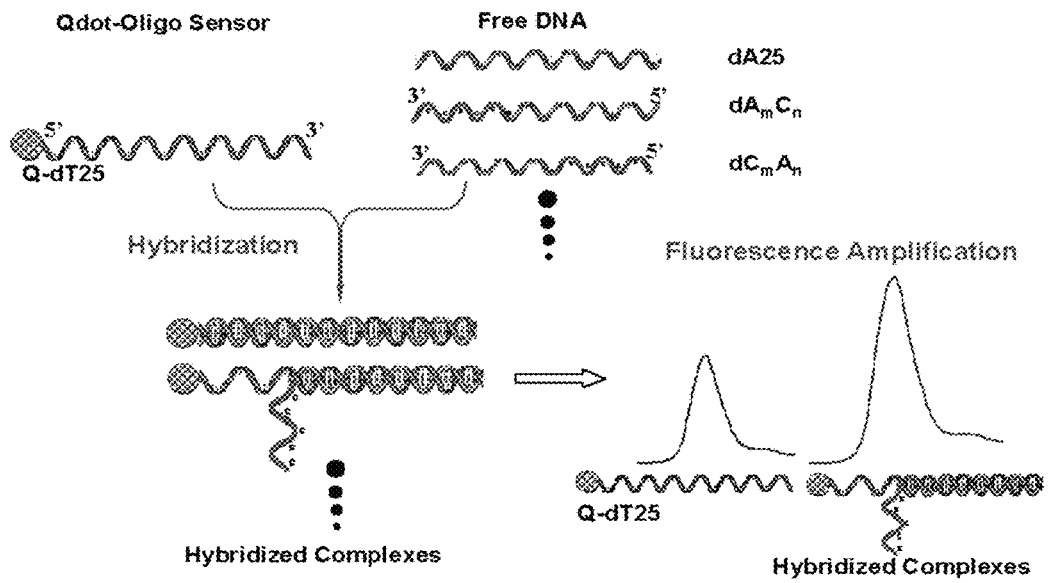

FIG. 2. Schematic of hybridization experiments in which a QD-dT25 sensor is hybridized with various dA-containing oligonucleotides in solution.

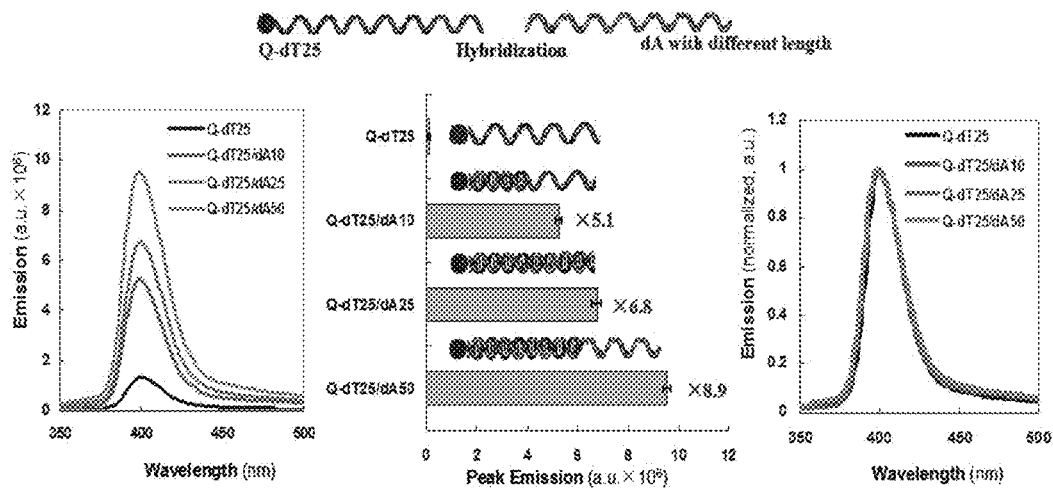

FIG. 3. Hybridization of QD-dT25 sensor with free dA results in structure-dependent fluorescence emission amplification.

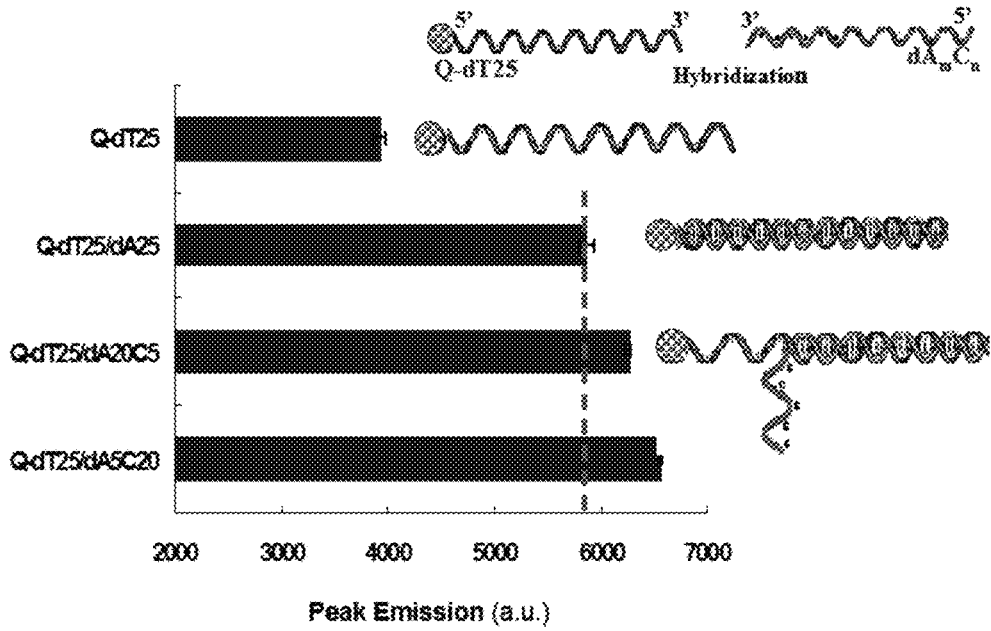

FIG. 4. Fluorescence emission intensity comparison for the following structures: ZnSeQD-dT25 non-hybridized sensor, ZnSeQD-dT25dA25 exactly matched hybridized structure, and two structures containing sequence mismatches at the 3' end of the target DNA: ZnSeQD-dT25dA20C5 and ZnSeQD-dT25dA5C20

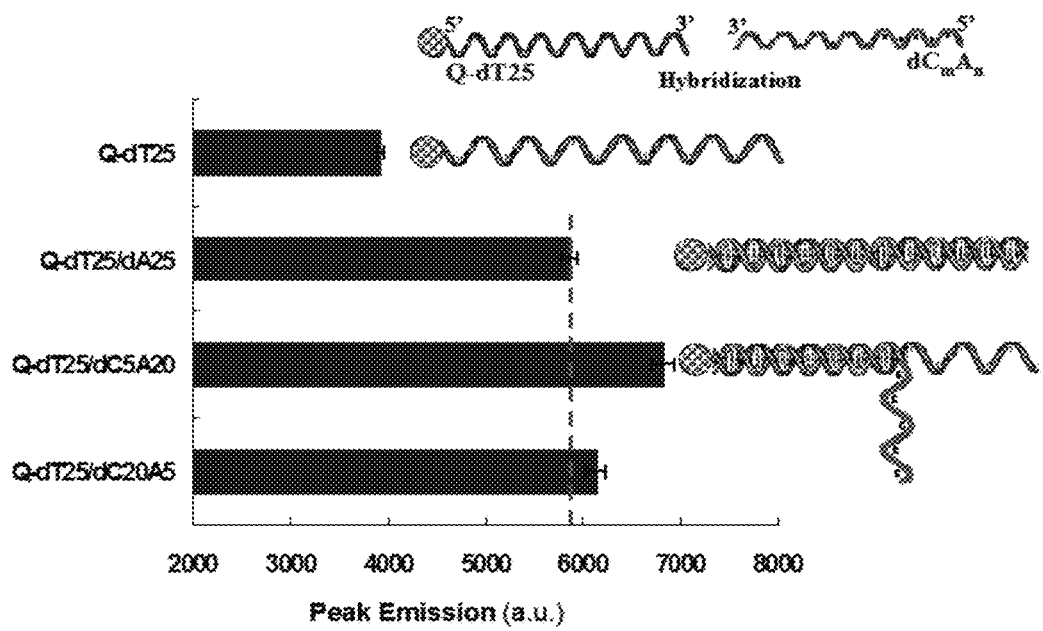
FIG. 5. Fluorescence emission intensity comparison for the following structures: ZnSeQD-dT25 non-hybridized sensor, ZnSeQD-dT25dA25 exactly matched hybridized structure, and two structures containing sequence mismatches at the 5' end of the target DNA: ZnSeQD-dT25dC5A20 and ZnSeQD-dT25dC20A5.

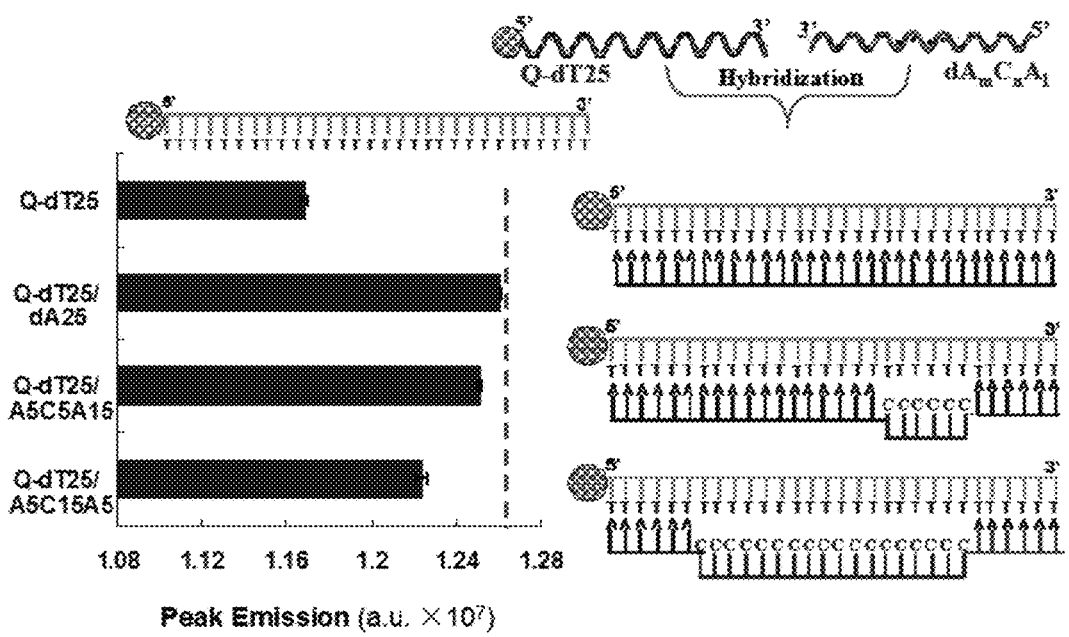
FIG. 6. Fluorescence emission intensity comparison for the following structures: ZnSeQD-dT25 non-hybridized sensor, ZnSeQD-dT25dA25 exactly matched hybridized structure, and two structures containing sequence mismatches in the middle section of the sequence: ZnSeQD-dT25dA5C5A15 and ZnSeQD-dT25dA5C15A5.

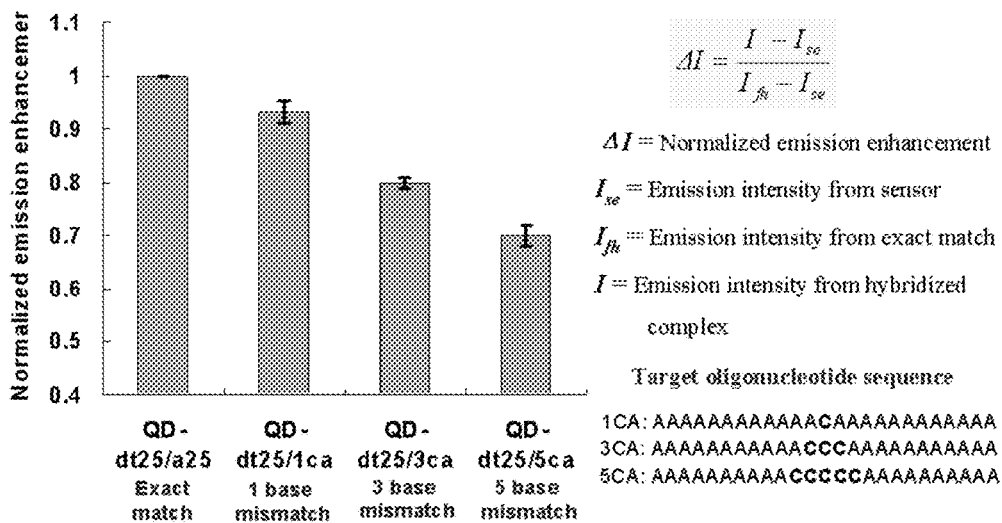

FIG. 7. Normalized emission intensity difference plot comparing the fluorescence emission of an exactly matched ZnSeQD-DT25dA25 hybridized complex to three additional hybridized complexes that contain a mismatch of 1, 3, or 5 base(s) in the middle section of the target sequence.

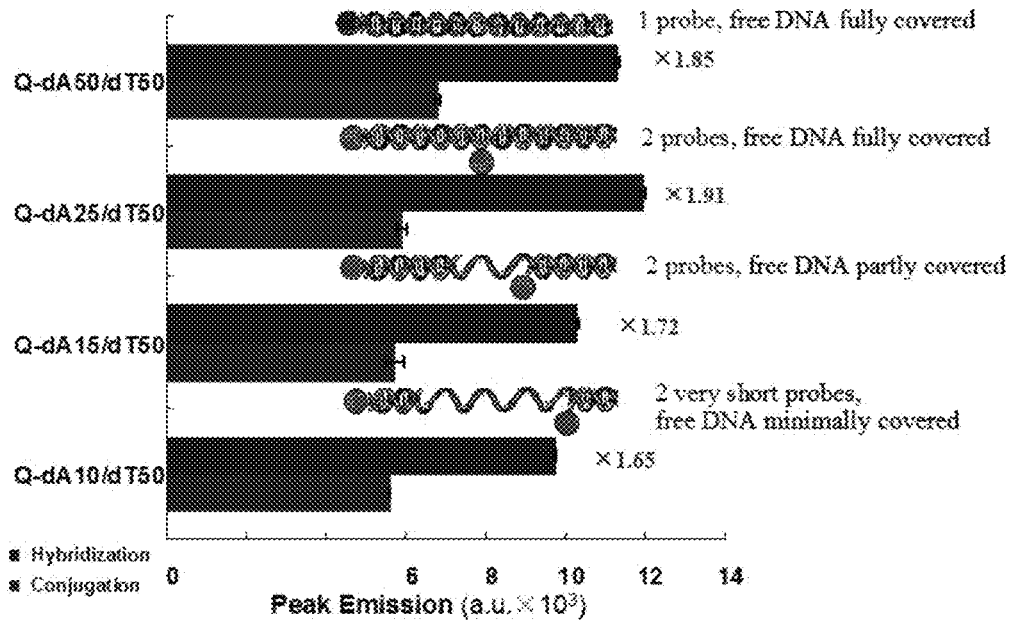

FIG. 8. Structure-dependent fluorescence emission amplification from QD-DNA hybridized complexes using a "long" target (dT50) and two "short" probes. The results from hybridization with a complementary single probe are also included as reference.

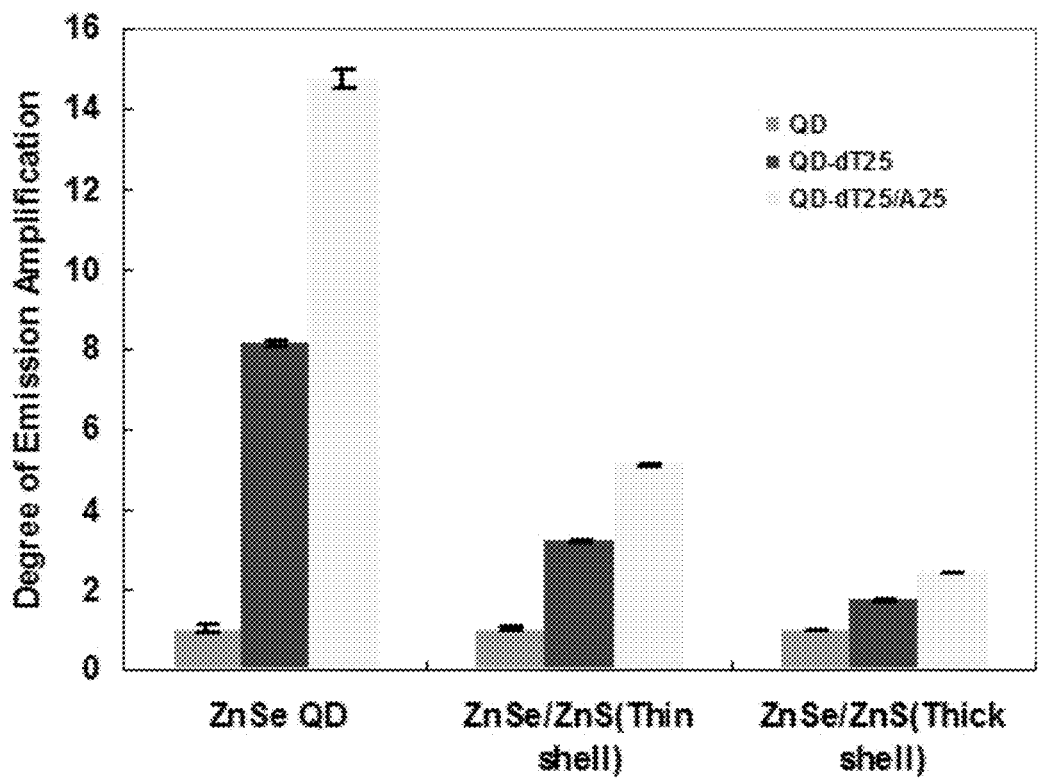

FIG. 9. Fluorescence emission amplification of MUA-capped ZnSe and ZnSe/ZnS core-shell QDs after conjugation with dT25 at 1:1 particle to biomolecule ratio and after hybridization of the QD-dT25 sensor with free dA25. The ZnSe QDs without a shell exhibit the strongest emission amplification. The fluorescence emission amplification becomes progressively smaller as the thickness of the shell increases. The data shown corresponds to two ZnS shell thicknesses: 0.3nm and 0.9nm.

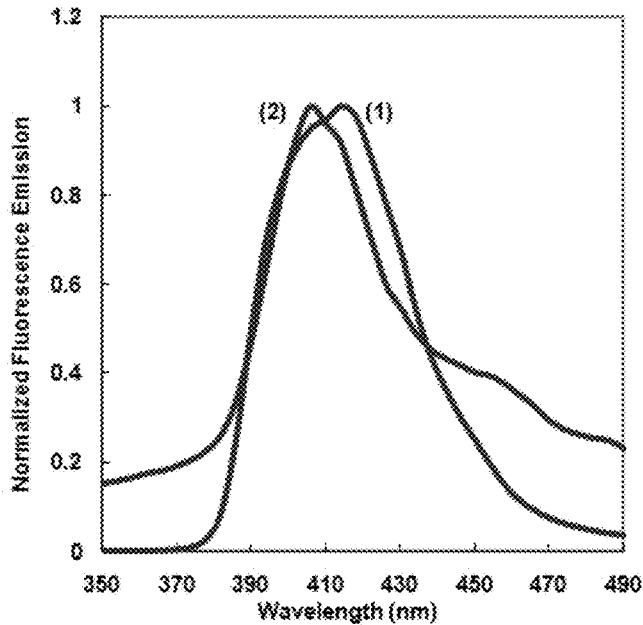
FIG. 10. Normalized fluorescence emission spectra of (1) HDA/TOP-capped ZnSe QDs dispersed in butanol and (2) MUA-capped ZnSe QDs dispersed in PBS.
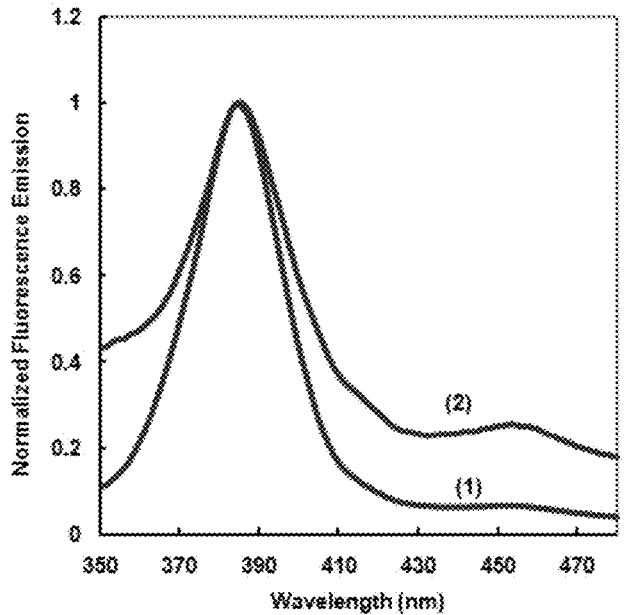
FIG. 11. Normalized fluorescence emission spectra of (1) TOPO/TOP-capped (ZnSe)ZnS core-shell QDs dispersed in butanol and (2) MUA-capped (ZnSe)ZnS core-shell QDs dispersed in PBS.

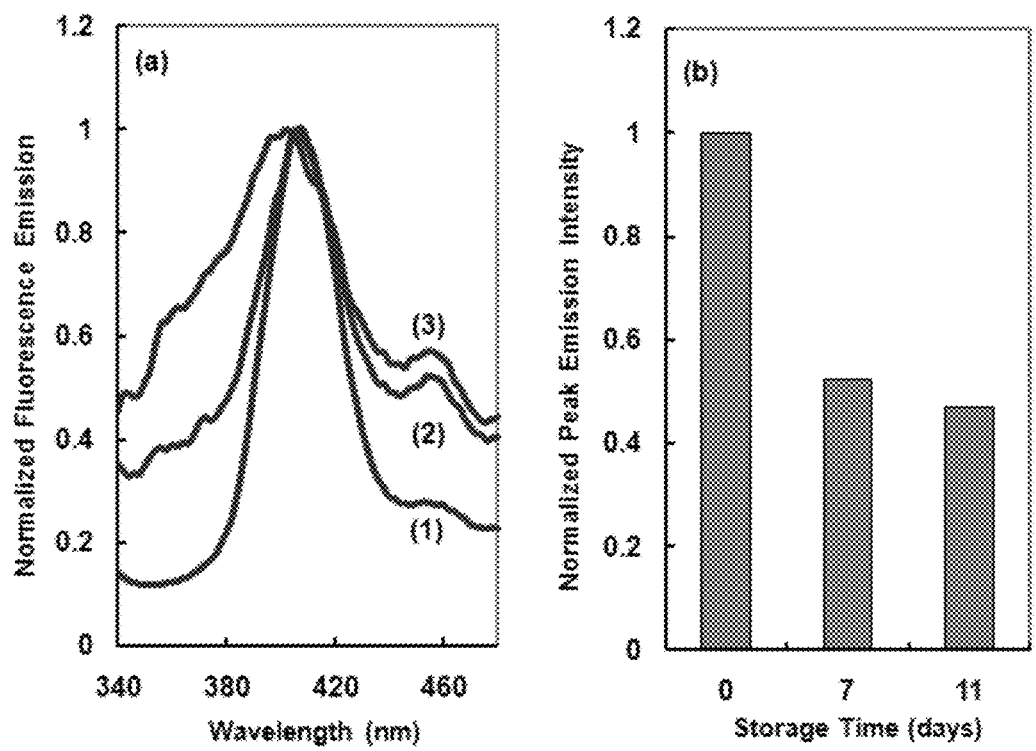
FIG. 12. Stability of MUA-capped aqueous dispersions ZnSe QDs in PBS. (a) Normalized fluorescence spectra of (1) freshly prepared QDs, (2) QDs after 7 days in storage at room temperature, and (3) QDs after 11 days in storage at room temperature. (b) Evolution of QD peak emission intensity vs. time in storage.

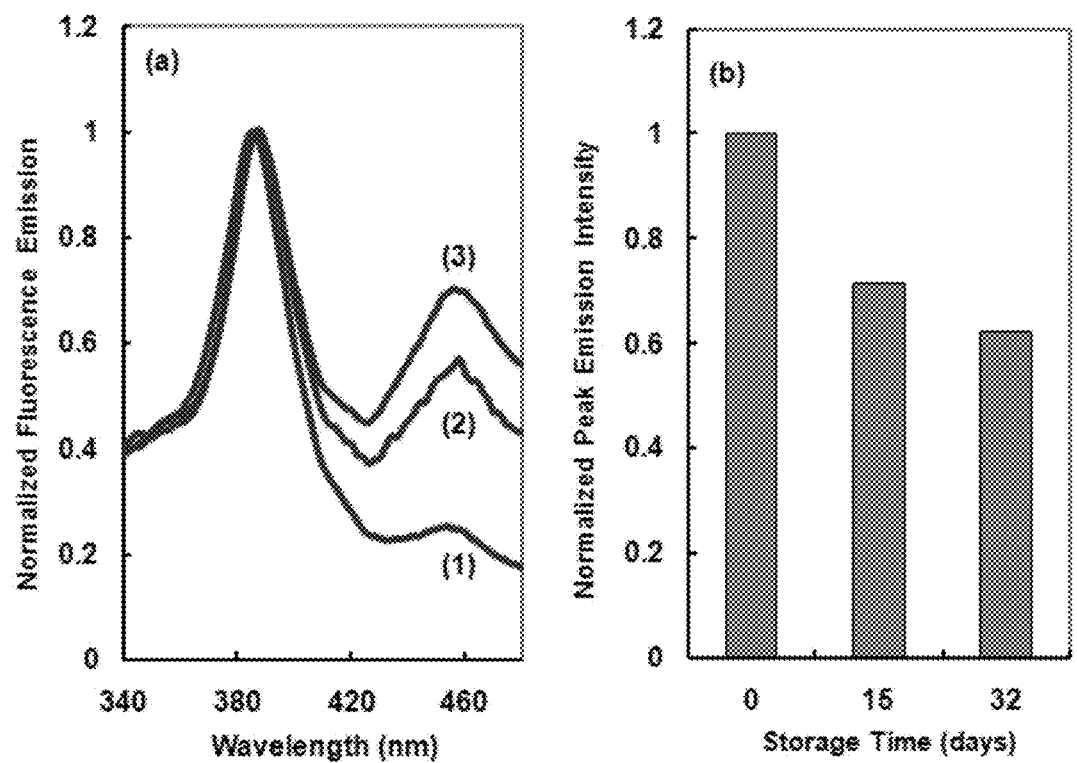
FIG. 13. Stability of MUA-capped aqueous dispersions of (ZnSe)ZnS core-shell QDs in PBS. (a) Normalized fluorescence spectra of (1) freshly prepared QDs, (2) QDs after 15 days in storage at room temperature, and (3) QDs after 32 days in storage at room temperature. (b) Evolution of QD peak emission intensity vs. time in storage.

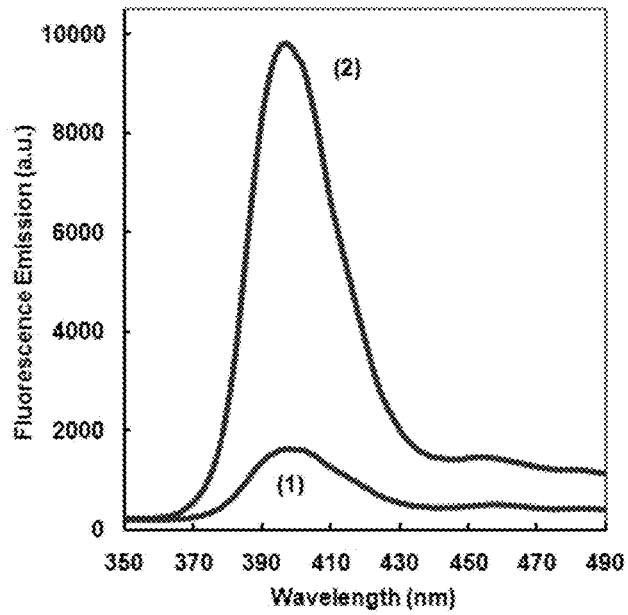

FIG. 14. Comparison of fluorescence emission spectra of (1) MUA-capped ZnSe QDs in PBS and (2) the same QDs following conjugation to an oligonucleotide with 25 base pair of adenine (dA25) indicates that conjugation of QDs to dA25 caused an increase in peak emission intensity.

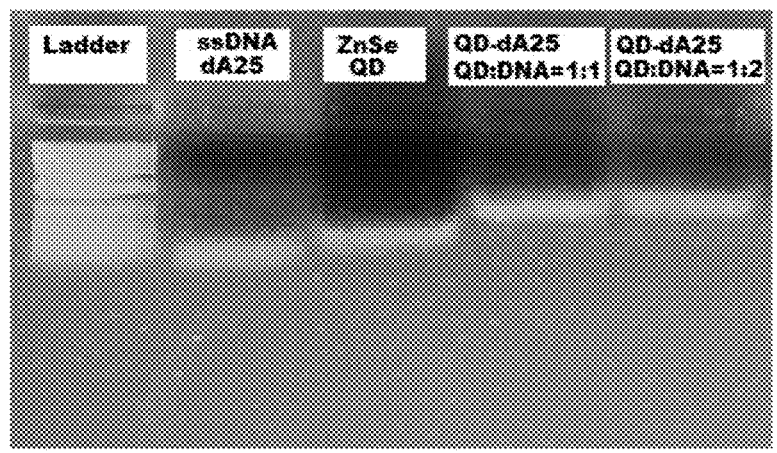

FIG. 15. The distinct gel electrophoresis migration pattern of two ZnSe QD-dA25 conjugate formulations compared to free ssDNA (dA25) and plain MUA-capped ZnSe QDs indicates conjugation of QDs to ssDNA.

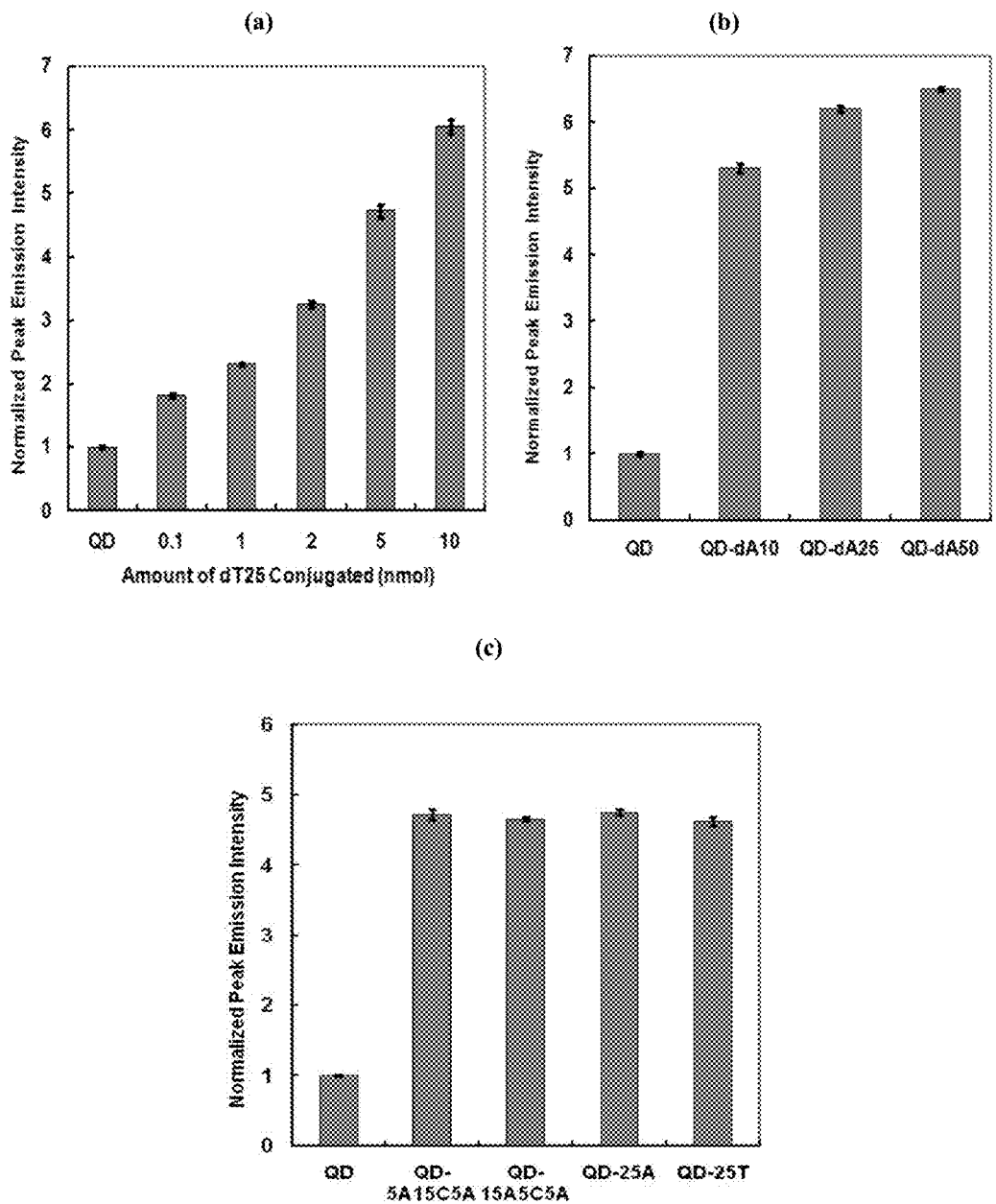
FIG. 16. Peak fluorescence emission intensity of ZnSe QDs conjugated to: (a) increasing amounts of dT25 ssDNA molecules; (b) oligo(dA) molecules of varying length; (c) 25-base ssDNA molecules of varying chemical sequence.

(a)
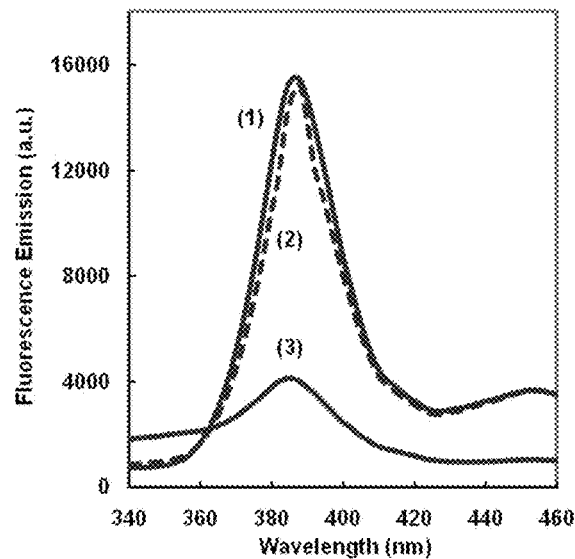
(b)
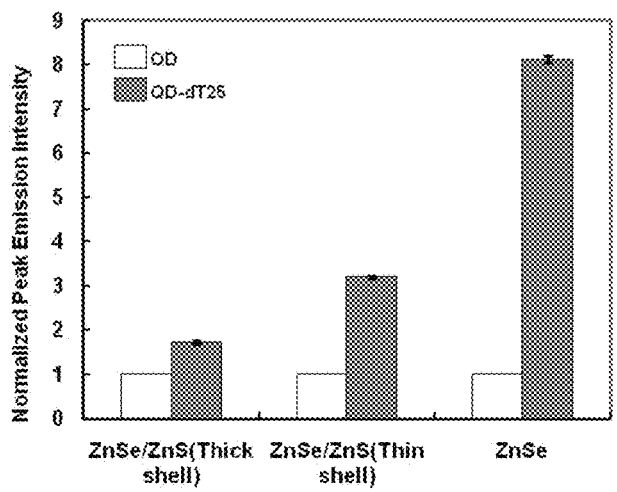
FIG. 17. Fluorescence emission spectra of (ZnSe)ZnS core-shell QDs. (a): After conjugation to (1) dA25 (continuous line), (2) dT25 (dashed line), and (3) prior to ssDNA conjugation. (b): After conjugation to dT25 for two different ZnS shell thicknesses: 0.9 nm (thick shell) and 0.3 nm (thin shell). The size of the ZnSe QD cores was 4nm in all cases.

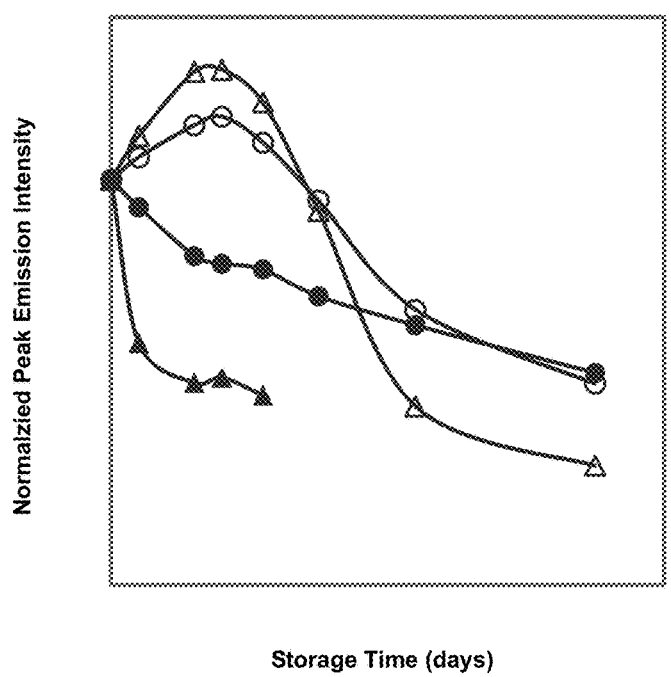
FIG. 18. Evolution of normalized peak emission intensity of QDs and QD-ssDNA conjugates in PBS with time in storage at room temperature; MUA-capped ZnSe QDs (▲); MUA-capped (ZnSe)ZnS core-shell QDs (●); ZnSe QD-dT25 conjugate (△); (ZnSe)ZnS-dT25 conjugate (○).

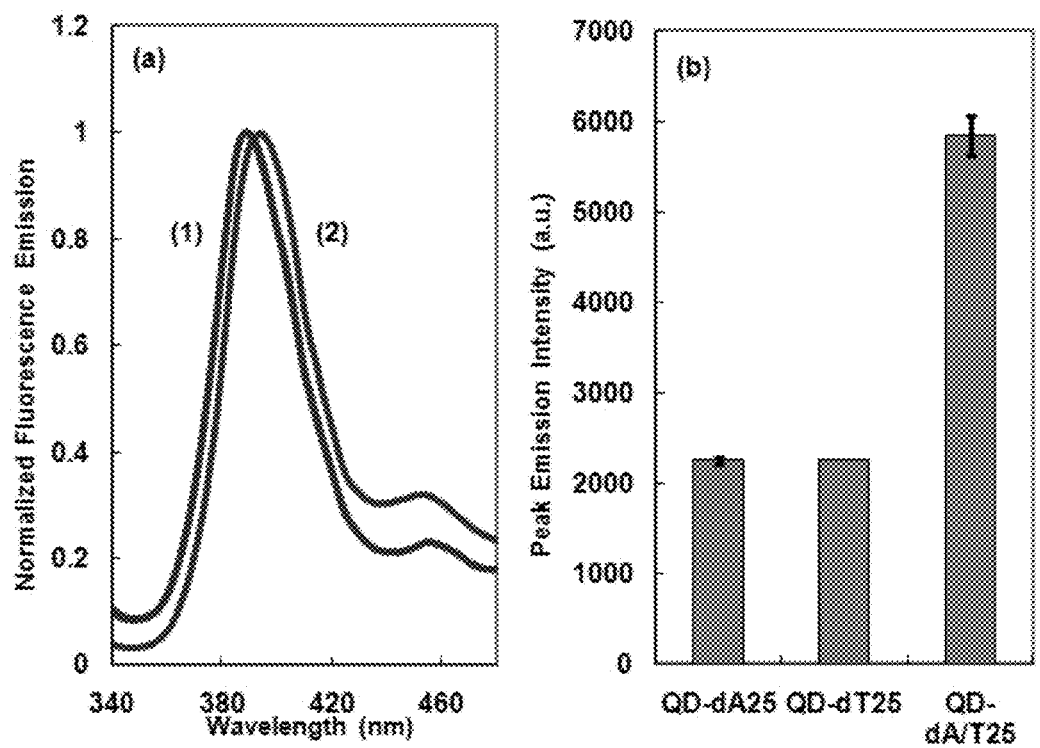
FIG. 19. Effects of DNA hybridization on fluorescence emission of ZnSe QDs conjugated to oligo(dA25) and oligo(dT25). (a) Comparison of normalized emission spectra: (1) QD-dA25 or QD-dT25 (indistinguishable), (2) QD-dAdT25-QD hybridized structure. (b) Comparison of peak emission intensities.

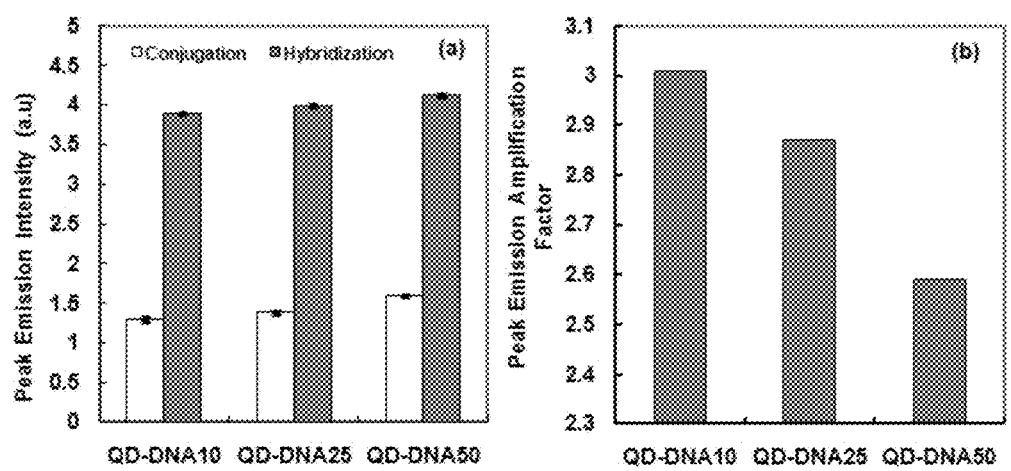

FIG. 20. Effects of DNA length on fluorescence emission of ZnSe QD-dA conjugates after hybridization with ZnSe QD-dT conjugates of equal length. (a) Comparison between the peak emission intensity of QD-ssDNA conjugates and QD-dsDNA-QD hybridized structures. (b) Emission intensity amplification factor after hybridization in comparison to the emission of the corresponding non-hybridized QD-ssDNA conjugate.

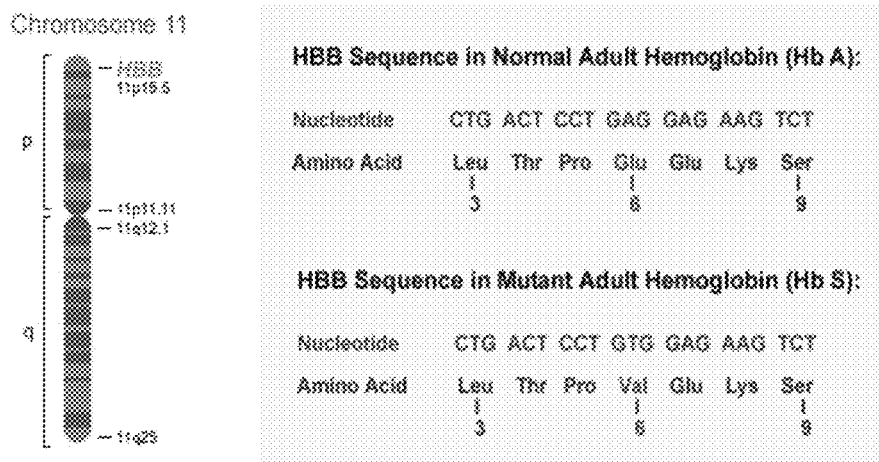
FIG. 21. Location of the HBB gene on the short (p) arm of human chromosome 11 and HBB sequence in normal adult hemoglobin vs. HBB sequence in mutant adult hemoglobin. Source: http://www.ornl.gov/sci/techresources/Human_Genome/posters/chromosome/hbb.shtml
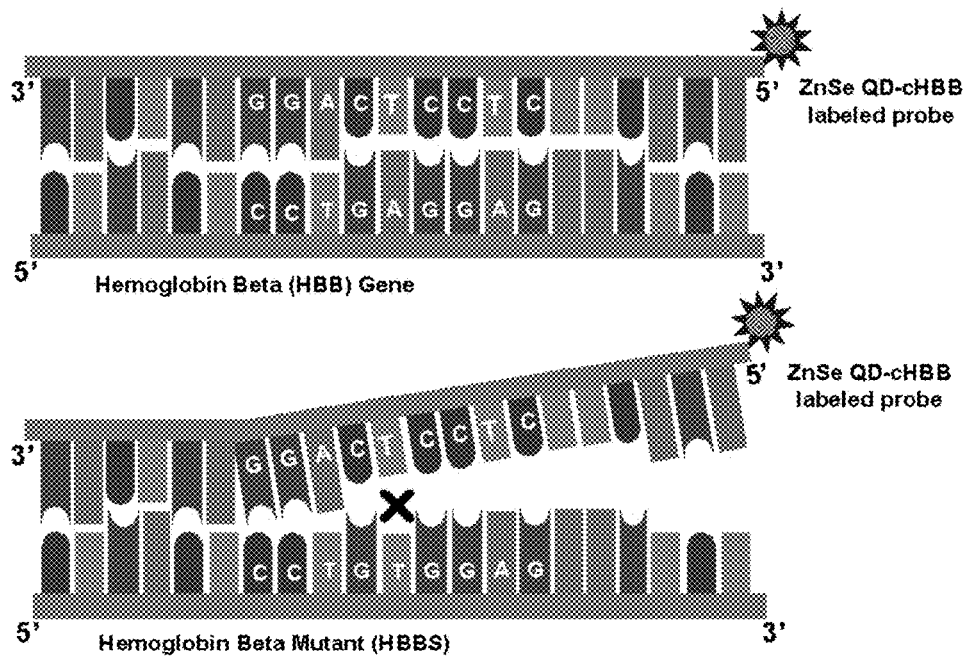
FIG. 22. Schematic of ZnSe QD-cHBB sensor hybridization with normal HBB and mutant (HBBs) targets.

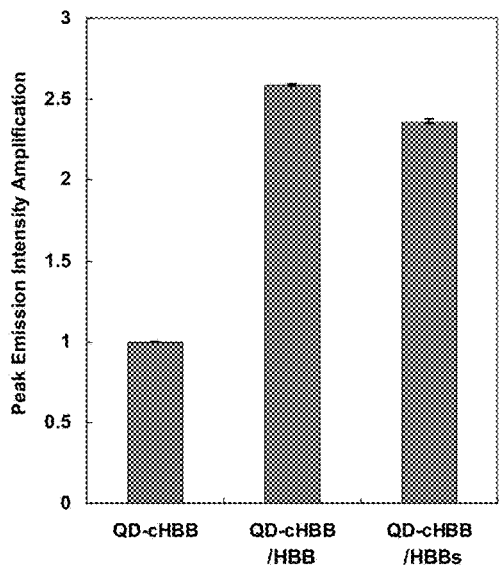

FIG. 23. Peak emission intensity amplification of a ZnSe QD-cHBB sensor after hybridization with HBB and HBBs targets.

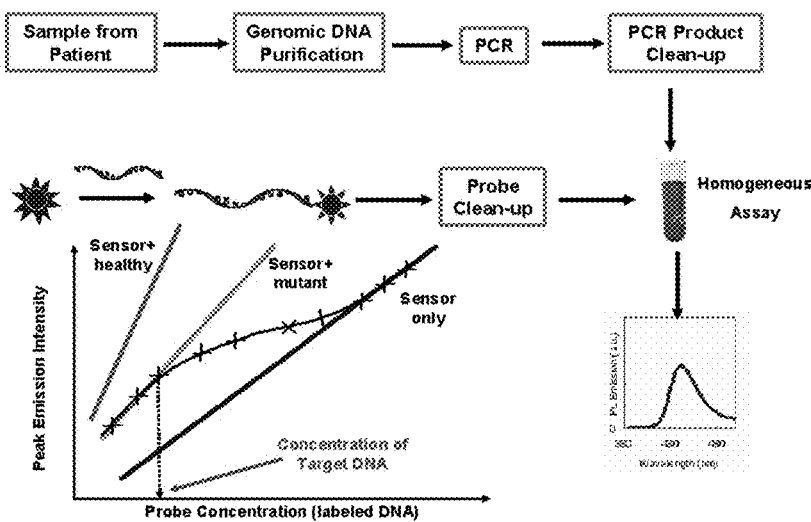

FIG. 24. Schematic showing a procedure for sample preparation and the expected dose response curve of a homogeneous DNA Assay that employs an engineered ZnSe QD-DNA sensor for rapid quantitative detection of DNA mutations. (PCR: Polymerase Chain Reaction)

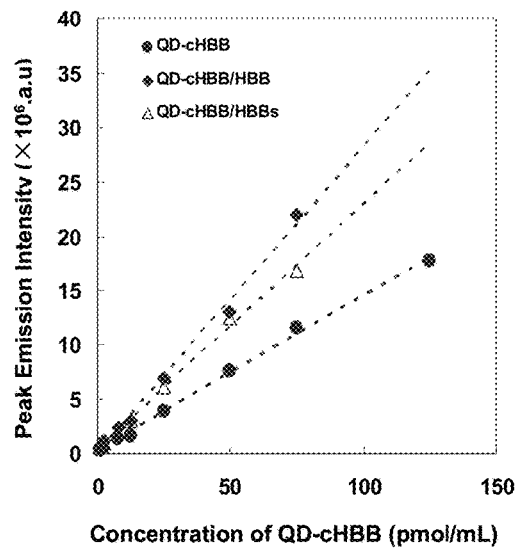

FIG. 25. Calibration lines for a homogeneous assay that uses a ZnSe QD-cHBB sensor to detect free HBB (healthy) or HBBs (mutant) sequences in solution.

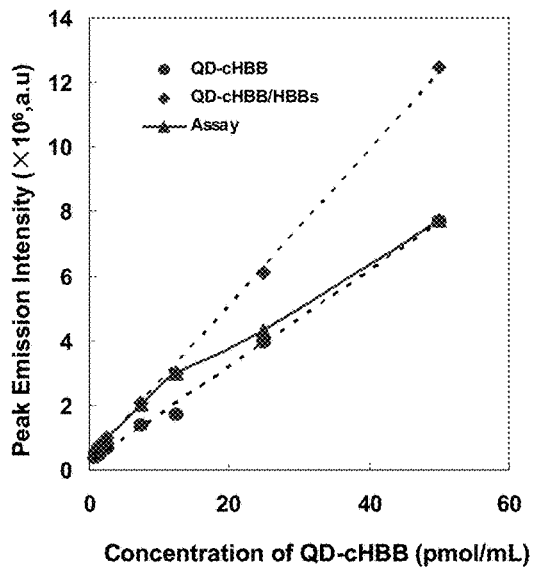

FIG. 26. Homogeneous assay that detects the presence of free HBBs in solution using a ZnSe QD-cHBB sensor. The initial concentration of free HBBs corresponds to the point of departure of the dose response curve of the assay from the QD-cHBB/HBBs calibration line and is equal to 12.5 pmol/mL.

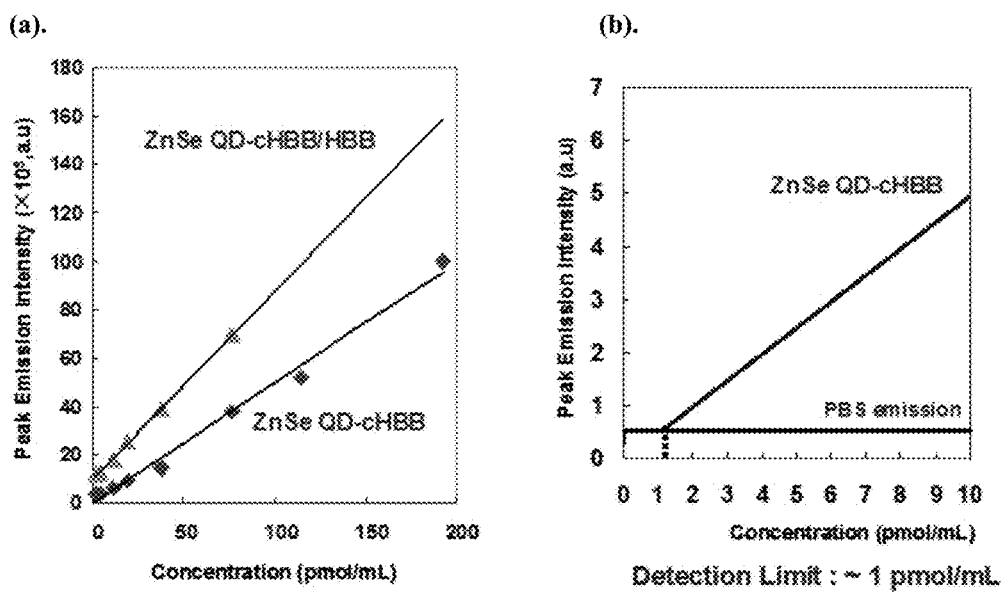

FIG. 27. (a) Fluorescence emission intensity of ZnSe QD-cHBB sensor before and after hybridization for various free DNA (normal HBB sequence) concentrations. (b) The intersection of the sensor intensity vs. concentration line with the PBS buffer emission intensity at the same wavelength provides the detection limit for the sensor and instrument (Horiba Fluorolog-3) combination used in these experiments.

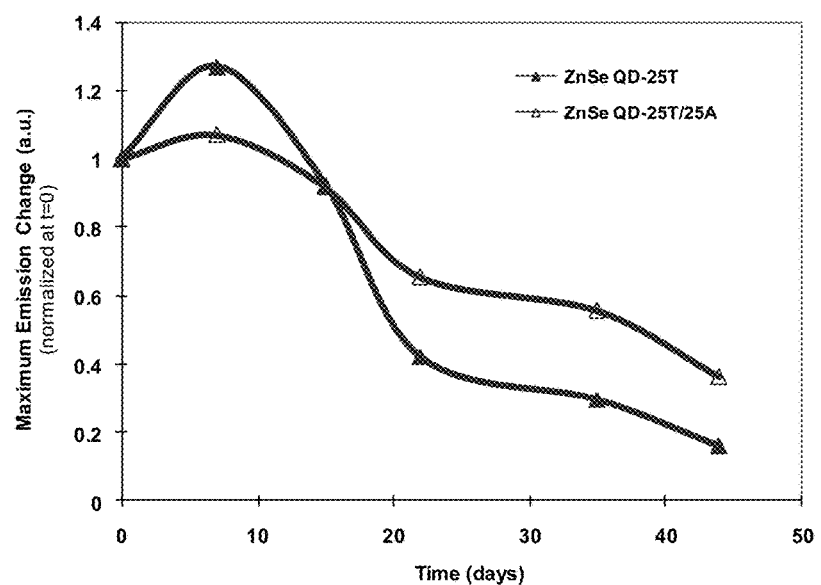
FIG. 28. Evolution of normalized peak emission intensity of QD-ssDNA conjugate and QD-dsDNA hybrid in PBS with time in storage at room temperature. ZnSe QD-dT25 conjugate (▲); ZnSe QD-dT25/dA25 hybrid (△).

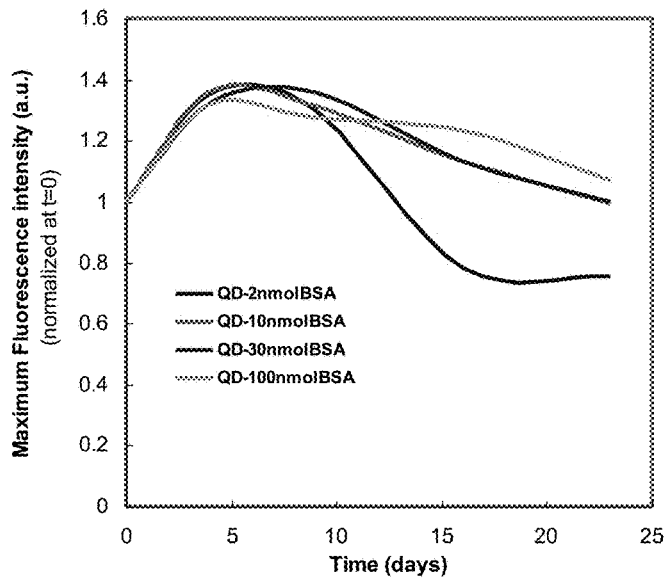
FIG. 29. Fluorescence emission intensity of ZnSe QD-BSA in PBS buffer (ZnSe QDs conjugated with different amounts of BSA at pH=7.723)
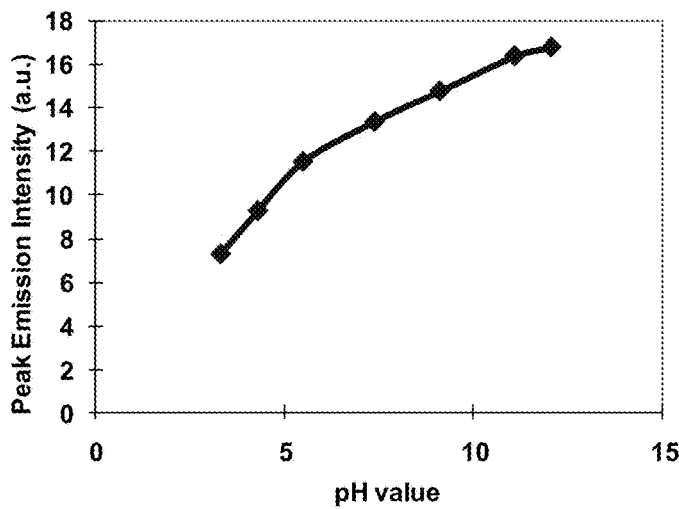
FIG. 30. Fluorescence emission intensity of ZnSe QD-BSA complexes in PBS buffer solution as function of pH.

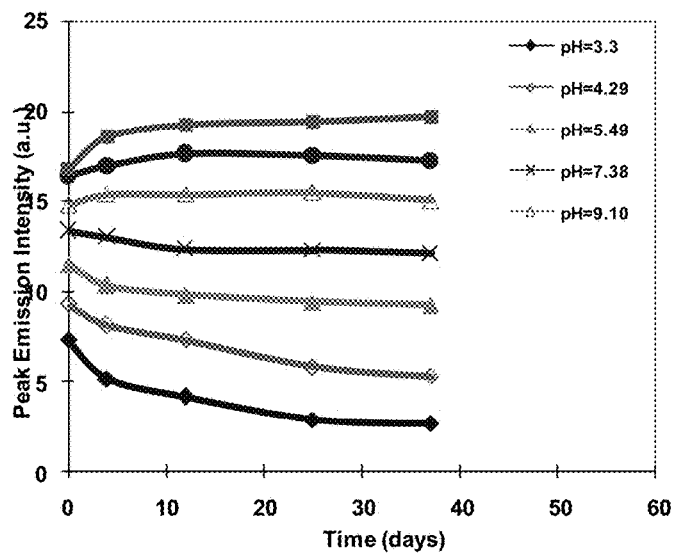

FIG. 31. Fluorescence emission intensity of ZnSe QD-BSA complexes as function of time in storage in PBS buffer solution at various pH values.

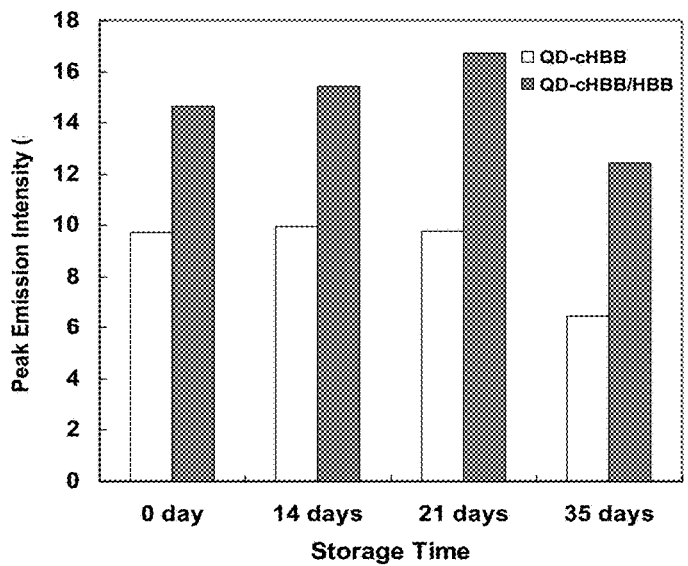

FIG. 32. Peak emission intensity of ZnSe QD-cHBB sensor at different times in storage and comparison to the emission intensity of the corresponding ZnSe QD-dsDNA complex formed after hybridization of the sensor with a complementary ssDNA target.

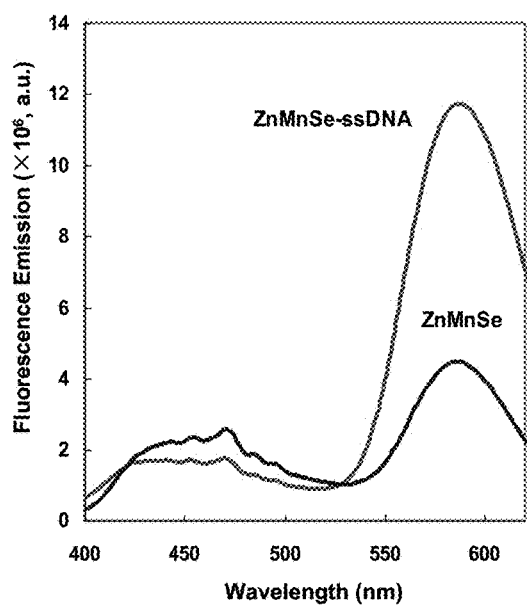
FIG. 33. Comparison of fluorescence emission spectra of MSA-capped Mn-doped ZnSe (ZnMnSe) QDs in PBS and the same QDs following conjugation to ssDNA with 25 base pairs of Ademine (dA25).

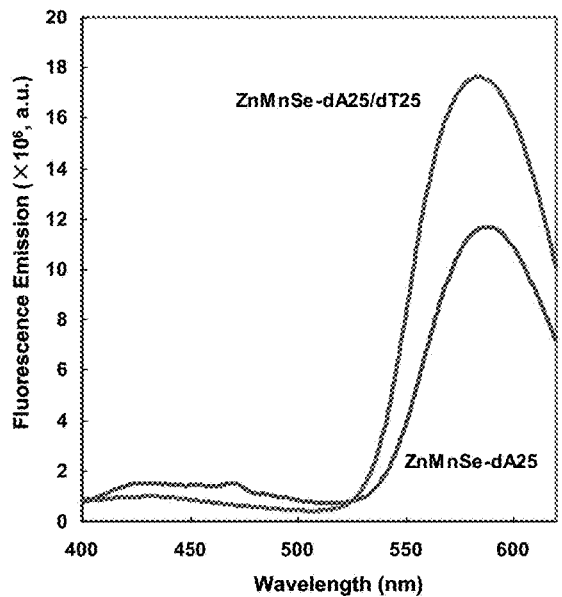
FIG. 34. Fluorescence emission spectrum of Mn-doped ZnSe (ZnMnSe) QD-dA25 conjugate in PBS before and after hybridization with free dT25 ssDNA.
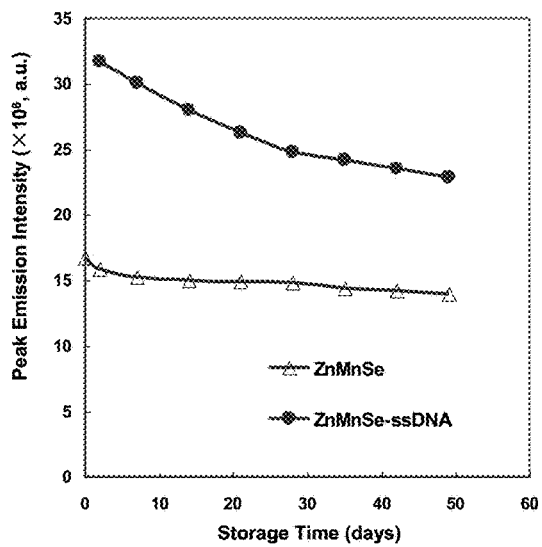
FIG. 35. Peak emission intensity of Mn-doped ZnSe (ZnMnSe) QDs and QD-dA25 conjugates in PBS vs. time in storage at room temperature: MSA-capped ZnMnSe QDs (△); ZnMnSe-dA25 conjugates (●).

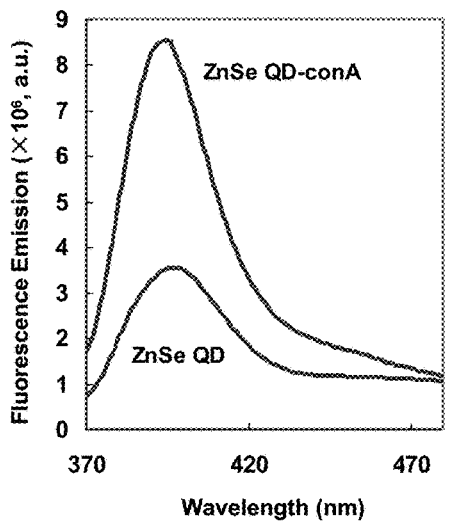
FIG. 36. Fluorescence emission spectra of (1) MUA-capped ZnSe QDs in PBS and (2) QDs from the same stock solution conjugated to concanavalin A.
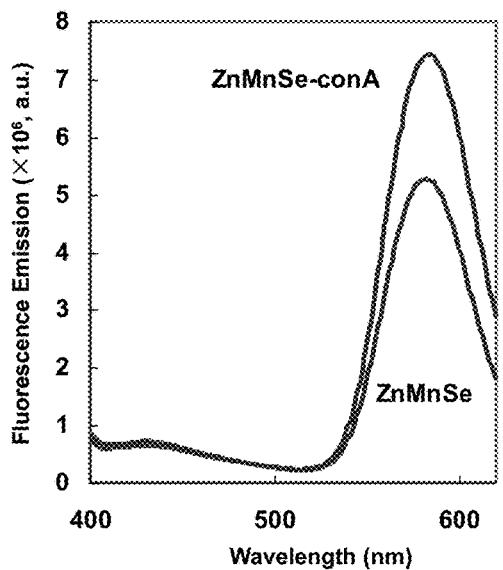
FIG. 37. Comparison of fluorescence emission spectra of (1) MSA-capped Mn-doped ZnSe (ZnMnSe) QDs in PBS and (2) QDs from the same stock solution conjugated to concanavalin A.

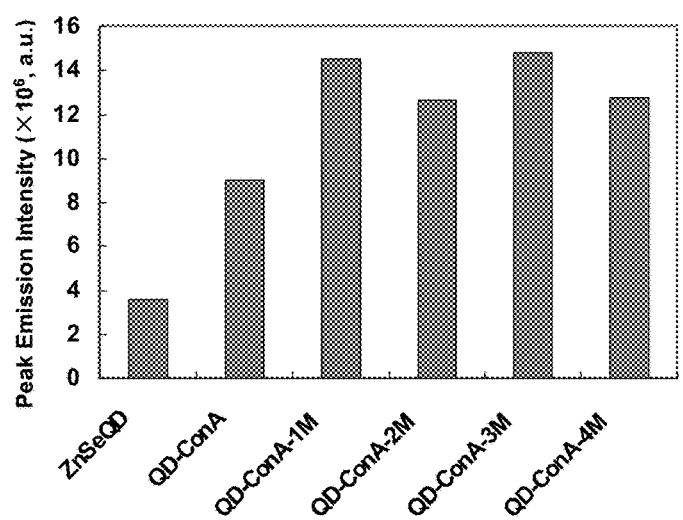
FIG. 38. Fluorescence emission of ZnSe QD-ConA sensors in PBS buffer solution before and after binding with methyl-α-D-mannopyranoside target under conditions of sensor to target molecular ratio equal to 1:1, 1:2, 1:3 and 1:4.

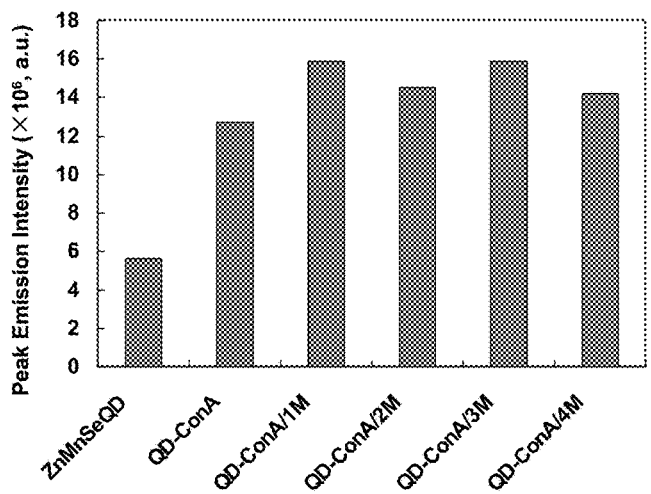

FIG. 39. Fluorescence emission of Mn-doped ZnSe (ZnMnSe) QD-Con A sensor in PBS buffer solution before and after binding with methyl-α-D-mannopyranoside target under conditions of sensor to target molecular ratio equal to 1:1, 1:2, 1:3 and 1:4.

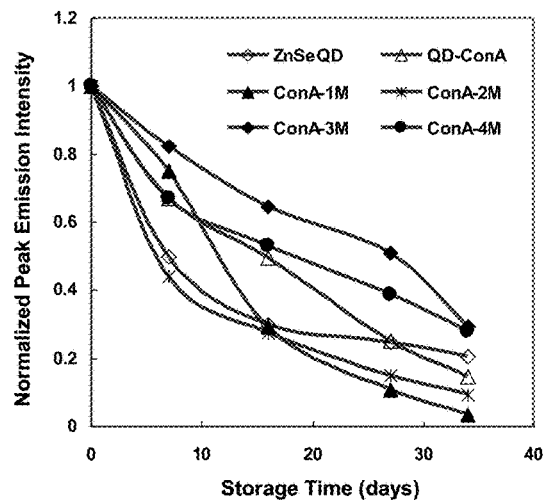

FIG. 40. Normalized peak emission intensity of ZnSe QDs, ZnSe QD-ConA conjugates, and ZnSe QD-ConA/M bound complexes in PBS buffer solution vs. time in storage at room temperature.

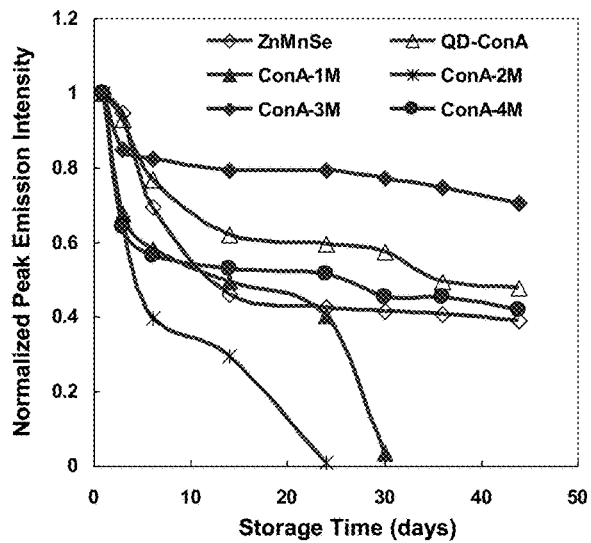
FIG. 41. Evolution of normalized peak emission intensity of Mn-doped ZnSe (ZnMnSe) QDs, ZnMnSe QD-ConA conjugates, and QD-ConA/M complexes in PBS buffer solution with time in storage at room temperature.
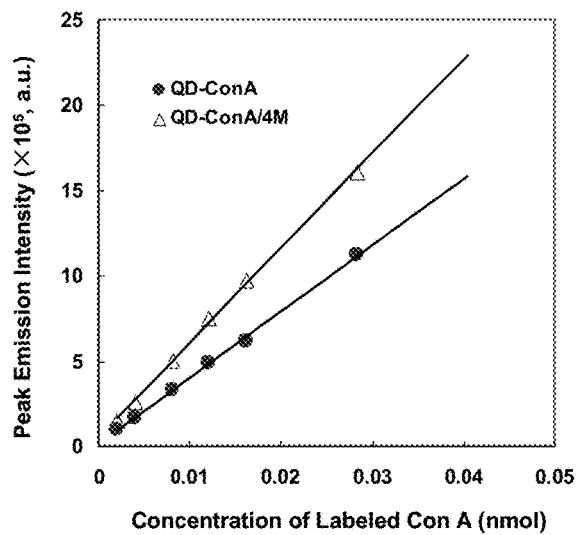
FIG. 42. Fluorescence emission intensity of a ZnSe QD-ConA sensor and the ZnSe QD-Con A/4M bound complex vs. concentration of labeled ConA.

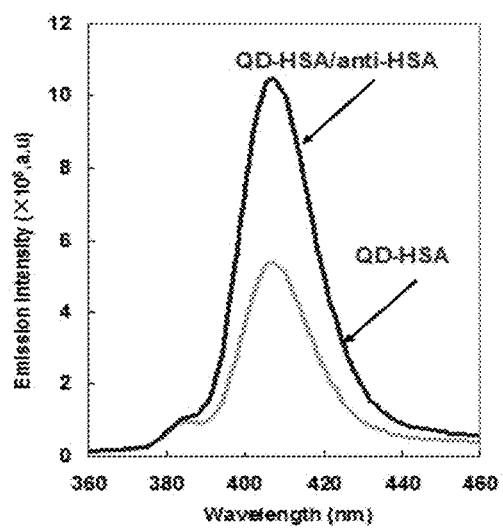
FIG. 43. Emission intensity amplification when a ZnSe QD-HSA labeled antigen binds an anti-HSA antibody (ZnSe QD-HSA concentration: 53 μg/mL).

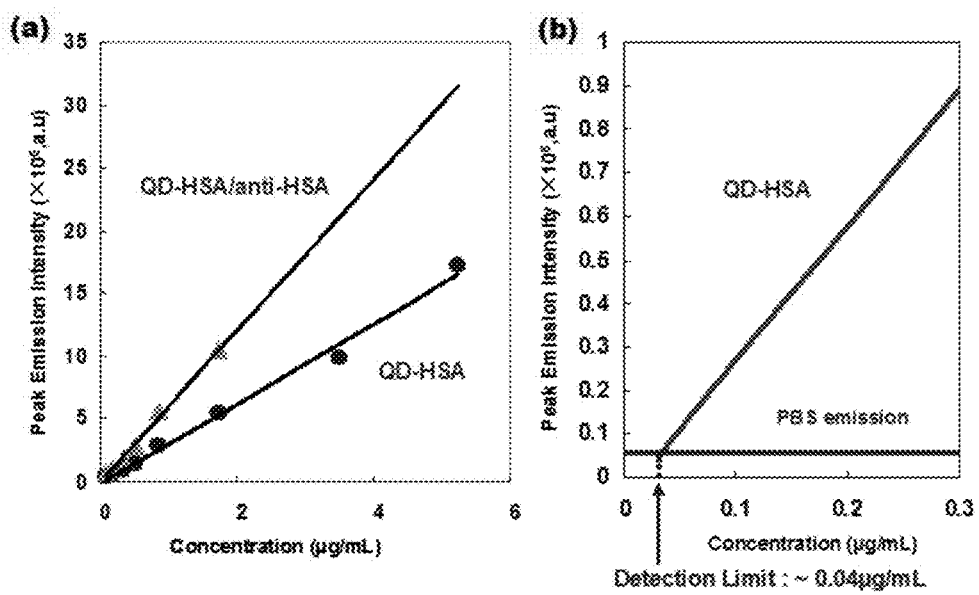
FIG. 44. (a) Fluorescence emission intensity of the ZnSe QD-HSA labeled antigen and the ZnSe QD-HSA/antiHSA bound complex plotted as function of concentration. (b) Low concentration range of the same plot as in (a) showing the ZnSe QD-HSA fluorescence emission intensity and the PBS buffer solution emission intensity at the same emission wavelength.

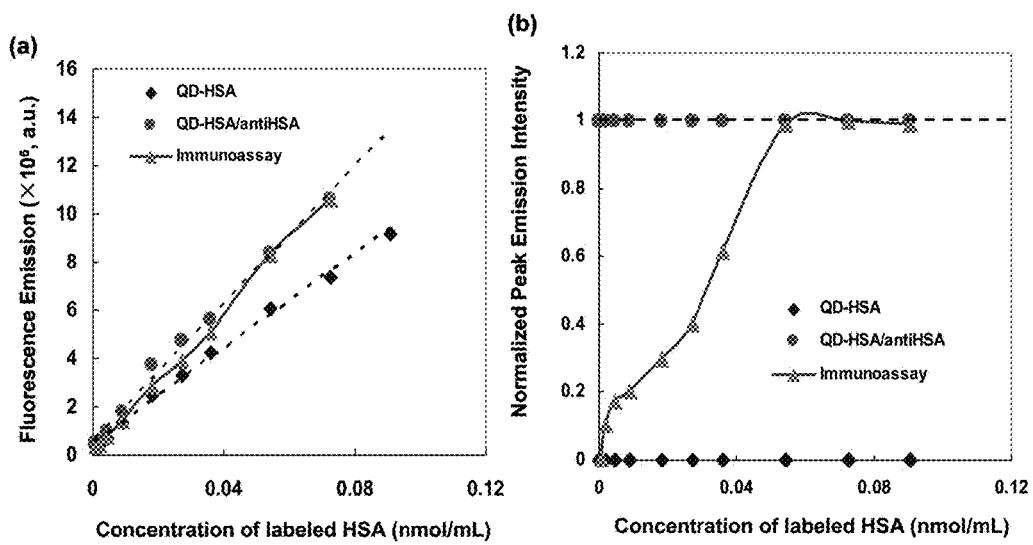
FIG. 45. (a) Competitive immunoassay that detects the presence of free HSA in human serum plasma by progressively dosing the sample with ZnSe QD-HSA labeled antigen and anti-HSA antibody. (b) Normalized QD fluorescence emission intensity vs. labeled HSA concentration corresponding to the competitive immunoassay.

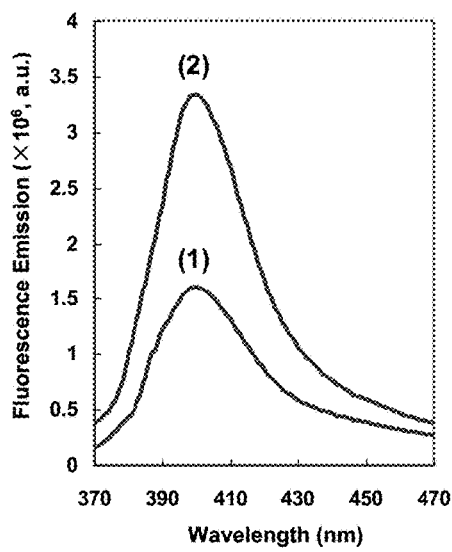
FIG. 46. Emission intensity of (1) ZnSe QD-antiFGF sensor and (2) ZnSe QD-antiFGF /FGF bound complex.
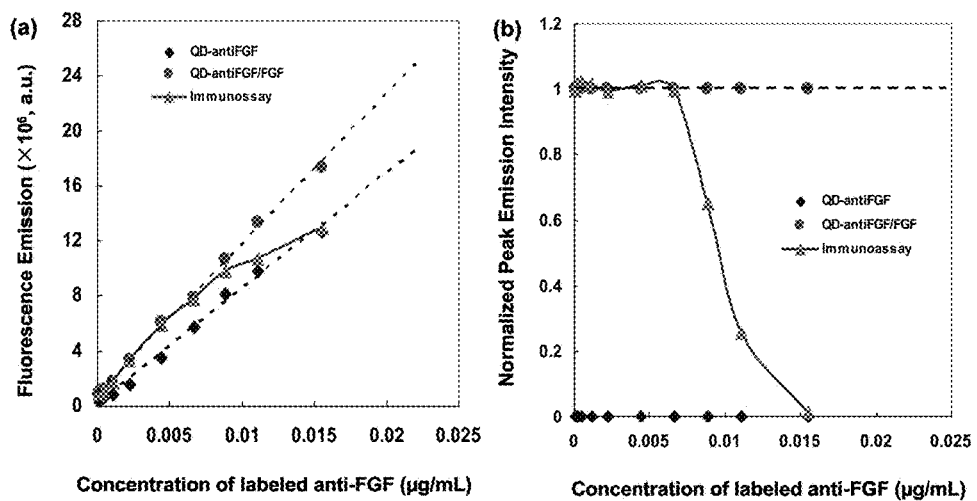
FIG. 47. (a) Direct immunoassay that detects the presence of free FGF in PBS solution by progressively dosing the sample with a ZnSe QD-antiFGF sensor; (b) Normalized fluorescence intensity plot for the direct immunoassay.

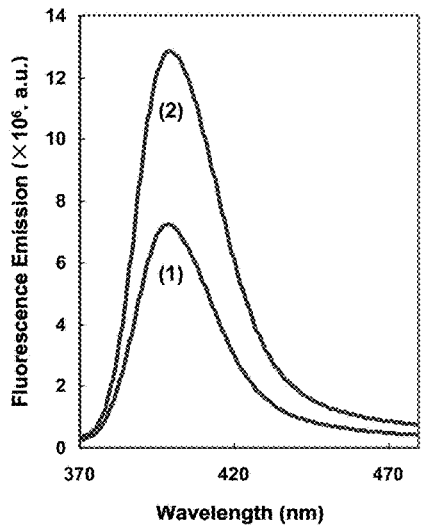
FIG. 48. Emission intensity of (1) ZnSe QD-antiPSA sensor and (2) ZnSe QD-antiPSA/PSA bound complex.
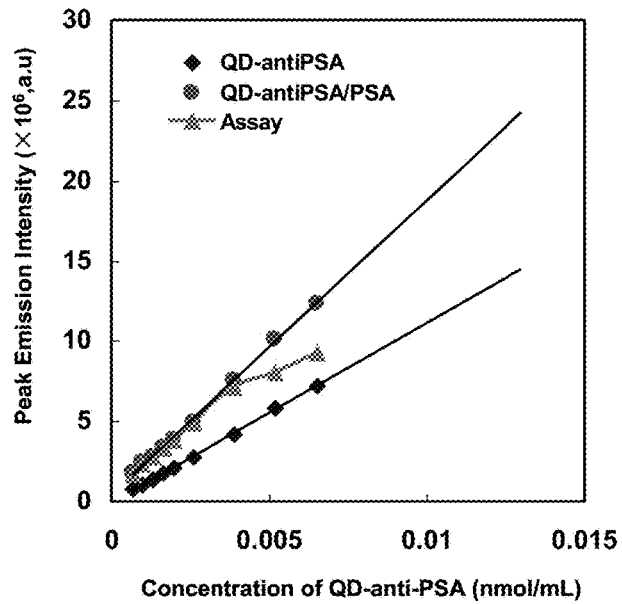
FIG. 49. Direct immunoassay that detects the presence of free PSA in PBS solution by progressively dosing the sample with ZnSe QD-antiPSA sensor.

FIG. 50. Normalized fluorescence intensity for a direct immunoassay that detects the presence of free *C. trachomatis* antigen in PBS solution by progressively dosing the sample with ZnSe QD-antiCTA sensor solution.

FIG. 51. Comparison of fluorescence emission amplification from QD-anti-HSA and QD-anti-FGF sensors. The QD-anti-FGF sensor exhibits higher intensity amplification and is a more suitable antibody-based sensor for a regular (non-competitive) homogeneous assay that detects FGF in solution.

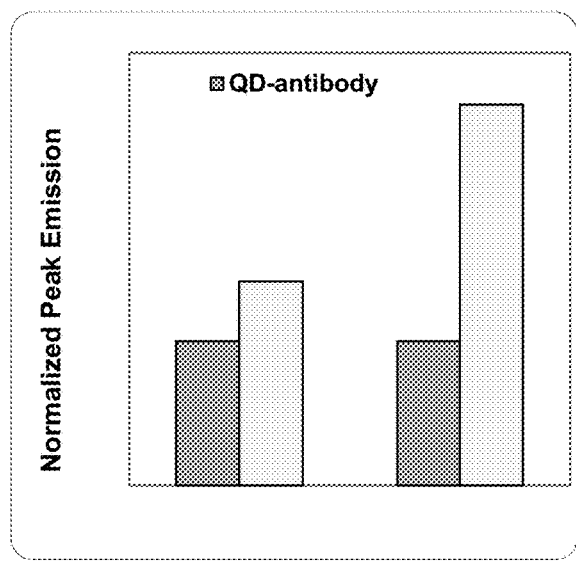
FIG. 52. Comparison of fluorescence emission amplification by comparing QD-anti-HSA vs. QD-anti-HSA/HSA, and QD-anti-FGF vs. QD-anti-FGF/FGF. The QD-anti-FGF sensor exhibits higher intensity amplification upon binding to free FGF in solution and is a more suitable antibody-based sensor for a regular (non-competitive) homogeneous assay that detects FGF in solution.

QUANTUM DOT-BASED OPTICAL SENSORS FOR RAPID DETECTION AND QUANTITATIVE ANALYSIS OF BIOMOLECULES AND BIOLOGICAL MATERIALS

TECHNICAL FIELD OF THE INVENTION

The invention generally relates to detection and analysis of biological materials. More particularly, the invention relates to quantum dot-based optical sensors and methods for rapid detection and quantitative analysis of various biomolecules and biological materials, such as nucleic acids, proteins, cells, etc.

BACKGROUND OF THE INVENTION

Use of fluorescent labels in biodetection has revolutionized how research scientists detect, analyze, and quantify biological materials and systems. Fluorescent labels emit light upon excitation by an external energy source. Fluorescent labels have a number of applications in biology including, for example, fluorescence flow cytometry, fluorescence-activated cell sorting, fluorescence microscopy, and fluorescence immunoassays. Semiconductor nanocrystals, known as Quantum Dots (or "QDs"), have emerged over the past twenty years as an interesting class of nanomaterials with optical properties that have potential applications in a variety of fields, including biological imaging and detection, (Alivisatos 1996 *Science*, Vol. 271, no. 5251, pp, 933-937; Murray, et al 2000 *Annu. Rev. Mat. Sci.,* 30:545-310.) QDs have been used as fluorescent tags and have shown unique properties in comparison to common fluorophores for applications in biological imaging and diagnostics. (Michalet, et al. 2005 *Science*: Vol. 307. no. 5709, pp. 538-544.) A common type of semiconductor QDs is CdSe, which is typically grown with a ZnS shell, for example, as a CdSe—ZnS core-shell structure. (Hines, et al. 1996 *J. Phys. Chem.* 100 (2), pp 468-471.) To protect the core and to increase the quantum yield of the QDs (i.e., the fluorescence emission intensity), QDs have been capped with a shell that has a larger band gap than the core, such as in CdSe—ZnS core-shell structures.

Despite the progress in biodetection in recent years, significant constraints exist that limit the applicability of fluorophore labels. Existing systems suffer from significant shortcomings, such as lack of sufficient sensitivity, complexity of system or operation, lengthy data collection and analysis, insufficient selectivity or specificity, requirement of special equipment or set up, and high cost of instruments and/or operation.

The toxicity of the $Cd^{2+}$ ions is a limiting factor for in vivo applications of Cd-containing QDs and a concern for commercial manufacturing of Cd-based nanocrystals. (Kirchner, et al. 2005 *Nano Letters* 5 (2):331-338.) As a result, "Cd-free" QDs based on ZnSe have attracted attention, because they do not involve a heavy metal ZnSe-QDs can be grown by a variety of techniques and exhibit size-tunable emission wavelength over a region m the UV-blue part of the spectrum (370-460 nm), which is narrower when compared to the spectral range of CdSe QDs (470-650 nm). (Leppert, et al 1997 *Philosophical Magazine Letters* 75 (1):29-33; Hines, et al. 1998 *J. Phys. Chem. B* 102 (19): 3655-3657; Quinlan, et al. 2000 *Langmuir* 16 (8):4049-4051; Sarigiannis, et al. 2002 *Applied Physics Letters* 80 (21):4024-4026; Karanikolos, et al. 2004 *Langmuir* 20 (3): 550-553; Karanikolos, et al. 2005 *Nanotechnology* 16 (10): 2372-2389; Karanikolos, et al. 2006 *Nanotechnolgy* 17 (13):3121-3128; Pradhan, et al. 2005 *J. Am. Chem. Soc.* 127 (50):17586-17587.)

Doping of ZnSe QDs with transition metals ions, such as $Mn^{2+}$ enables timing of their emission to longer wavelengths, thus providing the ability to develop multi-color probes for biological tagging applications and magneto-optical materials for spintronics. (Pradhan, et al. 2007 *J. Am. Chem. Soc.* 129 (11):3339-3347; Pradhan, et al. 2007 *Nano Letters* 7 (2):312-317; Erwin, et al. 2005 *Nature* 436 (7047): 91-94; Norris, et al. 2001 *Nano Letters* 1 (1):3-7.)

There is therefore an unmet need for improved biodetection sensors, systems, and methods that allow efficient, effective and low cost fluorescent imaging and diagnostic applications.

SUMMARY OF THE INVENTION

The invention is based in part on semiconductor nanocrystal-based sensors and related systems and methods that are useful for various applications in the detection of biological materials. In particular, the invention provides semiconductor nanocrystal (QD-based) optical sensors and methods for direct, rapid and accurate detection and analysis of various biomolecules and materials, such as nucleic acids, proteins, cells, etc. The invention describes a unique, direct, rapid and accurate method for detection and quantitative analysis of biological materials and biomolecular processes by monitoring and analyzing changes in the fluorescence emission spectra of the QD-based sensors before and after binding with target biological materials.

In one aspect, the invention generally relates to an optical bimolecular sensor for detecting a target biological material. The sensor includes: (a) an inorganic semiconductor nanocrystal capable of fluorescing at a pre-selected wavelength range upon excitation, wherein the semiconductor nanocrystal has a surface allowing aqueous solubility of the semiconductor nanocrystal; (b) a biomolecular probe having an affinity to the target biological material; and (c) a linkage moiety associated with the semiconductor nanocrystal and with the biomolecular probe such that binding of the biomolecular probe with the target biological material results in an optically detectable change in the fluorescence emission spectrum of the semiconductor nanocrystal without employing a second fluorophore other than the semiconductor nanocrystal.

In some preferred embodiments, a single biomolecular probe is linked to a single semiconductor nanocrystal.

The change in the fluorescence emission spectrum of the semiconductor nanocrystal may be a change in the fluorescence emission intensity, a change in the blinking rate of the emitted light, or a shift in the peak emission wavelength, for example. In some preferred embodiments, the semiconductor nanocrystal is single crystalline ZnSe, which has a particle size from: about 1 nm to about 9 nm (e.g., from about 1 nm to about 7 nm; from about 1 nm to about 5 nm; from about 1 nm to about 3 nm).

In some more preferred embodiments, the single-crystalline ZnSe has a particle size from about 3 nm to about 6 nm. In certain preferred embodiments, the population of single-crystalline ZnSe nanocrystals is either monodisperse with particle sizes that deviate less than about 10% in root mean square diameter or polydisperse with particle sizes that deviate more than about 10% in root mean square diameter.

In certain embodiments, the semiconductor nanocrystal is single crystalline ZnSe doped with ions selected from the group consisting of $Cr^{2+}$, $Mn^{2+}$, $Fe^{2+}$, $Co^{2+}$, $Ni^{2+}$, and $Cu^{2+}$.

The semiconductor nanocrystal may be single-crystalline and includes elements from groups II and VI of the periodic table, for example, selected from ZnSe, ZnS, ZnTe, CdSe, CdS, CdTe, HgTe, and ternary and quaternary mixtures of the component elements thereof.

The semiconductor nanocrystal may be single-crystalline and includes elements from groups III and V of the periodic table, for example, selected from GaAs, GaN, GaP, GaSb, AlAs, AlN, AlP, AlSb, InAs, InP, InSb, and ternary and quaternary mixtures of the component elements thereof.

The semiconductor nanocrystal may be single-crystalline and includes elements from groups IV and VI of the periodic table, for example, selected from PbS, PhSe, PbTe, SnTe, and ternary and quaternary mixtures of the elements thereof.

The semiconductor nanocrystal may be single-crystalline and includes elements from, group IV of the periodic table, for example, Si or Ge.

In some embodiments, the semiconductor nanocrystal consists of a single-crystalline core and an inorganic shell made of a material, with wider band gap than the core material and wherein the inorganic shell is sufficiently thin to allow detectable changes in the fluorescence emission spectrum of the single-crystalline core. The single-crystalline core may be a single-crystalline ZnSe or CdSe nanocrystal and the shell is ZnS. For example, the single-crystalline core may have a diameter from about 1 nm to about 9 nm and the inorganic shell has a thickness from one monolayer to about 1 nm.

In some embodiments, the surface of the semiconductor nanocrystal is capped by organic bi-functional, molecules, wherein the organic bi-functional molecules have a moiety at one end of a hydrocarbon chain that allows them to be covalently bound to the nanocrystal surface and a hydrophilic moiety at the other end of the hydrocarbon chain that allows aqueous solubility and conjugation to a biomolecular probe.

The organic bi-functional molecules may be selected from the group consisting of: mercaptocarboxylic acids $HS(CH_2)_nCOOH$, mercaptoalcohols $HS(CH_2)_nOH$, aminocarboxylic acids $H_2N(CH_2)_nCOOH$, thiolamines $HS(CH_2)_nNH_2$, or aminoalcohols $H_2N(CH_2)_nOH$, wherein each n is independently an integer from about 2 to about 20 (e.g., from about 2 to about 15, from about 2 to about 10 from about 2 to about 7, from about 2 to about 5). The hydrocarbon chains are linear or branched. The surface of the semiconductor nanocrystal may be capped by organic multi-functional molecules, wherein the organic multi-functional molecules are selected from the group consisting of: dihydrolipoic acid (DHLA) $HSCH_2CH_2CH(SH)(CH_2)_4COOH$, hydroxy-terminated DHLA-polyethylene glycol (PEG) $HSCH_2CH_2CH(SH)(CH_2)_4CONH(CH_2CHO)_nCH_2CH_2OH$; amine-termined DHLA-PEG $HSCH_2CH_2CH(SH)(CH_2)_4CONH(CH_2CHO)_nCH_2CH_2OH$; carboxylic acid-terminated DHLA-PEG $HSCH_2CH_2CH(SH)(CH_2)_4CONH(CH_2CHO)_nCH_2CH_2COOH$, wherein each n is independently an integer from about 5 to about 15 (e.g., from about 5 to about 12, from about 5 to about 10, from about 5 to about 7).

In some embodiments, the pre-selected wavelength range may be from about 375 nm to about 450 nm when the semi conductor nanocrystal is ZnSe having a diameter from about 1 nm to about 9 nm. In some embodiments, the pre-selected wavelength range is from about 480 nm to about 640 nm when the semiconductor nanocrystal is CdSe having diameter from about 2 nm to about 7 nm.

In certain embodiments, the pre-selected wavelength is about 585 nm when the semiconductor nanocrystal is manganese-doped ZnSe (ZnSe:Mn) having a diameter from about 1 nm to about 9 nm. In certain, embodiments, the pre-selected wavelength is about 540 nm when the semiconductor nanocrystal is copper-doped ZnSe (ZnSe:Cu) having a diameter from about 1 nm to about 9 nm.

The target biological material may be a single- or double-stranded nucleic acid (e.g., a DNA or RNA). The target biological material may be a protein (e.g., human serum albumin, fibroblast growth factor). The protein may be selected from the group consisting of enzymes, proteases, nucleases, recombinases, integrases, RNA polymerases, DNA polymerase, histases, topoisomerases, helicases, isomerases, estarases, oxidoreductases, acyltransferases, lipases, kinases, phosphatases, hydrolases, lectins, structural proteins, transcription factors, translation factors, protein binding factors, nucleic acid binding factors, small molecule binding proteins, macromolecule binding proteins, growth factors, growth factor receptors, cell surface molecules, cell surface receptors, extracellular matrix, cytokines, cytokine receptors, chemokines, chemokine receptors, serum factors, collagen, elastins, histones, keratines, nuclear receptors, ribosomal proteins, extrachromosomal replicons, chromosomes, chromatin, tubuline, actin, dynein, or kinesins.

The target may be selected from a variety of different biomolecules and biological materials, such as amino acids, oligopeptides, polypeptides, metabolites, sugars, disugars, oligosaccharides, lipids, subcellular structures, subcellular organelles, microtubules, actin filaments or microfilaments, cells, or pathogens, such as bacteria, viruses and prions, etc.

The biomolecular probe may be selected from a variety of biomolecules, such as oligonucleotides, antibodies or antigens, small molecule ligands, or immune receptors (e.g., Toll-like receptors or pattern recognition receptors).

The linkage moiety may be selected from a variety of chemical moieties, such as mercaptocarboxylic acids, mercaptoalcohols, aminocarboxylic acids, thiolamines, or aminoalcohols, with carbon chains that are either linear or branched and consisting of two to twenty carbons. In some embodiments, the linkage moiety is selected from the group consisting of mercaptocarboxylic acids, dihydrolipoic acid, PEG-modified mercaptocarboxylic acids and PEG-modified dihydrolipoic acid.

In another aspect, the invention generally relates to a method for detecting a target biological material. The method includes: (a) providing an aqueous solution of an optical biomolecular sensor comprising an inorganic semiconductor nanocrystal, a biomolecular probe having an affinity to the target biological material, and a linkage moiety associated with the semiconductor nanocrystal and with the biomolecular probe, wherein the inorganic semiconductor nanocrystal is capable of fluorescing at a pre-selected wavelength range upon excitation; (b) contacting the optical, biomolecular sensor with a sample to be tested for the presence of the target biological material; and (c) detecting a change in fluorescence emission intensity of the semiconductor nanocrystal, whereby the change in the intensity indicates the presence of the target biological material. In some preferred embodiments, the method is performed as a direct homogeneous assay.

In certain embodiments, the target biological material includes an antigen and the biomolecule probe comprises an antibody that specifically binds with this antigen.

In certain embodiments, the biomolecular probe includes a natural or synthetic oligonucleotide. The target biological material may be a single- or double-stranded nucleic acid.

In some embodiments, the biomolecular probe may include an amine-modified oligonucleotide complementary to a sequence found in the healthy hemoglobin beta (HBB) gene.

In some embodiments, the biomolecular probe may include an amine-modified oligonucleotide with sequence of 5'-AGACTTCTCCTCAGGAGTCAG and an amine group at the 5' end, which is complementary to a sequence found in the healthy hemoglobin beta (HBB) gene.

In some embodiments, the target, biological material may include an oligonucleotide with sequence of 5'-CTGACTC-CTGAGGAGAAGTCT found in the healthy hemoglobin beta (HBB) gene.

In some embodiments, the biomolecular probe may include an amine-modified oligonucleotide complementary to a sequence found in a mutated hemoglobin beta (HBBs) gene. The hemoglobin beta (HBB) gene may include a single-base mutation wherein the hydrophobic amino acid valine takes the place of a hydrophilic glutamic acid at the sixth amino acid position of the beta-HBB polypeptide chain.

In some embodiments, the target biological material may include an oligonucleotide with sequence of 5'-CTGACTC-CTGTGGAGAAGTCT found in a mutated hemoglobin, beta (HBBs) gene.

In yet another aspect, the invention generally relates to a multiplexed homogeneous assay for detecting target biological materials. The assay includes an aqueous solution of two or more inorganic semiconductor nanocrystals, wherein each of the semiconductor nanocrystals is capable of fluorescing at distinctive pre-selected wavelength ranges upon excitation, and wherein each of the semiconductor nanocrystals is covalently linked to a distinctive biomolecular probe having a selective affinity to a corresponding target biological material to be detected such that, upon contacting a solution containing a corresponding target biological material, the binding of each biomolecular probe with the corresponding target biological material results in an optically detectable change in the fluorescence emission intensity of the semiconductor nanocrystal.

In certain embodiments, each of the two or more semiconductor nanocrystals is a single crystalline semiconductor selected from the group consisting of CdSe, CdS, ZnS, ZnSe, CdTe, ZnTe, GaAs, AlAs, InAs, InP, GaN, and AlN.

In certain embodiments, the semiconductor nanocrystal is a single crystalline ZnSe doped with ions selected from the group consisting of $Cr^{2+}$, $Mn^{2+}$, $Fe^{2+}$, $Co^{2+}$, $Ni^{2+}$ and $Cu^{2+}$.

The semiconductor nanocrystals may be capped by organic bi-functional molecules or by organic multi-functional molecules, wherein the organic bi- or multi-functional molecules have a moiety at one end of a hydrocarbon chain that allows them to be covalently bound to the nanocrystal surface and a hydrophilic moiety at the other end of the hydrocarbon, chain that allows aqueous solubility and conjugation to a biomolecular probe.

The target biological materials may be two or more nucleic acid molecules or proteins, for example. The distinctive biomolecular probes are oligonucleotides, antibodies, or small molecule ligands.

BRIEF DESCRIPTION OF THE DRAWINGS

FIG. 1 shows a schematic example of the components of a hybrid nanosensor and an assembled probe. A single biomolecule is bonded to each QD. The rest of the QD's surface is saturated with the bi-functional organic molecules that are bonded covalently to the QD via a Zn—S bond.

FIG. 2 shows a schematic illustration of hybridization experiments in which a QD-dT25 sensor is hybridized with various dA-containing oligonucleotides in solution.

FIG. 3 shows exemplary hybridization of QD-dT25 probe with free dA results in structure-dependent fluorescence emission amplification.

FIG. 4 shows an exemplary fluorescence emission intensity comparison for the following structures: ZnSeQD-dT25 non-hybridized probe, ZnSeQD-dT25dA25 exactly matched hybridized structure, and two structures containing sequence mismatches at the 3' end of the target DNA: ZnSeQD-dT25dA20C5 and ZnSeQD-dT25dA5C20.

FIG. 5 shows an exemplary fluorescence emission intensity comparison for the following structures: ZnSeQD-dT25 non-hybridized probe, ZnSeQD-dT25dA25 exactly matched hybridized structure, and two structures containing sequence mismatches at the 5' end of the target DNA: ZnSeQD-dT25dC5A20 and ZnSeQD-dT25dC20A5.

FIG. 6 shows an exemplary fluorescence emission intensity comparison for the following structures: ZnSeQD-dT25 non-hybridized, probe, ZnSeQD-dT25dA25 exactly matched hybridized structure, and two structures containing sequence mismatches in the middle section of the sequence: ZnSeQD-dT25dA5C5A15 and ZnSeQD-dT25dA5C15A5.

FIG. 7 shows an exemplary normalized emission intensity difference plot comparing the fluorescence emission of an exactly matched ZnSeQD-DT25dA25 hybridized, complex to three additional hybridized complexes that contain a mismatch of 1, 3, or 5 base(s) in the middle section of the target sequence.

FIG. 8 shows exemplary data of structure-dependent fluorescence emission amplification from QD-DNA hybridized complexes using a "long" target (dT50) and two "short" probes. The results from hybridization with a complementary single probe are also included as reference.

FIG. 9 shows exemplary data of fluorescence emission amplification of MUA-capped ZnSe and (ZnSe)ZnS core-shell QDs after conjugation with dT25 at 1:1 particle to biomolecule ratio and after hybridization of the QD-dT25 sensor with free dA25. The ZnSe QDs without a shell exhibit the strongest emission amplification. The amplification becomes progressively smaller as the thickness of the shell increases.

FIG. 10 shows exemplary normalized fluorescence emission spectra of (1) HDA/TOP-capped ZnSe QDs dispersed in butanol and (2) MUA-capped ZnSe QDs dispersed in PBS.

FIG. 11 shows exemplary normalized fluorescence emission spectra of (1) TOPO/TOP-capped (ZnSe)ZnS core-shell QDs dispersed in butanol and (2) MUA-capped (ZnSe)ZnS core-shell QDs dispersed in PBS.

FIG. 12 shows exemplary stability data of MUA-capped aqueous dispersions ZnSe QDs in PBS. (a) Normalized fluorescence spectra of (1) freshly prepared QDs, (2) QDs after 7 days in storage at room temperature, and (3) QDs after 11 days in storage at room temperature. (b) Evolution of QD peak emission intensity vs. time in storage.

FIG. 13 shows exemplary stability data of MUA-capped aqueous dispersions of (ZnSe)ZnS core-shell QDs in PBS. (a) Normalized fluorescence spectra of (1) freshly prepared QDs, (2) QDs after 15 days in storage at room temperature, and (3) QDs after 32 days in storage at room temperature. (b) Evolution of QD peak emission intensity vs. time in storage.

FIG. 14 shows an exemplary comparison of fluorescence emission spectra of (1) MUA-capped ZnSe QDs in PBS and (2) the same QDs following conjugation to an oligonucleotide with 25 base pairs of adenine (dA25) indicates that conjugation of QDs to dA25 caused an increase in peak emission intensity.

FIG. 15 shows an exemplary distinct gel electrophoresis migration pattern, of two ZnSe QD-dA25 conjugate formulations compared to free ssDNA (dA25) and plain MUA-capped ZnSe QDs indicates conjugation of QDs to ssDNA.

FIG. 16 shows exemplary data of peak fluorescence emission intensity of ZnSe QDs conjugated to: (a) increasing amounts of dT25 ssDNA molecules; (b) oligo(dA) molecules of varying length; (c) 25-base ssDNA molecules of varying chemical sequence.

FIG. 17 shows exemplary fluorescence emission spectra of (ZnSe)ZnS core-shell QDs. (a): After conjugation to (1) dA25 (continuous line), (2) dT25 (dashed line), and (3) prior to ssDNA conjugation. (b): After conjugation to dT25 for two different ZnS shell thicknesses: 0.9 nm (thick shell) and 0.3 nm (thin shell). The size of the ZnSe QD cores was 4 nm in all cases.

FIG. 18 shows exemplary evolution of normalized peak emission intensity of QDs and QD-ssDNA conjugates in PBS with time in storage at room temperature; MUA-capped ZnSe QDs (▲); MUA-capped (ZnSe)ZnS core-shell QDs (●); ZnSe QD-dT25 conjugate (Δ) (ZnSe)ZnS-dT25 conjugate (○).

FIG. 19 shows exemplary effects of DNA hybridization on fluorescence emission of ZnSe QDs conjugated to oligo (dA25) and oligo(dT25). (a) Comparison of normalized emission spectra: (1) QD-dA25 or QD-dT25 (indistinguishable), (2) QD-dAdT25-QD hybridized structure. (b) Comparison of peak emission intensities.

FIG. 20 shows exemplary effects of DNA length on fluorescence emission of ZnSe QD-dA conjugates after hybridization with ZnSe QD-dT conjugates of equal length. (a) Comparison between the peak emission intensity of QD-ssDNA conjugates and QD-dsDNA-QD hybridized structures. (b) Emission intensify amplification factor after hybridization, in comparison to the emission of the corresponding non-hybridized QD-ssDNA conjugate.

FIG. 21 shows the location of the HBB gene on the short (p) arm of human chromosome 11 and HBB sequence in normal adult hemoglobin vs. HBB sequence in mutant adult hemoglobin.

Source:
http://www.ornl.gov/sci/techresources/Human_Genome/posters/chromosome/hbb.shtml FIG. 22 shows an exemplary schematic of ZnSe QD-cHBB probe hybridization with normal HBB and mutant (HBBs) targets.

FIG. 23 shows exemplary data of peak emission intensity amplification of a ZnSe QD-cHBB sensor alter hybridization with HBB and HBBs targets FIG. 24 is an exemplary schematic showing of a procedure for sample preparation and the expected dose response curve of a homogeneous DNA Assay that employs an engineered ZnSe QD-DNA probe for rapid quantitative detection of DNA mutations. (PCR: Polymerase Chain Reaction)

FIG. 25 shows an exemplary calibration lines far a homogeneous assay that uses a ZnSe QD-cHBB sensor to detect tree HBB (healthy) or HBBs (mutant) sequences in solution.

FIG. 26 shows exemplary homogeneous assay that detects the presence of free HBBs in solution using a ZnSe QD-cHBB sensor. The initial concentration of free HBBs corresponds to the point of departure of the dose response curve of the assay from the QD-cHBB/HBBs calibration line and is equal to 12.5 pmol/mL.

FIG. 27 shows exemplary (a) fluorescence emission intensity data of ZnSe QD-cHBB probe before and after hybridization for various free DNA (normal HBB sequence) concentrations, and (b) The intersection of the probe intensity vs. concentration line with the PBS buffer emission intensity at the same wavelength provides the detection limit for the probe and instrument (Horiba Fluorolog-3) combination used in these experiments.

FIG. 28 shows exemplary data of evolution of normalized peak emission intensity of QD-ssDNA conjugate and QD-dsDNA hybrid in PBS with time in storage at room temperature. ZnSe QD-dT25 conjugate (▲); ZnSe QD-dT25/dA25 hybrid (Δ).

FIG. 29 shows exemplary data of fluorescence emission intensity of ZnSe QD-BSA in PBS buffer (ZnSe QDs conjugated with different amounts of BSA at pH=7.723)

FIG. 30 shows exemplary data of fluorescence emission intensity of ZnSe QD-BSA complexes in PBS buffer solution as function of pH.

FIG. 31 shows exemplary data of fluorescence emission intensity of ZnSe QD-BSA complexes as function of time in storage in PBS buffer solution at various pH values.

FIG. 32 shows exemplary data of peak emission intensity of ZnSe QD-cHBB sensor at different times in storage and comparison to the emission intensity of the corresponding ZnSe QS-dsDNA complex formed after hybridization of the sensor with a complementary ssDNA target.

FIG. 33 shows an exemplary comparison of fluorescence emission spectra of MSA-capped Mn-doped ZnSe (ZnMnSe) QDs in PBS and the same QDs following conjugation to ssDNA with 25 base pairs of ademine (dA25).

FIG. 34 shows exemplary fluorescence emission of Mn-doped ZnSe (ZnMnSe) QD-dA25 conjugate in PBS before and alter hybridization with free dT25 ssDNA.

FIG. 35 shows exemplary data of peak emission intensity of Mn-doped ZnSe (ZnMnSe) QDs and QD-dA25 conjugates in PBS vs. time in storage at room temperature: MSA-capped ZnMnSe QDs (Δ); ZnMnSe-dA25 conjugates (●).

FIG. 36 shows exemplary fluorescence emission spectra of (1) MUA-capped ZnSe QDs in PBS and (2) QDs from the same stock solution conjugated to coneanavalin A.

FIG. 37 shows exemplary comparison of fluorescence emission spectra of (1) MSA-capped Mn-doped ZnSe (ZnMnSe)QDs in PBS and (2) QDs from the same stock solution conjugated to concanavalin A.

FIG. 38 shows exemplary fluorescence emission of ZnSe QD-ConA sensors in PBS buffer solution before and after binding with methyl-α-D-mannopyranoside target under conditions of sensor to target molecular ratio equal to 1:1, 1:2, 1:3 and 1:4.

FIG. 39 shows exemplary fluorescence emission of Mn-doped ZnSe (ZnMnSe)QD-Con A sensor in PBS buffer solution before and after binding with methyl-α-D-mannopyranoside target under conditions of sensor to target molecular ratio equal, to 1:1, 1:2, 1:3 and 1:4.

FIG. 40 shows exemplary data of normalized peak emission intensity of ZnSe QDs, ZnSe QD-ConA conjugates, and ZnSe QD-ConA/M bound complexes in PBS buffer solution vs. time in storage at room temperature.

FIG. 41 shows exemplary data of evolution of normalized peak emission intensity of Mn-doped ZnSe (ZnMnSe) QDs, ZnMnSe QD-ConA conjugates, and QD-ConA/M complexes in PBS buffer solution with time in storage at room temperature.

FIG. 42 shows exemplary data of fluorescence emission intensity of a ZnSe QD-ConA sensor and the ZnSe QD-Con A/4M bound complex vs. concentration of labeled ConA.

FIG. 43 shows exemplary data of emission intensity amplification when a ZnSe QD-HSA labeled antigen binds an anti-HSA antibody (ZnSe QD-HSA concentration: 53 µg/mL).

FIG. 44 shows (a) an exemplary fluorescence emission, intensity of the ZnSe QD-HSA labeled antigen and the ZnSe QD-HSA/antiHSA bound complex plotted as function of concentration, and (b) the low concentration range of the same plot as in (a) showing the ZnSe QD-HSA fluorescence emission intensity and the PBS buffer solution emission intensity at the same emission wavelength.

FIG. 45 shows exemplary (a) competitive immunoassay that detects the presence of free HSA in human serum plasma by progressively dosing the sample with ZnSe QD-HSA labeled antigen and anti-HSA antibody; and (b) normalized QD fluorescence emission intensity vs. labeled HSA concentration, corresponding to the competitive immunoassay.

FIG. 46 shows exemplary emission intensity data of (1) ZnSe QD-antiFGF sensor and (2) ZnSe QD-antiFGF/FGF bound complex.

FIG. 47 shows exemplary (a) direct immunoassay that detects the presence of free FGF in PBS solution by progressively dosing the sample with a ZnSe QD-antiFGF sensor; (b) Normalized fluorescence intensity plot for the direct immunoassay.

FIG. 48 shows exemplary emission intensity data of (1) ZnSe QD-antiPSA sensor and (2) ZnSe QD-antiPSA/PSA bound complex.

FIG. 49 shows an exemplary direct immunoassay that detects the presence of free PSA in PBS solution by progressively dosing the sample with ZnSe QD-antiPSA sensor.

FIG. 50 shows exemplary normalized fluorescence intensity data for a direct immunoassay that detects the presence of free *C. trachomatis* antigen in PBS solution by progressively dosing the sample with ZnSe QD-antiCTA sensor solution.

FIG. 51 shows an exemplary comparison of fluorescence emission amplification from QD-anti-HSA and QD-anti-FGF probes. The QD-anti-FGF probe exhibits higher intensity amplification and is a suitable antibody-based probe for a regular (non-competitive) homogeneous assay that detects FGF in solution.

FIG. 52 shows an exemplary comparison of fluorescence emission amplification by comparing QD-anti-HSA vs QD-anti-HSA/HSA and QD-anti-FGF vs. QD-anti-FGF/FGF. The QD-anti-FGF probe exhibits higher intensity amplification upon binding to tree FGF in solution and is a more suitable antibody-based probe for a regular (non-competitive) homogeneous assay that detects FGF in solution.

DETAILED DESCRIPTION OF THE INVENTION

The invention is based in part on the discovery of semiconductor nanocrystal-based sensors and related methods and systems useful for detection of biological materials. In particular, the invention provides quantum dot-based optical sensors and methods for direct, rapid and accurate detection and analysis of various biomolecules and materials and biological processes, such as nucleic acids, proteins, cells, etc. Changes in the fluorescence emission spectra of the QD-based sensors are employed to provide information about target biological materials. Hybrid QD-biomolecular sensors have been developed that utilize, for example, ZnSe QDs as responsive materials whose fluorescence emission intensity changes upon binding of the probe biomolecule to its intended target.

Thus, the present invention provides a unique utility of QDs for detection of biological materials and biomolecular interactions based on direct (i.e., non-FRET-induced) changes of their fluorescence spectra due to changes in the intrinsic electronic structure of the QD when a QD-labeled biomolecular probe binds with its intended target, e.g., in an aqueous environment.

For example, the dependence of the fluorescence emission intensity of ZnSe QD-ssDNA sensors on the final structure of the hybridized complex, enable detection of fully or partially complementary ssDNA targets in solution and allow discrimination of various targets based on their sequence. A QD-ssDNA probe that detects a sequence present in the healthy hemoglobin beta gene was designed and tested against a fully complementary ssDNA target and a single-base mutation that causes sickle-cell anemia. In general, fluorescence emission intensity variations after binding of ZnSe QD-biomolecule probes to specific targets can be exploited for developing homogeneous (non-separation) assays for rapid detection and quantitative analysis of biological targets in solution. Such assays combine simplicity and speed of detection and are attractive for applications in portable "point-of-care" diagnostic instruments, despite their lower sensitivity limits, in comparison to heterogeneous assays that involve separation of probe-target complexes from the solution, and take much longer time to execute (Kricka 1999). Additional properties of the QD-biomolecule probes, such as blinking rate variations and fluorescence emission shifts upon binding to the target, can be used to increase the detection, capability of these sensors.

Quantum confinement occurs when the size of semiconductor nanocrystals becomes smaller than the average electron-hole separation in an electron-hole pair (exciton) that is created by absorption of a photon with energy greater than the band gap of the material. For II-VI semiconductor nanocrystals, such as CdSe or ZnSe, the size corresponding to the quantum confinement threshold is a few nanometers (about 9 nm for ZnSe). The radiative recombination of an electron-hole pair in a QD has a "long" lifetime (>10 ns) in comparison to most fluorophores. This leads to narrow and symmetric emission spectra, in contrast to the broad red-tailed emission spectra of other fluorophores.

Intermittent fluorescence (blinking) has been observed from single QDs due to temporary trapping of electrons or holes by surface defects. (Nirmal, et al. 1996 *Nature* 383, 802-804.) As the size of the QDs shrinks below the quantum, confinement threshold, there is a size-dependent blue shift in the energy of the emitted photons. As a result, by controlling the size of QDs, one is able to obtain populations with specific narrow emission wavelengths that do not overlap. This combined with the ability of QDs to be excited by a photon with a wavelength shorter than their emission wavelength (continuous excitation) makes them attractive for multiplexing applications. Furthermore, QDs have wide spectral range, high brightness and excellent photochemical stability, which make them good candidates for biological imaging and diagnostics.

However, growing a progressively thicker shell over the QD core isolates the core from its immediate surroundings and diminishes its ability to directly sense the changes in the molecules conjugated to its surface, e.g. their binding with target biomolecules.

A new class of nanoscale fluorescent biomolecular sensors is disclosed herein. These sensors include, in certain preferred embodiments, an inorganic semiconductor nanocrystal, organic bi- or multi-functional surface capping molecules that enable dispersion of the nanocrystal in an aqueous solution, and one (or more) biomolecular probe molecule(s) that are covalently linked either to one (or more) of the surface capping molecules or directly to the surface of the nanocrystal. These nanoscale sensors enable direct sensing of biological materials and biomolecular interactions through changes in the optoelectronic properties of the nanocrystals resulting from the binding of a probe (a component of the sensor) to a biological target. The sensors do not need to involve a second fluorophore in a proximity-mediated energy transfer scheme. The changes in the optoelectronic properties of the nanocrystals are induced directly by the binding of the biomolecular probe to its specific target.

FIG. 1 is a schematic illustration of an exemplary embodiment of QD-based sensor of the invention. A single biomolecule is bonded to a QD. The QD's surface is saturated with the bi-functional organic molecules that are bonded covalently to the QD (e.g. through a Zn to S covalent bond in the case of ZnSe QDs).

Exemplary conjugative QD-biomolecular sensors have been developed that have the following components: (a) a semiconductor nanocrystal that is fluorescent (e.g., single-crystalline nanoparticles of zinc selenide (ZnSe) with sizes smaller than 9 nm exhibiting quantum confinement); (b) an organic bi- (or multi-) functional molecule, such as a mercapto-carboxylic acid or a mercapto-alcohol which is covalently bound to the surface of the QD at one end (e.g. through a Zn to S covalent bond in the case of ZnSe QDs) and with the other end of this molecule being either immersed in an aqueous solution or covalently bound to a biomolecule that can act as a probe; (c) a biomolecule, such as single-stranded DNA (ssDNA), protein, antibody, etc., that can act as a probe and bind to a target biomolecule or material in solution with high selectivity. For example, N-(3-Dimethylaminopropyl-N'-ethylcarbodiimide hydrochloride (EDC) can be used as a crosslinker to covalently bond the carboxylic acid end of a mercapto-carboxylic acid molecule to an amino group of a biological entity.

The changes of the optoelectronic properties of the QD may be monitored or measured directly by measuring one or more of the following parameters: for example, (a) changes in fluorescence emission intensity (increase or decrease); (b) changes in absorption intensity (increase or decrease); (c) changes in fluorescence emission spectra (e.g., shape of spectrum, emission wavelength, or blinking rate); (d) changes in absorption spectra (e.g., shape of spectrum or wavelength of absorption); (e) a blue or red shift in the maximum fluorescence emission wavelength.

QD-incorporated sensors of this invention directly respond to biomolecular conjugation with the target of the probe (e.g., a binding event) by altering their fluorescence emission spectrum. The difference in the fluorescence emission intensity of the QDs, for example, enables this new class of homogeneous assays to provide a direct, rapid and quantitative analysis of samples containing the target analyte. Furthermore, it enables classification of the structure of the resulting complex when multiple such structures may form, e.g. in the ease of DNA hybridization experiments, that produce distinct changes in the fluorescence emission intensity of the QDs.

The sensors of the invention are responsive optical biosensors (active sensors). Without being bound to the theories, it is believed that changes in the optoelectronic properties of the QDs are attributable to changes in their crystalline structure and defect density induced by the binding of the biological probe to the target. The binding of the QD-incorporated probe to the target may cause changes to the QD that are: mechanical (e.g., changes in the strain between atoms of the QD that are connected with covalent bonds), structural (e.g., changes in density of crystalline defects and surface traps), electronic (e.g., changes in the energy levels of the QD and changes in the charge distribution around the QD), or chemical (e.g., changes in the surface composition, of the QD and its interactions with the surrounding solvent).

In a preferred embodiment, the detection limit is a single target molecule. The QD-based sensors described in this invention include a single biomolecular probe bound to a single QD. Because the observed changes in the fluorescence emission intensity of the sensors are the result of the binding of the probe to a target, each bound QD-probe-target complex contributes equally to the observed change. As a result, the tracking of individual binding events is possible by tracking the fluorescence emission, of individual sensors using appropriate instrumentation.

The sensors and related methods disclosed herein provide a number of benefits and advantages, including sensitivity, simplicity, speed, selectivity/specificity, and performance.

Since the detected signal originates from individual QDs that are conjugated or hybridized to a single target (1:1 binding), the limit of detection of the technique is a single biomolecule. (Michalet, et al. 2005 *Science* Vol. 307, no. 5709, pp. 538-544; Pons, et al. 2009 *Annals of Biomedical Engineering* 37, 1934-1959.) Conventional commercial assays that employ immobilization of a population of target-probe complexes on a surface do not have the capability of detecting the signal from a single target biomolecule and require a significant number of immobilized probe-target complexes on a surface to obtain a measurable signal. As a result, the sensors of the present invention have a distinct advantage in terms of sensitivity, especially when sample amplification is infeasible and maximum sensitivity is essential, e.g. for detection of infectious agents that are not based on DNA.

The QD-based fluorescent sensors of this invention can directly detect biological interactions based on changes in the fluorescence emission spectra of the QDs without the need for employing a second fluorophore that interacts with the QD via distance-dependent Förster Resonance Energy Transfer (FRET). Additionally, there is no need for immobilization of the target-probe complex on a surface, washing of the unbound biomolecules and subsequent measurement of the intensify of the emitted signal, a common practice in current micro- and nano-particle-based biological assays and in more traditional ELISA-type assays.

The sensors and methods of the invention are suitable for homogeneous assays (in solution) and have fewer processing steps. They are simpler to execute compared to techniques that require immobilization of targets on a surface (e.g., on a spherical particle or on the surface of a vial or slide). By eliminating the need for separating the target-probe complex from the mixture, both complexity and processing time are significantly reduced because incubation and washing steps are eliminated. Furthermore, because the QD-based sensors disclosed herein are smaller than competing particle-based technologies (e.g., Nanosphere™ particles which are much larger than 10 nm and Luminex™ particles that are several microns in size), they diffuse more rapidly to the target. This, combined with direct detection of the fluorescence emission difference from the QDs, greatly reduces the time for measurement.

For nucleic acid detections, the sensors and methods of this invention enable single-base pair selectivity. For example, a single base pair mismatch can be detected in a direct assay employing a QD-oligonucleotide probe and a disease-relevant mutant gene sequence as target.

QD-based sensors have distinct advantages over other fluorophores, including their compact size, high brightness, continuous excitation by any wavelength shorter than the emission wavelength, high extinction coefficients, resistance to photobleaching, and narrow emission that enables multiplexing with QDs emitting at different wavelengths.

The sensors and methods of the invention allow homogeneous hybridization assays, which are rapid, simple to be executed, and can be combined with nucleic acid amplification in applications involving DNA, thus enabling the detection of very dilute concentrations of target nucleic acids. (Marras et al. 2006 *Clinica Chimica Acta* 363, 48-60.) These assays can be followed in real time, providing quantitative determination of target nucleic acids over a broad range of concentrations.

Thus, in one aspect, the invention generally relates to an optical biomolecular sensor for detecting a target biological material. The sensor includes: (a) an inorganic semiconductor nanocrystal capable of fluorescing at a pre-selected wavelength range upon, excitation, wherein the semiconductor nanocrystal has a surface allowing aqueous solubility of the semiconductor nanocrystal; (b) a biomolecular probe having an affinity to the target biological material: and (e) a linkage moiety associated with the semiconductor nanocrystal and with the biomolecular probe such that binding of the biomolecular probe with the target biological material results in an optically detectable change in the fluorescence emission spectrum of the semiconductor nanocrystal without employing a second fluorophore other than the semiconductor nanocrystal.

In some preferred, embodiments, a single biomolecular probe is linked to a single semiconductor nanocrystal.

The change in the fluorescence emission spectrum of the semiconductor nanocrystal may be a change in the fluorescence emission intensity, a change in the blinking rate of the emitted light, or a shift in the peak emission wavelength, for example. In some preferred embodiments, the semiconductor nanocrystal is single crystalline ZnSe that has a particle size from about 1 nm to about 9 nm.

ZnSe QDs can be synthesized by a variety of techniques, including injection of reactants into a hot coordinating solvent (e.g., Hines, et al. 1996 *J. Phys. Chem.* 100 (2), pp 468-471), using microemulsions or liquid crystals as templates (Karanikolos et al 2004 *Langmuir* 20 (3), pp 550-553; Karanikolos, et al. 2005 *Nanotechnology* 16(10), 2372-2380; Karanikolos, et al. 2006 *Nanotechnology* 17, 3121-3128; U.S. Pat. No. 7,608,237), or by vapor-phase synthesis (Sarigiannidis, et al. 2006 *J. Nanoparticle Research* 8, 533-542; Sarigiannis, et al. 2002 *Appl. Phys. Lett.* 80, 4024).

In some more preferred embodiments, the single-crystal line ZnSe has a particle size from about 3 nm to about 6 nm. In certain preferred embodiments, the population of single-crystalline ZnSe nanocrystals is either monodisperse with particle sizes that deviate less than about 10% in root mean square diameter or polydisperse with particle sizes that deviate more than about 10% in root mean square diameter.

In certain embodiments, the semiconductor nanocrystal is single crystalline ZnSe doped with ions selected from the group consisting of $Cr^{2+}$, $Mn^{2+}$, $Fe^{2+}$, $Co^{2+}$, $Ni^{2+}$, and $Cu^{2+}$.

The semiconductor nanocrystal may be single-crystalline and includes elements from groups II and VI of the periodic table, for example, selected from ZnSe, ZnS, ZnTe, CdSe, CdS, CdTe, HgTe, and ternary and quaternary mixtures of the component elements thereof.

The semiconductor nanocrystal may be single-crystalline and includes elements from groups III and V of the periodic table, for example, selected from GaAs, GaN, GaP, GaSb, AlAs, AlN, AlP, AlSb, InAs, InP, InSb, and ternary and quaternary mixtures of the component elements thereof.

The semiconductor nanocrystal may be single-crystalline and includes elements from groups IV and VI of the periodic table, for example, selected from PbS, PbSe, PbTe, SnTe, and ternary and quaternary mixtures of the elements thereof.

The semiconductor nanocrystal may be single-crystalline and includes elements from group IV of the periodic table, for example, Si or Ge.

In some embodiments, the semiconductor nanocrystal consists of a single-crystalline core and an inorganic shell made of a material with wider band gap than the core material and wherein the inorganic shell is sufficiently thin to allow detectable changes in the fluorescence emission spectrum of the single-crystalline core. The single-crystalline core may be a single-crystalline ZnSe or CdSe nanocrystal and the shell is ZnS. For example, the single-crystalline core may have a diameter from about 1 nm to about 9 nm and the inorganic shell has a thickness from one monolayer to about 1 nm.

In some embodiments, the surface of the semiconductor nanocrystal is capped by organic bi-functional molecules, wherein the organic bi-functional molecules have a moiety at one end of a hydrocarbon chain that allows them to be covalently bound to the nanocrystal surface and a hydrophilic moiety at the other end of the hydrocarbon chain that allows aqueous solubility and conjugation to a biomolecular probe.

The organic bi-functional molecules may be selected from the group consisting of: mercaptocarboxylic acids $HS(CH_2)_nCOOH$, mercaptoalcohols $HS(CH_2)_nOH$, aminocarboxylic acids $H_2N(CH_2)_nCOOH$, thiolamines $HS(CH_2)_nNH_2$, or aminoalcohols $H_2N(CH_2)_nOH$, wherein each n is independently an integer from about 2 to about 20 and the hydrocarbon chains are linear or branched. The surface of the semiconductor nanocrystal may be capped by organic multi-functional molecules, wherein, the organic multi-functional molecules are selected from the group consisting of: dihydrolipoic acid (DHLA) $HSCH_2CH_2CH(SH)(CH_2)_4COOH$, hydroxy-terminated DHLA-polyethylene glycol (PEG) $HSCH_2CH_2CH(SH)(CH_2)_4CONH(CH_2CHO)_nCH_2CH_2OH$; amine-terminated DHLA-PEG $HSCH_2CH_2CH(SH)(CH_2)_4CONH(CH_2CHO)_nCH_2CH_2NH_2$; carboxylic acid-terminated DHLA-PEG $HSCH_2CH_2CH(SH)(CH_2)_4CONH(CH_2CHO)_nCH_2CH_2COOH$, wherein each n is independently an integer from about 5 to about 15.

In some embodiments, the pre-selected wavelength range may be from about 375 nm to about 450 nm when the semiconductor nanocrystal is ZnSe having a diameter from about 1 nm to about 9 nm. In some embodiments, the pre-selected wavelength range is from about 480 nm to about 640 nm when the semiconductor nanocrystal is CdSe having diameter from about 2 nm to about 7 nm.

In certain embodiments, the pre-selected wavelength is about 585 nm when the semiconductor nanocrystal is manganese-doped ZnSe (ZnSe:Mn) having a diameter from about 1 nm to about 9 nm, in certain embodiments, the pre-selected wavelength, is about 540 nm when the semiconductor nanocrystal is copper-doped ZnSe (ZnSe:Cu) having a diameter from about 1 nm to about 9 nm.

The target biological material may be a single- or double-stranded nucleic acid (e.g., a DNA or a RNA). The target biological material may be a protein (e.g., human serum albumin, fibroblast growth factor). The protein may be selected from the group consisting of enzymes, proteases, nucleases, recombinases, integrates, RNA polymerases, DNA polymerase, histases, topoisomerases, helicases, isomerases, estarases, oxidoreductases, acyltransferases, lipases, kinases, phosphatases, hydrolases, lectins, structural proteins, transcription factors, translation factors, protein binding factors, nucleic acid binding factors, small molecule binding proteins, macromolecule binding proteins, growth factors, growth factor receptors, cell surface molecules, cell surface receptors, extracellular matrix, cytokines, cytokine receptors, chemokines, chemokine receptors, serum factors, collagen, elastins, histories, keratines, nuclear receptors, ribosomal proteins, extrachromosomal replicons, chromosomes, chromatin, tubuline, actin, dynein, or kinesins.

The target may be selected from a variety of different biological materials, such as amino acids, oligopeptides, polypeptides, metabolites, sugars, disugars, oligosaccharides, lipids, subcellular structures, subcellular organelles, microtubules, actin filaments or microfilaments.

The biomolecular probe may be selected from a variety of biomolecules, such as oligonucleotides, antibodies or antigens, small molecule ligands or immune receptors (e.g., Toll-like receptors or pattern recognition receptors).

The linkage moiety may be selected from a variety of chemical moieties, such as mercaptocarboxylic acids, mercaptoalcohols, aminocarboxylic acids, thiolamines, or aminoalcohols, with carbon chains that are either linear or branched and consisting of two to twenty carbons. In some embodiments, the linkage moiety is selected from the group consisting of mercaptocarboxylic acids, dihydrolipoic acid, PEG-modified mercaptocarboxylic acids and PEG-modified dihydrolipoic acid.

In another aspect, the invention generally relates to a method for detecting a target biological material. The method includes: (a) providing an aqueous solution of an optical, biomolecular sensor comprising an inorganic semiconductor nanocrystal, a biomolecular probe having an affinity to the target biological material, and a linkage moiety associated with the semiconductor nanocrystal and with the biomolecular probe, wherein the inorganic semiconductor nanocrystal is capable of fluorescing at a pre-selected wavelength range upon excitation; (b) contacting the optical biomolecular sensor with a sample to be tested for the presence of the target biological material; and (c) detecting a change in fluorescence emission intensity of the semiconductor nanocrystal, whereby the change in the intensity indicates the presence of the target biological material. In some preferred embodiments, the method is performed as a direct homogeneous assay.

In certain embodiments, the target biological material includes an antigen and the biomolecule probe comprises an antibody that selectively binds with this antigen.

In certain embodiments, the biomolecular probe includes a natural or synthetic oligonucleotide. The target biological material, may be a single- or double-stranded nucleic acid.

In some embodiments, the biomolecular probe may include an amine-modified oligonucleotide complementary to a sequence found in the healthy hemoglobin beta (HBB) gene.

In some embodiments, the biomolecular probe may include an amine-modified oligonucleotide with sequence of 5'-AGACTTCTCCTCAGGAGTCAG and an amine group at the 5' edn that is complementary to a sequence found in the healthy hemoglobin bets (HBB) gene.

In some embodiments, the target biological material may include an oligonucleotide with sequence of 5'-CTGACTCCTGAGGAGAAGTCT found in the healthy hemoglobin beta (HBB) gene.

In some embodiments, the biomolecular probe may include an amine-modified oligonucleotide complementary to a sequence found in a mutated hemoglobin beta (HBBs) gene. The hemoglobin beta (HBB) gene may include a single-base mutation wherein the hydrophobic amino acid valine takes the place of a hydrophilic glutamic acid at the sixth amino acid position, of the beta-HBB polypeptide chain.

In some embodiments, the target biological material may include an oligonucleotide with sequence of 5'-CTGACTCCTGTGGAGAAGTCT found in a mutated hemoglobin beta (HBBs) gene.

In yet another aspect, the invention generally relates to a multiplexed homogeneous assay for detecting target biological materials. The assay includes an aqueous solution of two or more inorganic semiconductor nanocrystals, wherein each of the semiconductor nanocrystals is capable of fluorescing at distinctive pre-selected wavelength ranges upon, excitation, and wherein each of the semiconductor nanocrystals is covalently linked to a distinctive biomolecular probe having a selective affinity to a corresponding target biological material to be detected such that, upon contacting a solution containing a corresponding target biological material, the binding of each biomolecular probe with the corresponding target biological material results in an optically detectable change in the fluorescence emission intensity of the semiconductor nanocrystal.

In certain embodiments, each of the two or more semiconductor nanocrystals is a single crystalline semiconductor selected from the group consisting of CdSe, CdS, ZnS, ZnSe, CdTe, ZnTe, GaAs, AlAs, InAs, InP, GaN, and AlN.

The semiconductor nanocrystals may be capped by organic bi-functional molecules or by organic multi-functional molecules, wherein the organic bi- or multi-functional molecules have a moiety at one end of a hydrocarbon chain that allows them to be covalently bound to the nanocrystal surface and a hydrophilic moiety at the other end of the hydrocarbon chain that allows aqueous solubility and conjugation to a biomolecular probe.

The target biological materials may be two or more nucleic acid molecules or proteins, for example. The distinctive biomolecular probes are oligonucleotides, antibodies, or small molecule ligands.

EXAMPLES

Nucleic Acid Detection.

DNA hybridization was performed in homogeneous assays by employing QD-oligo sensors containing a single strand (the probe) that is complementary to a target DNA sequence in solution. The probes were hybridized with free DNA targets that bad various levels of mismatch with the probe's sequence. The change in the fluorescence intensity of the sensor enables detection of the complementary sequence as well as mismatches down to a single base pair. It can also provide information about the structure of the resulting hybridized complexes. Since the probe-target hybridization takes place in a homogeneous assay and the measurement of the fluorescence intensity change is monitored continuously, the detection of the hybridization is rapid. The nucleic acids can be natural, or synthetic. ZnSe QD-single-stranded-DNA sensors have been employed that contain a single-stranded DNA sequence complementary to the hemoglobin beta gene (cHBB) to detect the mutant (HBBs) gene that is a marker for (and the cause of) sickle cell anemia. Unambiguous signal discrimination (20% difference) was demonstrated when the ZnSe QD-cHBB probe hybridized with its exact match (HBB sequence) vs. with the most common single-base-pair mutant sequence (HBBs).

Protein Detection. QD-protein sensors were employed in a competitive homogeneous immuno-assay and provided rapid quantitative analysis of human serum albumin (HSA) in solution. The competitive assay protocol employs a ZnSe QD-HSA (labeled antigen) and an anti-HSA antibody. The QD-labeled antigen competes with free HSA for the anti-HSA antibody, enabling direct detection of both the presence and concentration of free HSA in a sample. This detection, is derived from changes in the fluorescence intensity of the ZnSe QDs, without needing to immobilize any of the resulting antigen-antibody complexes on a surface.

ZnSe QDs with size ranging from 3 to 5 nm were capped with mercapto-undecanoic acid (MUA) and dispersed in aqueous solution (PBS buffer). They were subsequently conjugated with the probe biomolecules containing amino groups using EDC as a cross-linker. In all cases, the hybrid sensors were formed using a 1:1 QD to biomolecule ratio, so that each nanosensor consisted of one probe biomolecule covalently bound to a single QD.

I. Synthesis of Hybrid ZnSe QD-Based Sensors (a) ZnSe QD Synthesis

In a 50 ml, 3-neck round bottom flask, 1-hexadecylamine (HDA, 13 grams) was melted at 60° C. and degassed at 100° C. for 1 hour. Selenium powder (~100 mesh, $8.7 \times 10^{-2}$ grams) and trioctylphosphine (TOP, 1 mL) were placed into a 15 mL scintillation vial, sealed with a septum and purged with $N_2$. The selenium-TOP mixture was heated at about 60° C. until a homogeneous solution was obtained and then allowed to return to ambient temperature. Diethylzinc (1 mL, 1 M solution in heptane) was then added to the scintillation vial, forming the precursor mixture, and diluted with TOP (4 mL). The degassed HDA, under constant vigorous stirring, was then heated to 300° C. and the precursor was swiftly injected into the hot coordinating solvent in one swift motion. The reaction was quickly cooled to about 230° C. and then returned to 270° C. to allow the ZnSe nanocrystals to grow. Samples were extracted at increasing reaction times to obtain ZnSe QDs with increasing particle sizes. (Hines, et al. 1998, *J. Phys. Chem. B* 102 (19):3655-3657.)

(b) ZnSe QD Surface Modification 1.2 mL of as-prepared ZnSe QD reaction mixture were transferred to a 10 mL centrifuge tube which contained 2 mL methanol to precipitate the QDs. The mixture was centrifuged at about 4200 rpm for 30 minutes (Fisher Centrific Model 225 Centrifuge) to separate the coordinating solvents from the QDs. The supernatant was decanted and the precipitate was first washed with 1.5 mL butanol/0.5 mL methanol mixture and then with 2 mL methanol. Centrifugation was performed following each washing step to remove the solvent. The collected QDs were dispersed in 1 mL hexane and then transferred into a 15 mL vial using a pipette. The QD-hexane solution was kept under vacuum and evaporation of the solvent yielded about 12 mg solid ZnSe QDs. The solid QDs were mixed with about 25 mg MUA and the mixture was heated to about 60° C. The MUA-ZnSe QD mixture was stirred at 60° C. under atmosphere and dark conditions for 16 hours. The heating was subsequently stopped and the MUA-ZnSe QD mixture was allowed to cool down to room temperature. Methanol (3 mL) was then added to the reaction vial to obtain a milky MUA-capped ZnSe QD-methanol solution. In order to uniformly disperse the QDs in methanol, the samples can be sonicated for about 2 minutes.

The MUA-capped QD-methanol solution was transferred to a centrifugation tube and potassium t-butoxide-methanol solution was added to deprotonate the carboxylic acid group of MUA. Potassium t-butoxide-methanol solution (0.5M) was freshly prepared by dissolving ~45 mg (0.0004 mol) potassium t-butoxide into 0.8 mL methanol. The potassium t-butoxide-methanol solution was added into the MUA-ZnSe QD-methanol mixture drop-wise until the milky solution became clear. Then, a volume of ethyl ether equivalent to about twice the volume of methanol (volume of ethyl ether:volume of methanol=~2:1) was added to precipitate the MUA-capped QDs. The mixture was allowed to settle for 30 min, and centrifugation was used to remove the solvents (at about 4200 rpm for 15 minutes). After centrifugation, the supernatant was decanted and the precipitate was washed one more time with 2 mL ethyl ether. Finally, the water-dispersible ZnSe QDs were dispersed in 1.5 mL PBS buffer solution and filtered with a 0.2 µm syringe filter (WHATMAN 13 mm GD/X Disposable Filter Device and polypropylene filler media) to remove any aggregates, if necessary. The clear ZnSe QD-MUA buffer solution was stored under dark conditions.

(c) Conjugation of ZnSe-MUA QDs to Biomolecules

ZnSe QDs capped with MUA were conjugated with amino-modified biomolecules by executing a two-step procedure that employs N-(3-Dimethylaminopropyl)-N'-ethylcarbodiimide hydrochloride (EDC) as a cross-linker following a standard protocol. In a typical experiment, 8 mg of EDC were added to 2.0 mL of QD-MUA PBS buffer solution (QD concentration: $9.4 \times 10^{14}$/mL) and the solution was incubated for 25 min at room temperature. Then, a specific amount of an amine-containing biomolecule was added keeping the ratio of the number of ZnSe QDs to the number of biomolecules available for conjugation at 1:1. The mixture was incubated at room temperature for 4 hours to complete the covalent coupling reaction and was stored overnight before being used in biological detection experiments.

The fluorescence emission of the ZnSe QDs was monitored using a SPECTRAmax GEMINI spectrofluorometer (Molecular Devices) or a Fluorolog 3 spectrofluorometer (Horiba Jobin-Yvon). The excitation wavelength was fixed at 350 nm. The fluorescence emission wavelength of the QDs was in the range of 380 nm to 420 nm, depending on their size.

II. ZnSe QD-Oligo Nanosensors for Nucleic Acid Detection

A series of experiments were performed using oligonucleotide dT25 as the probe biomolecule. ZnSe QD-dT25 nanosensors were used to detect dA-containing oligonucleotides in solution. The fluorescence emission intensity of the QDs was monitored and was found to change upon hybridization of the nanosensor with free dA-containing oligonucleotides. The fluorescence emission intensity of the QDs increased when a hybridized QD-dT-dA complex was formed. Furthermore, the amplification factor was dependent on the structure of the QD-dT-dA complex. A schematic of these experiments is shown in FIG. 2.

In a typical series of experiments, a dispersion of ZnSe QD-dT25 nanosensors was mixed with aqueous dispersions of free dA10, dA25, and dA50 oligonucleotides. In each case the molar amount of free dA was equal to the molar amount of dT25 in the nanosensor solution. Upon dA-dT hybridization, the fluorescent emission intensity of the ZnSe QDs exhibited significant amplification, when compared to the emission intensity recorded from the original QD-dT25 solution. The amplification, factor was different for different dA oligonucleotide sizes, as shown, in FIG. 3. In comparison to the fluorescence emission intensity of the ZnSeQD-dT25 nanosensors in solution, the peak fluorescence intensity recorded from the hybridized structures was amplified 5.1 times for ZnSeQD-dT25dA10, 6.8 times for ZnSeQD-dT25dA25, and 8.9 times for ZnSeQD-dT25dA50. In this series, the longer the complementary DNA length, the stronger the observed enhancement was. The shape of the emission spectrum of the QDs was not altered by hybridization, as demonstrated by the almost exact overlap of the normalized emission spectra obtained from these QD-DNA hybridized complexes.

The following three cases further demonstrate detection of sequence mismatch on the fluorescence emission intensity of QD-oligo sensors: Case A, where the target nucleic acid contains a mismatch at the 3' end; Case B, where the target nucleic acid contains a mismatch at the 5' end; and Case C, where the target nucleic acid contains a mismatch in the middle section of the target sequence.

Case A: Three experiments using ZnSeQD-dT25 sensors were performed. In all cases, equimolar amounts of the sensor and free DNA were allowed to hybridize.

The first experiment was used as a reference and involved free complementary DNA (dA25) as the target, which was an exact match for the dT25 oligonucleotide of the probe. The result was a fully hybridized QD-dT25dA25 structure. The second and third experiments involved target DNA that had a 5-base long and a 20-base long mismatch at the 3'end, in this ease dA20C5 and dA5C20, respectively.

Hybridization of the ZnSeQD-dT25 sensor with free DNA having a mismatch at the 3' end resulted in a structure containing two single stranded DNA tails near the QD, as depicted in FIG. 4. FIG. 4 also shows a comparison of the peak emission intensity of the sensor and the three QD-DNA hybridized structures. In this case, structure-dependent amplification of the peak emission intensity is again observed. However, the mismatched structures exhibited stronger emission intensify than the exactly matched one. Furthermore, the longer the mismatch the stronger the observed emission intensity was.

Case B: In this series of experiments, the sequence mismatch on the target DNA oligonucleotides was switched from the 3'end to 5'end. When QD-dT25 sensors are hybridized with target DNA containing a 5- or 20 base-long mismatches at the 5' end, a partially hybridized structure is obtained that has a double helix near the end attached to the QD and single-stranded DNA tails at the other end (FIG. 5). The hybridized structures that contained a mismatch exhibited higher emission intensity than those without a mismatch. However, the samples containing the longer base mismatch (20 bases) exhibited smaller emission, intensity compared with the ones that had the shorter base mismatch (5 bases). The correlation between the hybridized structures and the corresponding value of the amplification factor can be exploited to identity the location and size of the mismatch.

Case C: In this series of experiments, the mismatch on the target DNA oligonucleotide was in the middle section of the sequence (i.e., it did not include the end bases). FIG. 6 shows a comparison of the peak emission intensities of the sensor, the fully hybridized complex, and the two partially hybridized structures. Here, the partially hybridized structures exhibited weaker fluorescence emission intensity than the fully hybridized complex. Their fluorescence emission intensity decreased as the length of the mismatch increased.

Mismatch Sensitivity Test: Experiments were performed to test the sensitivity of the method for detecting a sequence mismatch down to 1 base pair. In these experiments, the sensors were again ZnSeQD-dT25 and the target nucleic acids contained a (continuous) sequence mismatch with size of 1, 3, or 5 base(s), located in the middle section of the sequence. After hybridization, the normalized emission intensity difference was calculated and plotted, using the calibration formula shown in FIG. 7. By using this formula, the normalized emission difference of the hybridized complex corresponding to an exact match is always equal to 1. The results indicate that the QD-based nanosensors are capable of resolving, sequence mismatches down to 1 base pair.

Effect of Multiple-Sensors

Preliminary experiments aiming to test the performance of short QD-oligo sensors in detecting specific sequences embedded in longer strands of free DNA were also performed.

In this series of experiments dT50 was the free target DNA used. The following four sensors were tested against this target: QD-dA50 (reference, 1:1 probe to free DNA ratio); QD-dA25 (2:1 probe to free DNA ratio); QD-dA15 (2:1 probe to free DNA ratio); QD-dA10 (2:1 probe to free DNA ratio)

FIG. 8 shows a comparison of the observed peak emission amplification from hybridized QD-DNA structures, using as reference the emission intensity of the non-hybridized probe. Structure-dependent emission intensity amplification was observed. The highest amplification was obtained when two equal-size probes covered the entire free DNA by hybridizing with it from opposite ends of it. The second highest amplification was obtained when a single probe exactly matched the entire free DNA. When two shorter equal-size probes hybridized with free DNA from opposite ends providing only partial hybridization of the free DNA strand, the emission amplification was smaller and decreased as the length of the probes decreased.

Effect of adding a shell to the QD: A series of experiments was performed to test the effects of adding a ZnS shell to the ZnSe QDs and using the ZnSe—ZnS core-shell structure as the fluorescent component of the nanosensor. Two shell thicknesses were studied: a "thin" shell with an estimated thickness of 0.3 nm; and a "thick" shell with an estimated thickness of 0.9 nm. The ZnSe QDs were covered with the ZnS shell according to a reported procedure (Hines, et al. 1996 *Journal of Physical Chemistry* 100 (2):468-471.)

In FIG. 9 the fluorescence emission intensity amplification factor is plotted for three ZnSe and (ZnSe)ZnS core-shell QD populations, before conjugation with a biomolecule, after conjugation with dT25 at 1:1 ratio of QDs to biomolecules, and after hybridization with free dA25. The fluorescence emission intensity amplification factor for each case is computed using the initial emission intensity of the MUA-capped QDs in water as reference. For the core-shell structures the amplification factor becomes progressively smaller as the shell becomes thicker. This is due to the fact that a progressively thicker shell isolates the core from its surroundings and hinders its ability to directly detect biological interactions.

III. Detection of the HBB Gene and its Mutant that Causes Sickle Cell Anemia Using ZnSe QD-Based Nanosensors Materials Diethylzinc ($Et_2Zn$, 1.0 M solution in heptane), N-(3-Dimethylaminopropyl)-N'-ethylcarbodiimide hydrochloride (EDC), 1-hexadecylamine (HDA, 98%), hexamethyldisilathiane (synthesis grade, $TMS_2S$), 11-mercaptoundecanoic acid (MUA, 95%), potassium tert-butoxide (95%), tetrahydrofuran (anhydrous, 99.9%), trioctylphosphine (TOP, 90%) and trioctylphosphine oxide (TOPO, 90%), and selenium powder (−100 mesh, 99.5%) were purchased from Sigma-Aldrich. Methanol, butanol, and hexane (all anhydrous) were purchased from Fisher. 10× phosphate buffered saline (PBS) was purchased from GIBCO. All ssDNA molecules used in the experiments were synthetic nucleic acids purchased from Sigma-Aldrich.

Synthesis and Functionalization of ZnSe and (ZnSe)ZnS Core-Shell QDs

ZnSe QDs were synthesized following a previously reported procedure that is known to yield highly fluorescent ZnSe QDs. (Hines, et al. 1998 *J. Phys. Chem. B* 102 (19):3655-3657.) 13 g of 1-hexadecylamine (HDA) were placed in a three-head flask, dried, and degassed under vacuum (about 1 Torr) at ~90-95° C. for 30 minutes. At the same time, 1 mL 1 M TOPSe solution was prepared by dissolving 0.08 g selenium powder in 1 mL trioctylphosphine (TOP) under a nitrogen atmosphere in a water bath at ~50° C. Next, 0.8 mL of 1 M $Et_2Zn$ heptane solution was added (Se:Zn=1.25:1) and the mixture was diluted with 4 mL of TOP to form the precursor stock solution. The HDA was heated to 310° C. under 1.10 atm of $N_2$. At that temperature the heating was stopped, and the precursor stock solution was swiftly injected into the reaction flask in a single step. The temperature inside the reactor dropped to ~240° C. immediately after the injection. Heating was restored to the reaction flask and the temperature was raised to 270° C. The nanocrystals were grown at this temperature. The reaction was stopped 30 minutes after the precursor injection and the reaction mixture was allowed to cool to ~60° C. under $N_2$ atmosphere. The QDs were stored in their synthesis solution under dark conditions until later use.

To prepare (ZnSe)ZnS core-shell QDs, a flask containing 7.5 g of trioctylphosphine oxide (TOPO, 90%) and 3.8 g HDA (TOPO/HDA ratio ~2:1) was heated in an oil-bath to 150° C. and the reaction system was placed under vacuum (about 1 Torr) for 1 hour. Then, 0.5 mL of trioctylphosphine (TOP) was injected into the flask and the temperature was reduced to ~65° C. At this temperature, 6 mL of ZnSe QD solution (3 mL as-prepared ZnSe QDs with ~5 nm diameter dispersed in 3 mL hexane) was transferred into the flask via a syringe and the solvent was evaporated while keeping the flask under vacuum for at least half an hour at 60° C. Meanwhile, the precursor solution was prepared by adding 22 μL hexamethyldisilathiane ($TMS_2S$) and 0.1 mL 1 M $Et_2Zn$ heptane solution to 3 mL TOP under a $N_2$ atmosphere (S:Zu=1:1). The reaction flask containing ZnSe QDs dispersed in HDA and TOPO was heated under a $N_2$ atmosphere to 210° C. The precursor solution was injected into the reaction flask every 2 minutes in doses of 0.5 mL. After the injection was completed, the temperature was reduced to 100° C. and the reaction mixture was kept for 3 hours at this temperature under vigorous stirring to complete the surface coverage.

11-mercaptoundecanoic acid (MUA) was used as a capping agent in order to form wafer-dispersible ZnSe QDs. 3 mL methanol were added to 1.5 mL ZnSe (or 2 mL (ZnSe)ZnS) as-synthesized QDs to precipitate the QDs, then the mixture was centrifuged (4000 rpm for 30 minutes) to remove the coordinating solvents. The supernatant was decanted and the precipitate was washed with 2 mL butanol and then with 2 mL methanol. Centrifugation was performed to remove each solvent. The collected QDs were dispersed in 2 mL hexane and centrifuged to remove the precipitate which contained larger particles. The supernatant was kept under vacuum and evaporation of the solvent yielded solid ZnSe (or (ZnSe)ZnS) QDs (~20 mg). The solid QDs were mixed with ~25-30 mg MUA and the mixture was heated to 60° C. The MUA-ZnSe QD mixture was stirred, at 60° C. under $N_2$ protection and dark conditions for 14 hours. The heating was subsequently stopped and 1 mL anhydrous tetrahydrofuran (THF) was added to the reaction vial to obtain a clear MUA-capped ZnSe QD-THF solution. This solution was transferred to a centrifugation tube and potassium t-butoxide-THF solution was added to deprotonate the carboxylic acid group of MUA, which also caused the clear solution to become a gel. After centrifugation (4000 rpm for 30 minutes), the supernatant was decanted and the precipitate gel was washed twice with THF. Each time the precipitate was kept and the supernatant was discarded after centrifugation. Finally, the MUA-capped ZnSe QDs were dispersed in 1.5 mL PBS and centrifuged (4000 rpm for 4 minutes) to remove any remaining residue. The clear QD buffer solution was stored under dark conditions at room temperature and used in the DMA conjugation experiments.

FIG. 10 shows the normalized emission spectra of as-synthesized and water-dispersed ZnSe QDs. The peak emission wavelength of the water-dispersed QDs exhibits a small blue shift in comparison to the one from the as-synthesized QDs, indicating a small reduction in QD average size. It also exhibits a red tail, most probably due to formation of larger QDs by coalescence of uncapped ones during the surface cap exchange procedure. FIG. 11 compares the normalized emission spectra of MUA-capped (ZnSe)ZnS core-shell QDs dispersed in PBS and as-synthesized QDs from the same batch dispersed in butanol. In this case, there is no detectable shift in the peak emission wavelength before and after dispersion in water.

Stability of ZnSe and (ZnSe)ZnS Core-Shell QDs in Aqueous Solution

The stability of ZnSe QD dispersions in PBS was studied by monitoring the fluorescence emission spectrum, of the QDs as a function of time in storage at room temperature under dark, conditions. The normalized, spectra, shown in FIG. 12a, reveal the formation of a blue shoulder, most probably due to core shrinkage (dissolution) by ionic attack, and a red shoulder, most probably due to particle coalescence. Data obtained after 7 days and 11 days exhibited a decrease in the maximum, emission intensity by 45% and 55%, respectively (FIG. 12b). In contrast to ZnSe QDs, aqueous dispersions of (ZnSe)ZnS core-shell QDs were more resistant to environmental attack in storage and their spectra exhibited only a red shoulder, again most probably due to particle coalescence (FIG. 13a). Their stability in water was also improved and they exhibited a slow decay in fluorescence emission intensity that dropped by 30% after 15 days and by 40% after 32 days in storage (FIG. 13b).

ZnSe QDs were conjugated with amino-modified ssDNA of various lengths and sequence chemistry using a standard carbodiimide linking protocol. Amino-modified ssDNA molecules were covalently conjugated to QD surfaces via the —COOH functional groups of the MUA. A two-step standard linking protocol was employed, as follows: 10 mg of N-(3-Dimethylaminopropyl)-N'-ethylcarbodiimide hydrochloride (EDC) cross-linking agent were added to 1.2 mL of QD PBS buffer solution (58 mM $Na_2HPO_4$, 17 mM $NaH_2PO_4$, and 68 mM NaCl, pH 7.4) and the solution was incubated for 25 minutes at room temperature. Next, a specific amount of a solution of amino-modified ssDNA dissolved in DI water was added. The mixture was incubated at room temperature for 4 hours to complete the covalent coupling reaction. (Hermanson, 1996 *Bioconjugate Techniques*, San Diego.)

Preparation of ZnSe QD-ssDNA Sensor and Immunoassay

A ZnSe QD-ssDNA sensor was developed that detects the presence of a ssDNA sequence corresponding to the hemoglobin beta gene (HBB) and can distinguish it from a sequence containing a common single-base mutation (HBBs) that causes sickle-cell anemia. The ssDNA probe sequence was designed by using the program Primer3 (http://frodo.wi.mit.edu/primer3/). The ssDNA probe (cHBB) had 21 bases with sequence of 5'-AGA CTT CTC CTC AGG AGT CAG-3' and an amine group at the 5' end that was used to conjugate the probe to MUA-capped ZnSe QDs. The probe sequence was complementary to a sequence in the healthy HBB gene. The two free ssDNA targets used in this study were the complementary sequence 5'-CTG ACT CCT GAG GAG AAG TCT-3' (HBB), a common single base pair mutant (HBBs) with sequence 5'-CTG ACT CCT GTG GAG AAG TCT-3' that causes sickle-cell anemia. The single base mismatch in the mutant is in the middle of the target sequence (an adenine was changed to thymine (bold)). The cHBB probe is expected to hybridize completely with the complementary HBB target sequence. The single mismatched base pair near the middle of probe in the ease of the mutant HBBs target is expected to significantly reduce the probe-target hybridization efficiency.

The ZnSe QD-cHBB sensor was prepared by conjugation of ZnSe QDs with cHBB. The ratio of QD particles to cHBB probe molecules was kept close to 1:1 to ensure that each QD was conjugated on average to a single cHBB molecule. Two milliliter QDs PBS buffer solution (with QD concentration of ~$9.4 \times 10^{14}$ particles/ML) was mixed with 3 nmol of amine-modified cHBB probe molecules and 8 mg of EDC and the mixture was stirred at room temperature for 4 hours. The QD-cHBB sensor solution was then mixed with PBS buffer solution to create a stock solution with QD concentration of ~$8.35 \times 10^{14}$ particles/mL. Three 1.5-mL portions of this stock solution were used for the hybridization experiments, each containing ~2 nmol of QD-cHBB conjugates. One portion, was used as a reference sample, the second was used for hybridization with a stoichiometric amount (2 nmol) of free HBB, and the third for hybridization with a stoichiometric amount (2 nmol) of free HBBs. The target ssDNA solutions were added to the vials containing the QD-ssDNA probes and the vials were placed in a water bath kept at a temperature of 62-64° C. for 40 min. The heating was subsequently stopped and the samples were cooled slowly to room temperature to obtain QD-dsDNA hybridized complexes.

To develop fluorescence intensity vs. concentration calibration lines for the immunoassay experiment, three sets of samples were prepared, each consisting of fifteen test tubes that contained the sensor solution (QD-cHBB) with increasing concentration. One set of these samples was used as reference. A solution containing an equimolar amount of HBB or HBBs target compared to QD-cHBB probe was added to each test tube of the second and third set of samples, respectively. After measuring the fluorescence spectrum of each sample and recording the peak emission intensity, the calibration lines were obtained by plotting the peak emission intensity of QD-cHBB, QD-cHBB/HBB and QD-cHBB/HBBs vs. the concentration of QD-cHBB sensor. An immunoassay was demonstrated by dosing a solution containing a free ssDNA sequence corresponding to HBBs with a solution containing the QD-cHBB sensor. Twelve test tubes were prepared each containing equal amount of the free target solution. A single dose of QD-cHBB solution was added to each, test tube, with each dose containing a progressively increasing amount of probe. After adding the probe and allowing DNA hybridization to occur, the fluorescence spectrum of each sample was measured and the peak emission intensity was plotted as function of the amount of probe added to each test tube.

Fluorescence Spectroscopy

The fluorescence emission spectra of QD-ssDNA conjugates and hybridized complexes were monitored using a SPECTRAmax GEMINI Spectrofluorometer (Molecular Devices). The typical amount of sample used for fluorescence detection was 50 μL and the typical excitation wavelength ranged from 320 to 340 nm. The immunoassay-related fluorescence emission spectra were measured at room temperature using a Flurolog-3 Spectrofluorometer (Horiba Jobin Yvon) with an excitation wavelength of 340 nm.

Results

Conjugation of MUA-capped ZnSe QDs with ssDNA was found to significantly enhance their peak fluorescence emission intensity. MUA-capped ZnSe QDs were dispersed in 1 mL of PBS resulting in a solution containing approximately $2.85 \times 10^{15}$ particles with diameter of approximately 3.5 nm. The QDs were conjugated with 2 nmol amino-modified 25-base oligo(dA), denoted as dA25. Measurement of the fluorescence emission spectrum of the QDs before and alter conjugation with ssDNA indicated that the conjugation increased the QD emission intensity by about five times, with no apparent change in the peak emission wavelength (FIG. 14). Gel electrophoresis was used to verify the formation of QD-dA25 conjugates (FIG. 15). Free dA25 ssDNA and non-conjugated QDs were used as controls. The free ssDNA exhibited higher mobility compared to the non-conjugated QDs, which in turn were more mobile than the QD-dA25 conjugates. This pattern can be explained by considering the different sizes of ssDNA (smallest), MUA-capped QDs, and QD-dA25 conjugates (largest). Changing the molar ratio of QD to DNA from 1:1 to 1:2 did not produce a significant change in the mobility of QD-dA25 conjugates, in agreement with reported gel electrophoresis observations of various DNA-QD conjugates. (Parak, et al 2002 *Chemistry of Materials* 14 (5):2113-2119.)

The variations in QD fluorescence emission intensity upon conjugation of MUA capped QDs to ssDNA can be attributed to better surface protection and stabilization due to the presence of the ssDNA molecules. The addition of ssDNA molecules to the surface (and subsequent hybridization with target ssDNA) also changes the distribution of negative charge around the QD. The rearrangement of the electrostatic/polar environment surrounding the inorganic QD core is likely to affect the local electronic environment inside the QD and cause enhanced radiative electron-hole recombination that leads to the observed increase in fluorescence emission intensity. A recent NMR study of electronic order in ZnSe nanoparticles has shown that the local electronic environment strongly depends on size due to surface-induced, electronic perturbations that propagate into the interior of the nanoparticles. (Cadars, et al. 2009 *Physical Review Letters* 103 (13):4.) It has been estimated that electronic effects induced by surface phenomena, such as relaxation or organic-inorganic interactions, will propagate farther than 1 nm from the surface to the interior of the nanoparticle.

The number and length of ssDNA molecules conjugated with each ZnSe QD (but not their nucleotide sequence) affected the fluorescence emission intensity of the QDs (FIG. 16). The fluorescence emission intensity of QD-ssDNA conjugates increased with increasing surface coverage of ssDNA on the QDs, as shown in FIG. 16*a* for QD-dT25 conjugates. The fluorescence-emission intensity of the QD-dT25 conjugates increased as the amount of dT25 conjugated to the MUA layer covering the QD surface increased. The effect of ssDNA length on QD fluorescence intensity was studied by conjugating ZnSe QDs (4 nm in diameter) with oligo(dA) containing 10, 25, or 50 bases. The fluorescence emission intensity of the QD-ssDNA conjugates increases with increasing ssDNA length and appears to reach a plateau for longer ssDNA molecules (FIG. 16*b*). Longer DNA strands provide, in general, better protection and stabilization of the ZnSe core. However, long ssDNA molecules are more likely to coil and prevent additional ssDNA molecules from covalently binding to the QD. This steric hindrance reduces the number of ssDNA molecules that can be attached to a given QD and eventually counteracts the increased stabilization clue to the longer strand length. FIG. 16*c* shows the QD emission intensity after conjugation with the same amount of ssDNA molecules having the same length (25 bases) but a different chemical sequence. The results indicate that the observed fluorescence emission intensity amplification depends only on the length of the ssDNA and not on the specific nucleotide sequence.

Similarly, changing ssDNA sequence chemistry, without altering ssDNA length, did not affect the fluorescence emission intensity of QD-ssDNA conjugates containing (ZnSe)ZnS core-shell QDs. In FIG. 17*a* the emission spectra of (ZnSe)ZnS core-shell QDs that have been conjugated with dA25 and dT25 are compared to the initial spectrum of water-dispersed MUA-capped (ZnSe)ZnS core-shell QDs. In both cases, the conjugation with DNA enhanced the emission intensity by about four times and was independent of the sequence chemistry of the ssDNA.

Increasing the thickness of the ZnS shell in (ZnSe)ZnS core-shell QDs resulted in progressively smaller fluorescence emission intensity enhancement upon conjugation with ssDNA. (ZnSe)ZnS core-shell QDs with different shell thickness were prepared and conjugated with amino-modified oligo-dT25. The thickness of the shell was estimated from the amount of reactants added to form the ZnS shell, using ZnSe QDs of known average size as a substrate and assuming complete utilization of the reactants used to form the ZnS shell. This is a reasonable assumption because the ZnSe QDs are expected to enable heterogeneous nucleation of ZnS on their surface and conversion of the reactants to a ZnS shell around each ZnSe QD. Equal molar amounts of QDs and oligo-dT25 were used to obtain QDs conjugated with a single oligo-dT25 molecule on average. In FIG. 17*b*, the fluorescence emission intensity of ZnSe QDs and (ZnSe)ZnS core-shell structures with variable shell thickness is plotted before and after conjugation with oligo-dT25. As the thickness of the shell was increased from (no shell) to ~0.3 nm to ~0.9 nm, the degree of fluorescence emission enhancement upon oligo-dT25 conjugation decreased. The growth of a progressively thicker ZnS shell over the ZnSe QD core increases the fluorescence emission intensity of the QD core, but also minimizes and eventually eliminates its ability to sense variations in the outer layer of its capping molecules. A very thick shell can completely isolate the core from its chemical environment, but may also significantly reduce its quantum yield. (Chen, et al. 2008 *Journal of the American Chemical Society* 130 (15):5026.)

The initial fluorescence intensity of MUA-capped ZnSe QDs exhibited run-to-run variations, but the observed amplification of the peak emission intensity upon, conjugation of the MUA-capped QDs to ssDNA was persistent and significant in all cases that that were tested. These run-to-run variations were not significant to prevent unambiguous detection of the binding of the QD-ssDNA sensors to their targets.

Conjugation of ZnSe QDs with ssDNA resulted in aqueous solutions that were stable over a period of several weeks. To investigate the stability of QD-ssDNA conjugates in PBS, the fluorescence emission intensity of QD-ssDNA conjugates was monitored over a period of 35 days and compared to the fluorescence intensity of MUA-capped QDs that were also dispersed in PBS (FIG. 18). The fluorescence emission intensity of ZnSe QDs decreased with time, reaching ~50% of the initial value in 7 days, whereas the intensity of (ZnSe)ZnS core-shell QDs decreased much more slowly, reaching ~50% of the initial intensity in 34 days. Both ZnSe-ssDNA and (ZnSe)ZnS-ssDNA conjugates initially exhibited an increase in fluorescence intensity followed by a slow decrease. The initial increase can be attributed to the attachment of additional ssDNA molecules to the QD surface. This occurs by a slow diffusion-limited process that overcomes steric effects and leads to saturation of the surface with ssDNA and attainment of the most stable conformation of the surface capping layer. Although some decay in fluorescence intensity followed this initial increase, the QD-ssDNA conjugates maintained their original fluorescence intensity after 14 days in storage at room temperature under dark conditions. The fluorescence intensity decreased to 50% of its initial value after 20 days for ZnSe QD-ssDNA and 30 days for (ZnSe)ZnS core-shell QD-ssDNA.

Since the size of QDs is comparable to, or slightly larger than, that of most proteins, several protein molecules can be conjugated to a single QD. (Medintz, et al 2003 *Nature Materials* 2 (9):630-638.) The ZnSe QD-ssDNA conjugates used in our work were fabricated using QD populations with an average size between 3 and 5 nm. Since the width of double-stranded (ds) DNA is about 2 nm, several DNA molecules can be linked to a single ZnSe QD. The total number of DNA molecules bound to the QD surface will be limited by steric effects, with bound DNA hindering the binding of additional free DNA, an effect that will be more pronounced for longer DNA strands.

The conjugation of amino-modified ssDNA to QDs can result in three possible conformations. The first arises from nonspecific binding of the individual ssDNA to the QD surface. The second arises from the formation of an amide covalent bond, C(O)NH, between the ssDNA and the MUA, with the ssDNA chain attaining a random-coil conformation pointing towards the surrounding solution due to entropic effects. The third conformation is similar to the second, except for a stretched ssDNA configuration that allows more ssDNA to bind to the surface. Gains in binding energy for the amide bond formation favor the stretched configuration of the dangling part of the oligonucleotide, which allows DNA to be packed onto the surface of a QD close to the geometric limit. The random-coil configuration creates steric hindrance for free ssDNA and delays the saturation of the surface with ssDNA. It takes some time for the free ssDNA to eventually overcome this steric hindrance and covalently bind to the QD surface. As a result, in a PBS buffer solution containing QD-ssDNA, free ssDNA, and EDC linker, additional free ssDNA can be conjugated to the surface of the QD with time, until the QD surface is saturated with ssDNA. This leads to enhanced surface stabilization and can explain the observed increase in the fluorescence emission intensity of QD-DNA complexes after one week in storage at room, temperature.

Two types DNA hybridization experiments were performed, using QD-ssDNA conjugates: (a) QD-ssDNA hybridization with complementary ssDNA, which is also conjugated to QDs from the same QD batch, and (b) QD-ssDNA hybridization with free complementary ssDNA. Hybridization of QD-ssDNA with complementary ssDNA, either in free form or bound to other QDs, resulted in significant fluorescence emission intensity amplification of the QDs. An example of (a) is shown in FIG. 19. Complementary ssDNA molecules were conjugated with ZnSe QDs and the fluorescence spectra of the QDs were recorded before and after hybridization. In this case, equal, quantities of QD-dA25 and QD-dT25 conjugates were mixed in PBS and the mixture was heated to 55° C. for 30 minutes to denature the DNA and was subsequently cooled to room temperature to allow hybridization of complementary QD-ssDNA conjugates to form QD-dsDNA-QD hybridized structures. The fluorescence emission spectra of the two QD-ssDNA conjugates were identical (FIG. 19*a*) because the QDs were from the same batch, the two ssDNA molecules had the same length, and their doses were equal. After allowing DNA hybridization to occur, a red-shift in the fluorescence emission spectrum was observed (FIG. 19*a*), accompanied by a significant enhancement in the fluorescence emission intensity (FIG. 19*b*).

Hybridization of complementary ZnSe QD-ssDNA conjugates leads to the formation of three-dimensional structures consisting of QDs linked by dsDNA. The amplification, of the fluorescence emission intensity can be attributed to changes in the surface charge distribution around the QDs due to the formation of DNA-linked QD assemblies that lead to an increase in the radiative recombination of electrons and holes. The red shift in the peak emission, wavelength can be explained by the increased local concentration of QDs, which can lead to absorption of the radiation emitted from smaller QDs by the larger ones. Such a red shift has also been observed in dense QD dispersions during studies of the effects of dilution on the photoluminescence of ZnSe QDs. (Mei et al. 2008 *Appl. Phys. Lett* 93 (8):3.) When the temperature of the hybridized mixture was increased to 70° C. to induce DNA denaturation, both the QD emission intensity and peak emission wavelength decreased back to the values observed before hybridization. By slowly cooling the mixture back to room temperature, DNA hybridization occurred again and the fluorescence emission characteristics of the QDs returned to the initial level. This indicates that the observed fluorescence emission enhancement is due to DNA hybridization.

To study the effects of DNA length on QD fluorescence enhancement after hybridization, a set of hybridization experiments were performed using QD-ssDNA conjugates with variable number of nucleotide bases. QD-dA conjugates having 10, 25 and 50 base pairs were hybridized with equal molar quantities of QD-dT conjugates of equal length and their fluorescence emission intensity was recorded before and after hybridization. The results shown in FIG. 20 demonstrate that the degree of emission amplification caused by hybridization decreases as the DNA length increases.

Hybridization experiments employing ZnSe QD-dT25 sensors in the presence, of free complementary ssDNA targets (dA25 and dA10) were also performed. In these experiments, equal quantities of a QD-dT25 complex and free dA25 or dA10 were mixed in PBS buffer solution and the mixture was kept in a water bath at 50° C. for 30 minutes and subsequently cooled to room temperature to allow DNA hybridization. The fluorescence emission spectra of the QD-dT25 sensors before and after hybridization were recorded. Hybridization of QD-dT25 with either free dA25 or free dA10 ZnSe QD-ssDNA did not change the normalized emission spectrum, as shown in FIG. 3; no shift in the emission peak and no significant changes in the shape of the spectrum were observed. However, hybridization of QD-dT25 with free dA25 was accompanied by significant peak emission amplification, as shown, in FIG. 3. A partially hybridized structure was also formed by mixing equal molar amounts of QD-dT25 and free dA10. The resulting QD-dT25/dA10 hybridized complexes exhibited a smaller peak emission amplification compared to the fully hybridized one.

Development of a Homogeneous DNA Dejection Assay

The HBB gene is found in region 15.5 on the short (p) arm of human chromosome 11 (FIG. 21).

To test the ability of QD-ssDNA sensors to detect the presence of HBB and its mutant HBBs, a 21-base probe was designed that is complementary to the sequences of the health HBB gene and conjugated it to MUA-capped ZnSe QDs at 1:1 probe to QD molar ratio. FIG. 22 schematically depicts the expected results from hybridization of the ZnSe QD-cHBB probe with HBB (upper diagram) or HBBS (lower diagram) targets, simulating the presence of denatured (i.e., single-stranded) DNA from healthy and sick patients, respectively. The probe was expected to hybridize completely with the HBB sequence, while the single mismatched base near the middle of probe in the HBBs sequence was expected to reduce the probe-target hybridization efficiency.

The resulting QD-cHBB sensor was used to detect the presence of (and discriminate between) two free ssDNA targets in solution, one consisting of a complementary sequence (HBB) and the second of a common single-base mutation (HBBs). FIG. 23 shows the peak emission intensity amplifications obtained from ZnSe QDs after the QD-cHBB sensor was allowed to hybridize with free HBB or HBBs target. The intensify amplification was greater when the QD-cHBB sensor was hybridized with its exact match (HBB), compared to the mutant HBBs. The difference in the observed amplification between the two hybridized structures was about 20%. This result indicates that ZnSe QDs are useful for developing DNA sensors for rapid detection of healthy vs. mutant DNA sequences in solution.

A homogeneous DNA detection assay that employs ZnSe QD-Single Stranded DNA probes may employ the protocol outlined in the schematic shown in FIG. 24.

The variation in the fluorescence emission intensity of the ZnSe QD sensors upon hybridization of the probe DNA enables the development of distinct calibration lines for the probe and its complexes with healthy and mutant sequences. The example shown in the schematic corresponds to rapid quantitative detection of a mutant gene. Experiments with ZnSe QD-cHBB sensors that can detect the HBBs gene have been performed to demonstrate the operation and robustness of the assay.

Note that for the case of a heterozygote (a patient with one healthy and one mutant gene) the calibration line for the bound sensor will fail exactly in the middle of the (sensor+mutant) and (sensor+healthy) lines because of the equal contribution of mutant and healthy genes to the fluorescence emission intensity amplification after binding of the QD-cHBB sensor to each of the targets.

To demonstrate the use of a ZnSe QD-cHBB sensor for quantitative detection of free ssDNA targets, a homogeneous (non-separation) assay was performed using HBBs as the target. The assay calibration lines were generated first (FIG. 25). The variation in the fluorescence emission intensity of the ZnSe QD-cHBB sensor upon hybridization with the ssDNA target enables the development of three distinct calibration lines, one corresponding to the free sensor and the other two to the (sensor+HBB) and (sensor+HBBs) complexes, respectively.

A homogeneous assay was performed by adding progressively increasing amounts of QD-cHBB sensor to a solution containing 12.5 µmol HBBs per mL of solution. The results are shown in FIG. 26. The recorded peak emission intensity initially follows the (sensor+HBBs) calibration line and then exhibits a transition to the free sensor line alter the free HBBs is exhausted from the solution. The point of departure from the (sensor+HBBs) line corresponds to the initial concentration of free HBBs in the solution. The assay successfully detected the presence and concentration of free HBBs in solution.

Detection Limit

The detection sensitivity of homogeneous assays that do not involve separation of the probe-target complex is limited by the background fluorescence of the solution. A dilution test was performed to identify the limits of detection of the QD-cHBB sensor under the conditions of our experiments.

The detection limit of the technique was studied by comparing the emission intensity from the ZnSe QD-cHBB sensor before and after hybridization with a target sequence for progressively lower concentrations. The experiments were performed using a Flurolog-3 Spectrofluorometer (Horiba Jobin Yvon). The as-prepared Qdots that were used in the sensor had a quantum yield of about 26%. FIG. 27($a$) shows the emission intensity of the QD-sensors before and after hybridization as function of concentration. For the range of concentrations covered in these experiments the fluorescence emission intensity depends linearly upon concentration. The lower line represents the emission intensity of the ZnSe cHBB sensor and the upper line represents the emission intensity of the probe-target hybridized complex. FIG. 27($b$) shows the limit of detection for the instrument that was used, which is about 1 pmol/mL of target in solution. This was obtained by finding the intersection of the emission intensity line of sensor vs. concentration with the emission intensity of the PBS buffer at the same wavelength.

To date, biological applications of QDs have mainly aimed to replace the fluorescent dyes commonly used as biomolecular labels, taking advantage of the size-tunable luminescence, broad excitation, narrow emission and high brightness of the QDs. This work indicates that QDs can be also engineered as responsive fluorescent tags that exhibit significant changes in fluorescence emission intensity when a QD-linked biomolecular probe binds to its specific target. The ultimate objective of our research is to develop QD-based biological sensors that can be used to detect a variety of biomolecular interactions, such as DNA-DNA, antigen-antibody, protein-DNA, lectin-sugar, etc., by measuring the changes in the spectral characteristics of the QDs upon binding of the sensors to their targets.

Thus, Conjugation of ZnSe QDs with ssDNA in aqueous solutions was found to significantly increase the fluorescence emission intensity of the QDs. This phenomenon was attenuated by introducing a ZnS shell and diminished as the thickness of the shell was increased. The fluorescence emission intensity enhancement of ZnSe QDs increased with increasing surface coverage with DMA and with increasing DNA strand length. Variations in the chemical sequence of a DNA strand did not affect the QD fluorescence emission intensity for a given strand length. The QD-ssDNA conjugates were stable in PBS buffer under dark conditions at room temperature and remained fluorescent for several weeks at levels above 50% of their original emission intensity. Hybridization of complementary QD-ssDNA conjugates further enhanced the fluorescence emission, intensity of the QDs and resulted in a red shift of the peak emission wavelength, due to the formation of DNA-linked QD assemblies. More importantly, hybridization of QD-ssDNA probes, having on average a single DNA molecule per QD, with free complementary ssDNA also resulted in significant fluorescence emission amplification with no apparent change in the emission wavelength or shape of the emission spectrum. The observed fluorescence emission intensity amplification upon hybridization of the sensor with the target was affected by the sequence of the free ssDNA target, a property that can be potentially exploited for DNA screening applications. A ZnSe QD-ssDNA sensor containing a sequence complementary to the healthy hemoglobin beta gene (cHBB) showed significant variation in emission intensity upon hybridization with the healthy HBB gene, compared to the HBBs mutant that differs from HBB by a single nucleotide; detection of this HBBs mutant is significant because it is a common cause of sickle cell anemia. The results suggest that ZnSe QDs can be engineered into responsive fluorescent sensors for rapid detection of DNA hybridization and other biomolecular interactions, such as antigen-anti body or protein-DNA, based on measurements of the variations in the fluorescence emission intensity of the QDs upon binding of the QD-biomolecular sensors to their targets.

IV Stability of ZnSe QD-Biomolecule Conjugates

ZnSe QDs and ZnSe QD-biomolecular conjugates in PBS buffer solutions were stored under dark condition at room temperature and their fluorescence emission was measured as function of time in storage.

FIG. 18 shows the evolution of the normalized peak emission intensity of four populations of QDs vs. time in storage. ZnSe QDs and (ZnSe)ZnS core-shell QDs capped with mercaptoundecanoic acid (MUA) exhibit a monotonic decay in fluorescence emission intensity with time in storage, that is more rapid for the ZnSe QDs in comparison to the (ZnSe)ZnS core-shell QDs. The fluorescence emission intensity of ZnSe QDs decreased with time, reaching ~50% of the initial value in 7 days, whereas the intensity of (ZnSe)ZnS core-shell QDs decreased much more slowly, reaching ~50% of the initial intensity in 34 days. Conjugation of the QDs with excess single-stranded DNA (ssDNA) consisting of 25 thymine bases (dT25) to saturate their surface with ssDNA resulted in aqueous solutions that were stable over a period of several weeks. To investigate the stability of QD-ssDNA conjugates in PBS, the fluorescence emission intensity of QD-ssDNA conjugates was monitored over a period of 35 days and compared to the fluorescence intensity of MUA-capped QDs that were also dispersed in PBS. Both ZnSe-ssDNA and (ZnSe)ZnS-ssDNA conjugates initially exhibited an increase in fluorescence emission intensity followed by a slow decrease. The initial increase can be attributed to the attachment of additional ssDNA molecules to the QD surface. This occurs by a slow diffusion-limited process that overcomes steric effects and leads to saturation of the surface with ssDNA and attainment of the most stable conformation of the surface capping layer. Although some decay in fluorescence intensity followed this initial increase, the QD-ssDNA conjugates maintained their original fluorescence intensity after 14 days in storage at room temperature under dark conditions. The fluorescence intensity decreased to 50% of its initial value after 20 clays for ZnSe QD-ssDNA and 30 days for (ZnSe)ZnS core-shell QD-ssDNA.

FIG. 28 shows the evolution of the fluorescence emission intensity of ZnSe QD-dT25 conjugates, with QD to ssDNA ratio of 1:1, and of the corresponding hybridized complexes ZnSe QD-25/25A vs. time in storage. After 45 days in storage, the fluorescence intensity decreased to 20% of the initial value for ZnSe QD-dT25 and to 40% of the initial value for ZnSe QD-25T/25A hybridized complexes.

FIG. 29 shows the evolution of the fluorescence emission intensity of ZnSe QD-BSA conjugates vs. time in storage (BSA: bovine serum albumin). Different samples correspond to ZnSe QDs conjugated with increasing amount of BSA. The fluorescence emission, intensity of the QDs increases for a period of 7 days and it subsequently decreases gradually. After three weeks in storage, the fluorescence intensity of the QDs conjugated to a low amount of BSA was 80% of the original value. For the remaining samples the fluorescence emission intensity was equal to or slightly higher than the initial value after three weeks in storage.

FIG. 30 shows the evolution of the fluorescence emission intensity of a ZnSe QD-BSA conjugate vs. the pH of the solution. A significant monotonic increase in the fluorescence emission intensity of the QDs is observed as the pH is increased. The measured peak emission intensity of the QDs increased by 2.8 times when the pH of the solution was increased from 4 to 12.

FIG. 31 shows the evolution of the fluorescence emission intensity of a ZnSe QD-BSA conjugates stored in solution with different pH values as function of time in storage. The fluorescence emission intensity of QD-BSA conjugates stored in solutions with pH value from 5.4 to 9.1 was stable over a period of five weeks and exhibited an increase from the initial value for the samples stored at pH equal, to 11.08 and 12.06. For the lower pH values, the fluorescence emission intensity of ZnSe QD-BSA complexes gradually decreased with time, with the decrease becoming more pronounced in solutions of lower pH.

Stability in Storage of the ZnSe QD-cHBB Sensor

A ZnSe QD-cHBB sensor stock solution in PBS buffer was stored in a refrigerator at 4~6° C. A fixed amount of this solution was collected at specified times and hybridized with complementary single-stranded DNA (HBB). The fluorescence emission of the ZnSe QD-cHBB sensor solution and the corresponding hybridized complex were measured and the results were plotted in FIG. 32. The fluorescence emission intensity of the ZnSe-cHBB sensor was stable for three weeks in storage and exhibited a decrease of about 30% between weeks three and live. The fluorescence emission amplification upon hybridization of the sensor to a complementary ssDNA target steadily increased with time in storage of the QD-cHBB sensor thus providing unambiguous detection of the target.

V Using of Mn-Doped ZnSe (ZnMnSe) QDs as Biosensor

ZnMnSe Doped QDs: DNA Conjugation and Hybridization

Conjugation of mercapto-succinic acid (MSA) modified Mn-doped ZnSe (ZnMnSe) QDs with ssDNA was found to enhance their peak fluorescence emission intensity. MSA-capped ZnMnSe QDs were dispersed in 1.5 mL of PBS resulting in a solution containing approximately $6.14*10^{14}$ particles with diameter of approximately 7 nm. The QDs were conjugated with 1.5 nmol amino-modified single-stranded DNA, consisting of 25 adenine bases (dA25). Measurement of the fluorescence emission spectrum of the QDs before and after conjugation with ssDNA indicated that the conjugation increased the QD emission intensity by about three times, with no apparent change in the peak emission wavelength (FIG. 33).

Hybridization experiments employing ZnMnSe QD-dA25 conjugates in the presence of free complementary ssDNA target (dT25) were performed. In these experiments, equal molar quantities of a QD-dA25 sensor (with 1:1 QD to ssDNA ratio) and free dT25 target ssDNA were mixed m PBS buffer solution and the mixture was incubated for an hour. The fluorescence emission spectra of the QD-dA25 conjugates before and after hybridization were recorded. Hybridization of QD-dA25 with free dT25 increased the fluorescence emission intensity of the QDs with no shift in the emission peak and no significant changes in the shape of the spectrum (shown in FIG. 34).

Stability of ZnMnSe QDs and QD-dA25 Conjugates

MSA-capped ZnMnSe QDs and ZnMnSe QD-dA25 conjugates in PBS buffer solution were kept under dark condition at room temperature. The fluorescence emission intensity of the QDs was measured as function of time in storage over a period of six weeks and the results were plotted in FIG. 35. The peak emission intensity of ZnMnSe QDs slowly decreases with time and is equal to 85% of its initial value after six weeks in storage. The peak emission intensify of ZnMnSe QD-dA25 conjugates decreases slightly more rapidly with lime and is equal to 75% of its initial value after six weeks in storage.

VI QDs Conjugation with Lectin and Binding with Sugar

ZnSe and ZnMnSe QD Conjugation with Concanavalin A

Concanavalin A (Con A) is a lectin protein originally extracted from *Canavalia Ensiformis*. Concanavalin A is also a lymphocyte mitogen. It is widely believed to be involved in the interaction between alpha-mannosyl oligosaccharides on the surface of the HIV virus and the human T cell lymphocyte, used by the HIV virus to enter the T cell. Lectins are versatile probes for detecting glycoconjugates in histochemical and flow cytometric applications and for localizing glycoproteins in gels. Concanavalin A selectively binds to α-mannopyranosyl and α-glucopyranosyl residues. The binding interaction between a lectin and a specific sugar residue is analogous to that between an antibody and an antigen. In neutral and alkaline solutions, concanavalin A exists as a tetramer with a molecular weight of approximately 104,000 daltons. In acidic solutions (pH below 5.0), concanavalin A exists as a dimer. FIG. 36 shows the fluorescence emission spectra of MUA-capped ZnSe QDs in PBS buffer solution before and after conjugation with Con A, and FIG. 37 compares the fluorescence emission change of ZnMnSe QDs unpon conjugation with Con A. In both cases, conjugation of QDs with Con A increases the fluorescence emission intensity of QDs.

ZnSe QD-ConA and ZnMnSe QD-ConA Binding with methyl-α-D-mannopyranoside

The binding of ZnSe QD-ConA and ZnMnSe QD-ConA conjugates with methyl-α-D-mannopyranoside (M) was studied. Since the conjugation experiments were performed in PBS buffer that has pH value of 7.44 and Con A exists as a tetramer, binding of up to four methyl-α-D-mannopyranoside molecules to one Con A molecule is possible. The binding ratios of Con A to M tested were 1:1, 1:2, 1:3 and 1:4 (as shown in FIG. 38).

The binding of methyl-α-D-mannopyranoside molecules with QD-ConA sensors increased the fluorescence emission of QDs. The fluorescence emission enhancement was stronger for the cases corresponding to one and three bound methyl-α-D-mannopyranoside molecules per QD-ConA molecule when compared to the cases corresponding to two and four bound methyl-α-D-mannopyranoside molecules per QD-ConA sensor molecule (as shown in FIG. 39).

Stability of QD-ConA Conjugates

The fluorescence emission intensity of QD-ConA Conjugates was studied as function of time in storage at room temperature. FIG. 40 shows the normalized peak emission intensity of ZnSe QDs, ZnSe QD-ConA conjugates, and ZnSe QD-ConA/M bound complexes in PBS buffer solution vs. time in storage at room temperature. The fluorescence emission intensity decreases with, time in all cases. The emission intensity of the ZnSe QD-ConA sensor is about 20% of its initial value after five weeks in storage. The QD-ConA/3M and QD-ConA/4M bound complexes exhibit the smallest decrease in fluorescence emission intensity after five weeks with a value equal to 30% of the initial intensity.

FIG. 41 shows the normalized peak emission intensity of ZnMnSe QDs, ZnMnSe QD-ConA conjugates, and ZnMnSe QD-ConA/M bound complexes in PBS buffer solution vs. time in storage at room temperature. In this case the fluorescence emission intensity of the QDs still decreases with time but the decrease is much slower for the QD-conA sensor and the QD-conA/3M bound complex when compared to the ZnSe QDs. The emission intensity of the ZnMnSe QD-ConA sensor is about 50% of its initial value after five weeks in storage. The ZnMnSe QD-ConA/3M bound complex exhibits the smallest decrease in fluorescence emission intensity after six weeks in storage with a value equal to 75% of the initial intensity.

Sensor Calibration Lines

An example of calibration lines for a ZnSe QD-ConA sensor is shown in FIG. 42. The measured emission intensity amplification factor when a ZnSe QD-ConA sensor is bound to four methyl-α-D-mannopyranoside molecules is about 1.5.

VII. Detection of Antigen-Antibody Interactions and Design of a Competitive Homogeneous Immuno-Assay ZnSe QDs capped with MUA were conjugated with HSA and subsequently used in a competitive, homogeneous immunoassay for detection of free HSA in solution. This assay employs a novel QD-protein (HSA) sensor that competes with free protein (HSA) in solution for binding to an anti-HSA antibody. The changes in the peak fluorescence emission intensity of the ZnSe QDs before and after binding enable a rapid quantitative detection of the free protein in solution in a single step.

(a) Preparation of ZnSe QD-HSA Sensor

ZnSe QDs functionalized with mercapto-undecanoic acid (MUA) were conjugated with HSA and anti-human serum albumin (anti-HSA) by a two-step procedure using N-(3-Dimethylaminopropyl)-N'-ethylcarbodiimide hydrochloride (EDC) and N-hydroxylsulfosuccinimide (Sulfo-NHS) as cross-linkers, following a standard protocol. 8 mg of EDC and 40 µL freshly made NHS-water solution (concentration of NHS: 10 mg/mL) were added to 2.0 mL of QD PBS buffer solution (QD concentration: $1.06 \times 10^{15}$/mL) and the solution was stirred slowly for 30 minutes at room temperature. Next, 3~4 nmol of HSA were added to the solution. The ratio of the number of ZnSe QDs to the number of antigen molecules available for conjugation was controlled to be equal to unity. The mixture was incubated at room temperature for 4 hours to complete the covalent coupling reaction and allowed to stay overnight to enhance QD stabilization.

(b) Binding of ZnSe QD-HSA to Anti-HSA Antibody

The ZnSe QD-HSA sensor was exposed to anti-HSA antibody in a homogeneous assay as follows: A stoichiometric amount of 0.8 nmol of anti-HSA was added to 1 mL ZnSe QD-HSA PBS buffer solution. The amount of anti-HSA added was equal to the molar quantity of HSA conjugated with the QDs. The binding of antibody to the QD-antigen probe was rapid. The fluorescence emission from the samples was measured using a Flurolog-3 Spectrofluorometer (Horiba Jobin Yvon). FIG. 43 shows an example of fluorescence emission intensity amplification when a ZnSe QD-HSA labeled antigen binds an anti-HSA antibody to form a ZnSe QD-HSA/anti-HSA bound complex. A single ZnSe QD is attached to one HSA molecule.

Assay Calibration: Experiments were performed using progressively smaller stoichiometric amounts of ZnSe QD-HSA and anti-HSA and the peak fluorescence emission intensity of die QDs before and after binding was plotted as function of concentration. FIG. 44a shows the two calibration lines corresponding to peak fluorescence emission intensity from free ZnSe QD-HSA and the ZnSe QD-HSA/anti-HSA complex. In this range of concentrations the fluorescence emission intensity is a linear function of the concentration. These two lines provide the upper and lower limits of fluorescence intensity that are used to develop the homogeneous assay described next. The limit of detection for the instrument used was obtained by finding the intersection of the emission intensity line of ZnSe QD-HSA with the emission from the PBS buffer at the same wavelength (as shown, in FIG. 44b). Using as-prepared ZnSe QDs with quantum yield of ~34% in the QD-HSA sensor, the limit of detection of free HSA was 0.04 µg/mL for the instrument used in these experiments.

Competitive Homogeneous (Separation-Free) Assay for Determining HAS Concentration in Human Plasma A competitive assay was performed to measure the concentration of human serum albumin (HSA) in human serum obtained from platelet-poor pooled human plasma, from healthy adults that was purchased from Sigma-Aldrich. The concentration of human serum albumin in human serum plasma from healthy donors is between 600 and 800 µmol/L. The human serum plasma was diluted 1000 times to make the HSA concentration to be between 0.6 and 0.8 nmol/L. To perform the assay, 12 test tubes each containing 100 µL of the diluted human serum plasma were prepared. An increasing amount of a ZnSe QD-HSA sensor and free anti-HSA antibody solution was then added to each test tube and the fluorescence emission spectrum of each sample was measured. FIG. 45a shows the two calibration lines of the assay that were obtained by monitoring the peak fluorescence emission from an unbound QD-HSA sensor and a bound QD-HSA/antiHSA sensor-target complex as function of the concentration of sensor and sensor-target complex, respectively. The measured emission intensity during the execution of the assay as function of the sensor concentration added to the sample is also shown in FIG. 45a. At low sensor concentrations, the free HSA antigen is at higher concentration in comparison to the sensor and competes effectively to bind die antiHSA antibody, thus leading to measured emission intensity corresponding to free QD-HSA sensor. As the concentration of the added QD-HSA sensor and antiHSA is increased, the sensor starts competing more effectively with the target HSA in terms of binding the antiHSA antibody and observed fluorescence emission intensity transitions to that corresponding to the sensor-target bound complex. The normalized emission intensity of the assay was calculated and shown in FIG. 45b. The scaled emission intensity is initially equal to zero, a value corresponding to the emission from the free sensor, it transitions to the value of one that corresponds to the bound sensor-target complex as the concentration, of the added sensor and antibody is increased and the free antigen is depleted. At that point, the assay is terminated. At the end of the assay a total of 0.125 nmol of anti-HSA and 0.054 nmol of ZnSe QD-HSA were added to the sample solution. The difference between the anti-HSA and labeled HSA added to the solution is 0.071 nmol, which corresponds to 0.071 nmol of free HSA bound to the antibody. This means that the 100 μL of 1000× diluted human serum plasma contains 0.071 nmol HAS. Thus the concentration of HSA in the 1000× diluted human, serum plasma is 0.71 μmol/L and the concentration in the non-diluted human serum plasma, is 710 μmol/L, which is within the expected range of concentrations for healthy adults.

Direct Homogeneous Assay for Detecting Fibroblast Growth Factor (FGF)

A direct homogeneous immunoassay was also developed and used to detect free FGF as in solution using ZnSe QD-antiFGF as the sensor, with 1:1 QD to antiFGF ratio. The ZnSe QD-antiFGF sensor was initially exposed to stoichiometric amounts of free FGF antigen in a homogeneous assay (the amount of FGF added was equal to the molar quantity of anti-FGF conjugated with the QDs). FIG. 46 shows the recorded fluorescence emission intensity amplification when a ZnSe QD-antiFGF sensor binds free FGF to form a ZnSe QD-antiFGF/FGF bound complex.

A direct assay requires dosing the solution containing the target with the sensor only. In such a ease the recorded emission will transition from the sensor+target calibration line to the sensor only calibration line after the entire amount of free antigen is bound to the sensor. The concentration of free antigen will be equal to the concentration of sensor at the point at which the dose response curve of the assay departs from the upper calibration line.

A direct homogeneous assay that detects free FGF in solution using a ZnSe QD-antiFGF sensor was executed by adding progressively higher amounts of sensor to a solution containing 0.14 μg FGF. The results are shown in FIG. 47. The recorded peak, emission intensity initially follows the sensor+target calibration line and transitions to the sensor only line (lower line) after the free FGF is depleted from the solution. The point of departure from the sensor+target line corresponds to the initial concentration office FGF in the solution (as shown in FIG. 47a). In this case, a solution initially containing 0.14 μg of free FGF was used and the solution was dosed with ZnSe QD-antiFGF until the emission intensity from the solution departed from the ZnSe QD-antiFGF/FGF line. At this point, the added ZnSe QD-antiFGF sensor is 0.0066 nmol corresponds to 0.146 ug of antiFGF. Since one antiFGF molecule binds one FGF target, the measured concentration of free FGF is 0.146 ug, which is in good agreement with the FGF concentration in the stock solution (0.14 μg).

The normalized emission intensity is plotted in FIG. 47b. A normalized emission intensity value of one corresponds to the sensor+target complex and a value of zero to the free sensor. The normalized emission intensity is initially equal to unity and later transitions to zero as the free FGF is depleted from the solution. At that point, the assay is terminated. The initial molar concentration of free FGF in the sample is equal to the molar concentration of sensor at the point of departure of the dose response curve of the assay from the sensor+target line.

Direct Immunoassays for Rapid Quantitative Detection of Prostate-Specific Antigen (PSA) and *Chlamydia trachomatis* Antigen.

Direct homogeneous (separation-free) immunoassays were developed for detection of prostate specific antigen (PSA) and *Chlamydia trachomatis* antigen (*C. trachomatis* antigen or CTA) in PBS buffer solutions using ZnSe QD-antiPSA and ZnSe QD-antiCTA sensors containing 1:1 ratio of QD to antibody. The assays were calibrated and executed in a similar way to the FGF assay.

FIG. 48 shows the fluorescence emission difference between a ZnSe QD-antiPSA sensor and the corresponding ZnSe QD-antiPSA/PSA bound complex.

A direct homogeneous assay that detects free PSA in solution using a ZnSe QD-antiPSA sensor was executed, by adding progressively increasing amounts of sensor solution to PBS buffer solution containing free PSA. Prostate Specific Antigen (PSA_buffer solution was bought from Sigma-Aldrich with concentration of 2.83 mg/mL of PSA. This PSA solution was diluted 3600 times and the resulting stock solution was used as the target solution for the assay.

To perform the assay, 10 test-tubes each containing 100 μL of diluted PSA solution with concentration equal to 786 ng/mL were prepared. Increasing amounts of ZnSe QD-antiPSA were added to each test tube and the fluorescence emission intensity of each sample was measured. The results are shown in FIG. 49. The recorded peak emission intensity initially follows the sensor+target calibration line and transitions to the sensor only line when the free PSA is exhausted from the solution. The point of departure from the sensor+antigen line corresponds to the initial concentration of free PSA in the solution. In this case, each of the 100 μL samples being contained 78.6 ng of free PSA. The concentration of QD-antiPSA (1:1) sensor that corresponds to the departure from the sensor+target line was equal to 0.0026 nmol/mL. Assuming 1:1 antigen-antibody binding, the free PSA concentration in the sample was calculated to be 78.6 ng PSA added, in agreement with the initial amount in the stock solution.

For the ease of *C. trachomatis* antigen detection, the assay was executed by adding progressively increasing amounts of ZnSe QD-antiCTA sensor solution to a *C. trachomatis* antigen PBS buffer solution. *C. trachomatis* antigen (Major Outer Membrane Protein or MOMP—here abbreviated as CTA) was bought from Microbix Biosystems with concentration of 5.45 mg/mL. The *C. trachomatis* antigen solution was diluted 100 times before using it in the assay. To perform the assay, 12 test tubes each containing 45 μL of diluted solution with concentration of 54.5 μg/mL CTA were prepared. An increasing amount of QD-antiCTA sensor was added to each sample and the corresponding fluorescence emission spectrum was measured. The normalized-peak emission intensity results are plotted in FIG. 50. A value of normalized peak emission intensity equal to one corresponds to the QD-antiCTA/CTA (sensor+target) complex and a value equal, to zero corresponds to the QD-antiCTA sensor. The normalized peak emission intensity is initially equal to one and later transitions to zero as the free *C. trachomatis* antigen is depleted from the sample. At that point, the assay was terminated and the initial molar amount of free *C. trachomatis* antigen in the sample was calculated from the amount of QD-antiCTA sensor corresponding to the point of departure from the sensor+target line. This value corresponds to 0.06 nmol/mL of sensor at the target depletion, point. By assuming 1:1 binding of sensor to target the amount of free *C. trachomatis* antigen in the sample is estimated to be 3.6 µg. The initial amount of CTA was 2.45 µg, which indicated that the binding of sensor to target is not 1:1. The difference can be attributed to the fact that the antibody used is a polyclonal antibody and not a monoclonal one, as was the case in the other assays. The CTA assay can be calibrated based on this information and tuned, to precisely detect the target concentration.

Homogeneous Immuno-Assay for Rapid Quantitative Detection of Fibroblast Growth Factor (FGF) Using a ZnSe QD-Anti-FGF Sensor.

A ZnSe QD-anti-FGF sensor was developed by conjugating ZnSe QDs with anti-FGF antibody. This sensor is much brighter than a QD-anti-HSA, as shown in FIG. 51.

The results from conjugation of the QD anti-HSA and QD-anti-FGF sensors with free HSA and free FGF are shown in FIG. 52. The QD-anti-FGF/FGF complex exhibits higher emission intensity amplification than the QD-anti-HSA/HSA complex. As a result, a QD-anti-FGF sensor is a better candidate for a regular (non-competitive) homogeneous immunoassay for rapid quantitative detection of FGF in solution than a QD-anti-HSA sensor would be for detection of free HSA. A regular non-competitive assay requires dosing the solution containing the target with the sensor only. In such a case the recorded emission will transition from the upper calibration line to the lower calibration line when all free antigens in solution bind to the probe. The concentration of free antigen will be equal to the concentration of sensor at the point at which the dose response curve departs from the upper calibration line.

The emission amplification of the QD-antigen vs. QD-antibody after binding with their corresponding targets can be used as a guide for selecting which component of the assay to label with the QDs to optimize the detection limit of the assay.

Incorporation by Reference

References and citations to other documents, such as patents, patent applications, patent publications, journals, books, papers, web contents, have been made in this disclosure. All such documents are hereby incorporated herein by reference in their entirety for ail purposes.

Equivalents

The representative examples are intended to help illustrate the invention, and are not intended to, nor should they be construed to, limit the scope of the invention. Indeed, various modifications of the invention and many further embodiments thereof in addition to those shown and described herein, will become apparent to those skilled in the art from the full contents of this document, including the examples and the references to the scientific and patent literature included herein. The examples contain important additional information, exemplification and guidance which can be adapted to the practice of this invention in its various embodiments and equivalents thereof.

The invention claimed is:

1. An optical biomolecular sensor for detecting a target biological material, comprising:
   (a) a nanocrystal selected from the group consisting of a single ZnSe nanocrystal and a single CdSe nanocrystal, wherein the single ZnSe nanocrystal consists of ZnSe and the single CdSe nanocrystal consists of CdSe, and wherein the single ZnSe nanocrystal has a particle size from about 1 nm to about 9 nm capable of fluorescing at a pre-selected wavelength range from about 375 nm to about 450 nm upon excitation and the single CdSe nanocrystal has a particle size from about 2 nm to about 7 nm capable of fluorescing at a pre-selected wavelength range from about 480 nm to about 640 nm, wherein the single ZnSe nanocrystal or the single CdSe nanocrystal has a surface allowing aqueous solubility of the single ZnSe nanocrystal or the single CdSe nanocrystal;
   (b) a biomolecular probe having an affinity to the target biological material, wherein the biomolecular probe is selected from single-stranded oligonucleotides, antibodies, antigens and immune receptors; and
   (c) a linkage moiety associated with the single ZnSe nanocrystal or the single CdSe nanocrystal via covalent bonding and having a functional group through which the linkage moiety is covalently bonded to the biomolecular probe via covalent bonding,
wherein the linkage moiety is selected from mercaptocarboxylic acids and the covalent bonding to the nanocrystal is through the thiol group of the mercaptocarboxylic acid,
wherein the surface of the single ZnSe nanocrystal or the single CdSe nanocrystal is saturated with the linkage moiety,
wherein the ratio of the single ZnSe nanocrystal or the single CdSe nanocrystal to the biomolecular probe is 1:1, and
wherein binding of the biomolecular probe with the target biological material results in an increase in the fluorescence emission intensity of the single ZnSe nanocrystal or the single CdSe nanocrystal, compared to the fluorescence emission intensity of the single ZnSe nanocrystal or the single CdSe nanocrystal prior to binding.

2. The optical biomolecular sensor of claim 1, wherein the biomolecular probe is an antibody and the linkage moiety is a mercaptocarboxylic acid.

3. The optical biomolecular sensor of claim 1, wherein the biomolecular probe is an antigen and the linkage moiety is a mercaptocarboxylic acid.

4. The optical biomolecular sensor of claim 1, wherein the biomolecular probe is a single-stranded oligonucleotide and the linkage moiety is a mercaptocarboxylic acid.

5. The optical biomolecular sensor of claim 1, wherein the population of the single ZnSe nanocrystal or the single CdSe nanocrystal is either monodisperse with particle sizes that deviate less than about 10% in root mean square diameter or polydisperse with particle sizes that deviate more than about 10% in root mean square diameter.

6. The optical biomolecular sensor of claim 1, wherein the nanocrystal is a single ZnSe nanocrystal.

7. The optical biomolecular sensor of claim 1, wherein the nanocrystal is a single CdSe nanocrystal.

* * * * *